US008859235B2

(12) United States Patent
Kaufmann et al.

(10) Patent No.: US 8,859,235 B2
(45) Date of Patent: Oct. 14, 2014

(54) METHODS IN CELL CULTURES, AND RELATED INVENTIONS, EMPLOYING CERTAIN ADDITIVES

(75) Inventors: Franz Kaufmann, Freiburg (DE); Trine Hefsgaard Miller, Aesch (CH); Johannes Flothmann, Basel (CH); Beate Winter, Steinen (DE); Andreas Hafner, Gelterkinden (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/389,549

(22) PCT Filed: Aug. 11, 2010

(86) PCT No.: PCT/EP2010/061655
§ 371 (c)(1),
(2), (4) Date: Mar. 19, 2012

(87) PCT Pub. No.: WO2011/018472
PCT Pub. Date: Feb. 17, 2011

(65) Prior Publication Data
US 2012/0164162 A1 Jun. 28, 2012

(30) Foreign Application Priority Data
Aug. 14, 2009 (EP) .................................. 09167885

(51) Int. Cl.
*C12P 21/00* (2006.01)
*C07K 14/54* (2006.01)
*C12P 21/02* (2006.01)
*C12N 1/38* (2006.01)

(52) U.S. Cl.
CPC .. *C12N 1/38* (2013.01); *C12P 21/02* (2013.01)
USPC ........ 435/71.2; 435/71.3; 435/91.1; 435/170; 435/253.6

(58) Field of Classification Search
CPC ...................................................... C12P 21/00
USPC ....................................................... 435/71.2
See application file for complete search history.

(56) References Cited

U.S. PATENT DOCUMENTS

| 3,235,467 | A |   | 2/1966  | Ninet et al. |
|-----------|---|---|---------|--------------|
| 3,632,330 | A | * | 1/1972  | Michaelson .................. 504/160 |
| 3,703,439 | A | * | 11/1972 | Florent et al. ................. 435/108 |
| 3,704,205 | A |   | 11/1972 | Shiro et al. |
| 3,704,208 | A | * | 11/1972 | Russo ........................... 205/126 |
| 3,929,571 | A | * | 12/1975 | Kubota et al. ................ 435/115 |
| 4,898,901 | A |   | 2/1990  | Ravichandran et al. |
| 5,462,946 | A |   | 10/1995 | Mitchell et al. |
| 5,487,884 | A |   | 1/1996  | Bissett et al. |
| 5,607,624 | A |   | 3/1997  | Nesvadba et al. |
| 5,677,315 | A |   | 10/1997 | Carr et al. |
| 6,107,326 | A | * | 8/2000  | Jori .............................. 514/410 |
| 6,486,314 | B1 | * | 11/2002 | Van Geel-Schutten et al. ......................... 536/123.12 |
| 6,521,443 | B1 |   | 2/2003  | Zink et al. |
| 6,605,619 | B1 | * | 8/2003  | Mitchell et al. ............... 514/315 |
| 6,610,284 | B1 | * | 8/2003  | Labsky et al. ............... 424/78.26 |
| 6,682,916 | B2 | * | 1/2004  | Taoka et al. .................... 435/158 |
| 6,825,384 | B1 | * | 11/2004 | Prakash et al. ................ 568/402 |
| 7,323,505 | B2 |   | 1/2008  | Thibaut |
| 7,390,904 | B2 | * | 6/2008  | Galbo et al. ................... 546/184 |
| 7,666,813 | B2 | * | 2/2010  | Hoefer et al. ................. 502/401 |
| 8,003,345 | B2 | * | 8/2011  | Fesenko et al. ............... 435/69.1 |
| 2002/0160398 | A1 | * | 10/2002 | Taoka et al. ........................ 435/6 |
| 2002/0177559 | A1 | * | 11/2002 | de Souza et al. ................ 514/18 |
| 2003/0092764 | A1 | * | 5/2003  | Hsia et al. ..................... 514/509 |
| 2003/0096414 | A1 |   | 5/2003  | Ciccarone et al. |
| 2003/0114358 | A1 |   | 6/2003  | Galinski et al. |
| 2003/0212170 | A1 |   | 11/2003 | Tinkl et al. |
| 2004/0024025 | A1 |   | 2/2004  | Kasid et al. |
| 2005/0059633 | A1 | * | 3/2005  | Van Geel-Schuten .......... 514/54 |
| 2005/0100994 | A1 |   | 5/2005  | Seo et al. |
| 2005/0106686 | A1 |   | 5/2005  | Jetten et al. |
| 2005/0121160 | A1 | * | 6/2005  | Jetten et al. ..................... 162/81 |

(Continued)

FOREIGN PATENT DOCUMENTS

EP    1 764 415    3/2007
WO    91 16034    10/1991

(Continued)

OTHER PUBLICATIONS

Winkler, Barry S et al, The Redox couople between glutathione and ascorbic acid: A chemical and physiological perspective, Free Radical Biology and Medicine, vol. 17(4), pp. 333-349, 1994.*
Hosono, K et al, Agricultural and Biological Chemistry, 1990, vol. 54(7), pp. 1639-1643, Inhibition of Mutagenicity of Lactic Acid Bacteria.*
Rajendran, R et al, Canadian Journal of Microbiology, Feb. 1998, vol. 44(2), pp. 109-115, Binding of heterocyclic amines by lactic acid bacteria from miso, a fermented Japanese food.*
Thitilertdecha, Nont et al, Swiss Society of Food Science and Technology, Antioxidant and antibacterial activities of *Nephelium lappaceum* L. extracts, pp. 2029-2035, vol. 41, 2008.*

(Continued)

*Primary Examiner* — Albert Navarro
*Assistant Examiner* — Ginny Portner
(74) *Attorney, Agent, or Firm* — Oblon, Spivak, McClelland, Maier & Neustadt, L.L.P.

(57) ABSTRACT

A method for the manufacture of products by biotechnological methods in bacterial cell culture is disclosed as well as products obtained, the use of certain additives to the media used in the manufacture of said products in bacterial cell culture media, and the use of said additives in reducing the detrimental effects of radicals in the manufacture of the products, as well as aspects related to these invention embodiments. The manufacturing process or method comprises adding one or more radical scavenging and/or antioxidative additive preferably selected from the group consisting of sterically hindered nitroxyls, sterically hindered hydroxylamines, sterically hindered hydroxylamine salt compounds, sterically hindered amino compounds and sterically hindered N-hydrocarbyloxyamines, benzofuranone compounds, as obligatory component(s) to the medium used during biosynthesis.

13 Claims, No Drawings

(56) References Cited

U.S. PATENT DOCUMENTS

| | | | |
|---|---|---|---|
| 2005/0202967 A1* | 9/2005 | Hoefer et al. | 502/401 |
| 2006/0100224 A1* | 5/2006 | Svenstrup et al. | 514/269 |
| 2007/0034198 A1 | 2/2007 | Arad | |
| 2007/0053871 A1 | 3/2007 | Li et al. | |
| 2007/0062884 A1* | 3/2007 | Sun et al. | 210/764 |
| 2007/0092724 A1* | 4/2007 | Li et al. | 428/375 |
| 2007/0099845 A1* | 5/2007 | Sheu et al. | 514/19 |
| 2007/0110743 A1 | 5/2007 | Drapeau et al. | |
| 2007/0190619 A1 | 8/2007 | Vercauteren et al. | |
| 2008/0090282 A1* | 4/2008 | Binder | 435/235.1 |
| 2008/0200548 A1 | 8/2008 | Goldstein | |
| 2008/0305055 A1* | 12/2008 | Baschong et al. | 424/59 |
| 2008/0305511 A1* | 12/2008 | Lee et al. | 435/25 |
| 2009/0105074 A1* | 4/2009 | Azevedo et al. | 504/101 |
| 2010/0068279 A1* | 3/2010 | Hartwell | 424/486 |
| 2010/0143965 A1* | 6/2010 | Fujita et al. | 435/41 |
| 2010/0285105 A1* | 11/2010 | Radianingtyas | 424/450 |
| 2011/0313672 A1* | 12/2011 | Liu et al. | 702/19 |

FOREIGN PATENT DOCUMENTS

| | | | |
|---|---|---|---|
| WO | 91 16035 | | 10/1991 |
| WO | 00 32687 | | 6/2000 |
| WO | 03 040190 | | 5/2003 |
| WO | 2005/034857 | * | 4/2005 |
| WO | 2005 059152 | | 6/2005 |
| WO | 2008 047113 | | 4/2008 |
| WO | 2008 100782 | | 8/2008 |
| WO | 2008 110465 | | 9/2008 |

OTHER PUBLICATIONS

Gadjeva et al, Toxicology Letters, vol. 144, 2003, pp. 289-294, Spin labeled antioxidants protect bacteria against the toxicity of alkylating antitumor drug CCNU.*

Gooderhan, Nigel J et al, Drug Metabolism and Disposition, vol. 29(4), part 2, pp. 529-534, 2001, Food derived heterocyclic amine mutagens:variable metabolism and significance to humans.*

Barnes, K et al, Journal of Applied Polymer Science, vol. 105, pp. 2306-2313, 2007, Modification of Silica gel, cellulose and polyurethane with a sterically hindered N-halamine moiety to produce antimicrobial activity.*

May, James M. et al, Free Radical Research, Feb. 2005, vol. 39(2), pp. 195-202.*

Tavan, E et al, Journal of Dairy Research, 2002, vol. 69, pp. 335-341.*

Skorko-Glonek, J et al, Mol. General Genetics, 1999, vol. 262, pp. 342-350.*

Poupin, P et al, Applied and Environmental Microbiology, Jan. 1998, vol. 64(1), pp. 159-165, Degradation of Morpholine by an Environmental *Mycobacterium* Strain involves a Cytochrome P-450.*

Bae, Hee-Sung et al, Arch. Microbiol., published on-line Jan. 28, 2009, vol. 191, pp. 329-340, Characterization of diverse heterocyclic amine-degrading denitrifying bacteria from various environments.*

Franzblau, SG et al, Antimicrob. Agents Chemother, 1989, vol. 33(11), pp. 2004-2005.*

Kohler, Henrik et al, The Journal of Infectious Diseases, 2002, vol. 186, pp. 1122-1130, Inhibition of *Salmonella typhimurium* Enteropathogenicity by Piperidine, a metabolite of the Polyamine Cadaverine.*

Horita, Masako et al, Free Radical REsearch, Oct. 2005, vol. 39(10), pp. 1035-1041, Involvement of oxidative stress in hydroquinone-induced cytotoxicity in catalase deficient *Escerichia coli* mutants.*

McDonald, LInda C. et al, Applied and Environmental Microbiology, Feb. 1983, pp. 360-365, vol. 45(2).*

Scholz, O., et al., "Quantitative analysis of gene expression with an improved green fluorescent protein," European Journal of Biochemistry, vol. 267, pp. 1565-1570, (Mar. 1, 2000).

Castagna, R., et al., "Nitroxide radical TEMPO reduces ozone-induced chemokine IL-8 production in lung epithelial cells," Toxicology in Vitro, vol. 23, pp. 365-370, (2009).

Xiao, A., et al., "Improvement of cell viability and hirudin production by ascorbic acid an *Pichia pastoris* fermentation," Applied Microbiology and Biotechnology, vol. 72, pp. 837-844 (2006).

Wolfe, R.A., "Media for Cell Culture," Biotechnology Second Edition, pp. 142-156, (1993).

Arden, N., et al., "Life and death in mammalian cell culture: strategies for apoptosis inhibition," Trends in Biotechnology, vol. 22, No. 4, pp. 174-180, (Apr. 2004).

International Search Report Issued Mar. 17, 2011 in PCT/EP10/61655 Filed Aug. 11, 2010, pp. 1-3.

Office Action as received in the corresponding European Patent Application No. 10 740 674.6-1405 dated Mar. 4, 2014.

Hanna Szpilewska, et al., "Experimental Evidence for the Physiological Role of Bacterial Luciferase in the Protection of Cells Against Oxidative Stress", Current Microbiology, vol. 47, (2003), pp. 379-382.

* cited by examiner

METHODS IN CELL CULTURES, AND RELATED INVENTIONS, EMPLOYING CERTAIN ADDITIVES

This application is a National Stage of PCT/EP10/061655 filed Aug. 11, 2010 and claims the benefit of EP 09167885.4 filed Aug. 14, 2009.

FIELD OF THE INVENTION

The present invention relates to a process or a method for the manufacture of products by biotechnological methods, particularly in bacterial cell cultures, products obtained, the use of certain additives to the media used in the manufacture of said products, especially in the cell culture media, and the use of said additives in reducing the detrimental effects of radicals in the manufacture of the products, as well as aspects related to these invention embodiments.

BACKGROUND OF THE INVENTION

A number of both small and large molecular products, such as antibiotics, monomers for polymeric products, amino acids, organic acids, vitamins, proteins, nucleic acids and the like, can be produced in both cell free and cell culture systems employing biochemical metabolism or reactions. These products include what is also often referred to as biologics, in contrast to chemically manufactured products, though biologics (which include also biosimilars) is often only referred to in order to describe proteinaceous pharmaceuticals.

However, usually, especially in cell culture with living cells, the presence of oxygen is necessary, at least where aerobic organisms are used.

Cellular respiration constantly generates small but significant amounts of reactive oxygen species (superoxide, hydrogenperoxide, hydroxylradicals) that are toxic and can damage cellular constituents (DNA, proteins, lipids). Negative effects of stress in fermentation processes can lead to

- Decreased viability of the cells and thus shortening of the process duration,
- Decreased productivity of the cells,
- Damage to the products.

Cells have developed oxidative stress protection and repair systems during evolution. However, these defense mechanisms may not be sufficient under conditions of High Cell Density Cultivation (HCDC) and in addition require cellular energy that is no more available for product formation. Especially oxidative stress is pronounced in HCDC as high oxygen input into the cultures is needed in order to sustain growth and productivity of cells at high densities. Also in HCDC cellular metabolites and by-products are formed at elevated rates which can impair growth, productivity and product stability.

Production systems for recombinant therapeutic proteins or other products are essentially classified into mammalian cell cultures and microbial systems (bacterial, yeast, fungi):

|  | Mammalian cell culture | Bacterial systems |
| --- | --- | --- |
| Productivity | 10 g/L | 10-50 g/L |
| Cost | High | Low |
| Generation of production cell lines | 6 months | 1-2 months |
| Process cycle time | Weeks | Days |
| Complex modifications (e.g. glycosylation, disulfide bond formation, acylation) | Yes | Limited (no glycosylation) |

A large difference between bacterial and mammalian culture systems is that bacterial growth in a nutrient solution closely resembles their natural life style while growth of suspended mammalian cells has to be considered artificial compared to the natural situation viz. growth in tissues as part of a multi-cellular organism. For mammalian cell culture systems the current trend is to replace complex animal derived media components such as calf serum with chemically defined ones. As complex media contain a large variety of components which among others have anti-oxidative activities, their omission in defined media creates a need for other stress relieving additives.

Oxygen as such, for example, can cause oxidative stress via a number of mechanisms and oxygen species. For example, dimolecular, ground state oxygen, is a free radical, can react readily with carbonyl radicals to form the organic peroxyl radical, thus leading to undesired reactions.

Oxygen can be present as singlet oxygen which exists in two states. The more reactive singlet oxygen state, $O_2$ $1\sigma g$, is a radical that contains two unpaired electrons of opposite spin in separate $\pi$ anti-bonding orbitals. It can be created by reactions with porphyrin or flavins in the presence of light and can react with organic conjugated double bonds to form endoperoxides, dioxetanes and hydroperoxides and peroxides and with organic sulfides to produce sulfoxides. Superoxide contains an additional unpaired electron. It is a radical and can also be formed by several mechanisms in vivo. Transition metals such as iron and copper in the reduced form catalyze a set of reactions that result in the formation of hydroxyl free radicals, another reactive species including oxygen. Hydroxyl free radicals are formed in vitro and in vivo. A well described source for hydroxyl radicals in cells is the Fenton reaction in which hydrogen peroxide reacts with Fe(II) ions to form hydroxyl radicals and $OH^-$ The hydroxyl free radical is an extremely reactive oxidizing species. It causes damage to all classes of bio-molecules, but one of its most damaging immediate effects is the initiation of lipid peroxidation. Lipid peroxidation is a self-propagating event that is mediated by the organic peroxyl radical. Organic peroxyl radicals are formed when allylic carbonyl radicals bind ground-state oxygen. This is an extremely important reaction in vitro and in vivo. The primary molecules that undergo this chemistry are the polyunsaturated fatty acids (PUFAs). Allylic carbonyl radicals are generated when hydroxyl free radicals abstract a hydrogen atom from the allylic carbon. This produces an organic peroxyl radical that participates in a chain reaction of lipid oxidations that lead to cell membrane damage and cell death. Peroxynitrites can be produced by certain cells which produce extracellular nitric oxide as a cell-signaling molecule. Superoxides can react with nitric oxide to from peroxynitrites. Peroxynitrites react very rapidly with carbon dioxide to form carbon monoxide and nitric dioxide radicals.

In general, oxidative stress and other radical reactions can lead to damage at molecules such as proteins, nucleic acids or other small or large molecular weight molecules such as lipids, amino acids, sugars or the like, e.g. at double bonds, sulphur etc. (see e.g. Dean et al., Biochem. J. 324, 1-18 (1997) or Konz et al., Biotechnol. Prog. 14(3), 292-409 (1998)).

Measures taken in the art to prevent and to cope with oxidative and other stresses in protein production processes include 1. Natural Response to Oxidative Stress Although not the matter of human intervention, the natural protection of cells to oxidative stress could be considered as a benchmark. Reactive oxygen species (ROS) are constantly present in cells in low concentration and in elevated concentrations during various stress conditions. Cells protect themselves from damage through ROS by enzymes that detoxify these (superoxide dismutase for superoxide, catalase and several peroxidases for hydrogen peroxide and other hydroperoxides) and by producing cellular antioxidants such as vitamin C and E as well as thiol-containing peptides and proteins (glutathione, thioredoxin) that react with ROS. However conditions applied in the production of proteins by fermentation (high cell densities, high oxygen input, major stress through massive overexpression of one specific protein) may lead to a saturation of these pathways. In addition the cellular repair of oxidative damage draws away metabolic energy (in the form of low potential reducing equivalents) which otherwise is available for product formation.

2. Use of Natural and Synthetic Antioxidants:

Natural antioxidants (Vitamins C & E, polyphenols, amino acids such as cysteine and methionine, peptides such as gluthatione and carnosine) scavenge reactive oxygen species (ROS) and are used in medicine, personal care and nutrition as well as in fermentation processes. There are also examples of synthetic antioxidants and radical scavengers being used in fermentation, however to our knowledge the use of nitroxide, HALS type molecules or phenolic antioxidants for increasing the productivity of cells in fermentation has never been described. There are also references (mostly from journals, see following page) describing that nitroxides and related substances can diminish the level of oxidative stress in mammalian cell culture and thus increase cellular lifetime by inhibiting programmed cell death (=apoptosis). However this effect seems to be cell line specific and dependent on the conditions as there are also reports that nitroxides can also induce apoptosis. Common media supplements that delay apoptosis are growth factors (insulin-like growth factor, transferrin), amino acids and peptides that specifically inhibit enzymes involved.

Antioxidants have been added to cells in culture to mitigate the deleterious results of radical formation, such as by oxidative stress, for the cells. Among these antioxidants, compounds such as ascorbic acid (see e.g. U.S. Pat. No. 3,703, 439, use in L-DOPA production, not mentioning antioxidative effect) or other antioxidants (see, e.g., U.S. Pat. No. 3,704,205, use of amines or phenols (including BTH or aminophenols) in the manufacture of L-Glutamic acid in aerobic bacteria cultures; or U.S. Pat. No. 6,521,443, use of phenols or SH-group comprising compounds as antioxidants to protect lactobacilli in culture) have been described.

Also, for example, EP 1 764 415 shows the manufacture of p-hydroxybenzyl alcohol (p-HBA) by host cells in a medium to which, inter alia, antioxidants are listed as possible ingredients to be added, without, however, naming or exemplifying specific antioxidants.

U.S. Pat. No. 3,235,467 mentions certain amides, imides or lactames as activators for the biochemical manufacture of β-carotene, to mention an example where other additives are used to increase production in cell culture systems.

US 2003/0096414 mentions cell culture media allowing to transform cells by introducing nucleic acids. Among possible additives, 2-hydroxypyridine-N-oxide is mentioned as a transferring replacement compound, that is, as iron complex former.

US 2003/0114358 mentions trimethylamine-N-oxide as inhibitor of proteolytic protein degradation by hydrolyses, such as proteases, for isolated products.

US 2005/0100994 mentions the cell free enzymatic production of dietary sterol fatty acid esters in the presence of vitamin E or tea polyphenol as antioxidants.

US 2007/0053871 mentions pharmaceutical formulations of proteins, e.g. antibodies, also allowing the addition If antioxidants as preservatives, naming inter alia trimethylamine-N-oxide.

WO2008/100782 describes a fermentation process for the production of coenzyme Q10L in the presence of cysteine, ascorbic acid, dithiothreitol, glutathione and thyoglycolic acid.

WO2008/047113 discloses ethanol production with addition of radical scavengers to cell culture.

US2008/200548 makes use of N-acetylcysteine amide (Nac Amide) for Treatment of Oxidative Stress associated with infertility.

US 2007/110743 mentions the production of proteins in cell culture in the presence of anti-senescence compounds, such as carnosine or analogues thereof.

US 2007/034198 mentions the sterilisation of proteins in the presence of various antioxidants.

Other references mentions e.g. glutathione, cystein or N-acetylcystein as antioxidants.

Hirudin yield and quality in *P. pastoris* is increased by including 4-10 mM Ascorbic acid into the medium (see Xiao, Appl. Microbiol. Biotechnol. (2006) 72: 837-844).

Sterically Hindered and therefore metastable Nitroxide radicals, such as the 2,2,6,6-Tetramethyl-1-piperidinyloxy radical (TEMPO) and 4-hydroxy-2,2,6,6-tetramethyl-1-piperidinyloxy have already been examined in few single cases as additives to cell culture. US 2004/024025, for example, describes that TEMPO causes increased apoptosis in human cancer cells due to SAPK and p38 MAPK signal pathway modulation, leading to protein phosphorylation. Thus results available are rather disencouraging from adding sterically hindered nitroxyls to cell cultures.

U.S. Pat. No. 5,462,946 mentions the use of various nitroxide compounds as antioxidants capable of protecting cells, tissues, organs and whole organisms against the deleterious effects of harmful oxygen-derived species generated during oxidative stress in pharmaceutical formulations. It does not specifically refer to the use in the manufacture of products in cell culture or by biosynthesis in cell free systems. Among many other possible uses, it is mentioned only that they can be used in stabilizing labile chemical compounds which undergo spontaneous degradation by generating free radicals in media which are already present in the media as such.

US 2008/305055 mentions the use of sterically hindered nitroxyl and certain specific phenol compounds as drugs in the treatment of inflammatory or related conditions in humans.

Bednarska, S., et al. described the use of various antioxidants (e.g. ascorbic acid, cysteine, glutathione, N-acetylcysteine, dithiothreitol, trolox, quercetin, melatonin, TEMPO, phenyl butylnitrone) in the protection of protein thiols of proteins within *Saccharomyces Cerevisiae*.

Other approaches to optimize yield in biosynthetic production processes include:

3. Use of Growth Factors, Cytokines and Other Growth Stimulating Molecules as Additives The use of hormones, other signalling molecules and small molecule growth stimulating compounds is most common in mammalian cell culture as these cells grow in vivo within tissues and communicate with surrounding cells through chemical signals. As the use of calf-serum as a source of growth factors in mammalian culture media is less and less accepted for production purposes there is a tendency to include specific growth factors which are mostly proteins from defined non-animal sources. Examples for growth factors are insulin, insulin-like growth factor or epidermal growth factor. Also used are interleukins, cytokines such as interferon, and transport proteins (e.g. albumin, transferrin). All of the aforementioned substances are proteins. In addition are vitamins, amino acids and lipids are also used. (For a general reference see Wove R A 1993 Media for Cell Culture, Biotechnology, Wiley-VCH, 2nd Ed., Vol 3, p. 141-156)

4. Engineering of Cell Lines that Show Greater Stress Resistance and Longer Lifetime This can be achieved either through random mutagenesis or rational introduction of benefical genes. Examples of genes that add to cellular fitness are those that have antioxidative activity such as superoxide dismutase and catalase and genes that contribute to the synthesis of cellular antioxidants such as glutathione biosynthesis. Cellular lifetime is increased by preventing the cells from entering into programmed cell death, also termed apoptosis. Apoptosis, is a regulated physiological response resulting from a non-lethal stimulus that activates a cellular cascade of events culminating in cell death (Arden 2004 Trends Biotechnol 22: 174-180). Increases in cellular fitness and lifetime has been obtained through either both random mutagenesis and subsequent selection of improved cells or through specific over-expression of genes that confer higher viability and lifetime.

5. Process Optimization to Minimize Detrimental Conditions

Major factors considered in process optimization are (1) to achieve high cell densities, (2) longer lifetime of the producer cells, (3) optimal feeding strategies, (4) optimal supply of gaseous substrates, especially oxygen, and (5) media composition.

SUMMARY OF THE INVENTION

Surprisingly it could now be shown that such compounds are able of enhancing the quality, the quantity of both of such products in biosynthetic manufacturing processes using bacterial cell culture systems.

According to the invention, especially sterically hindered nitroxides, e.g. TEMPO, and related compounds such as the corresponding hydroxylamines sterically hindered amino compounds and/or sterically hindered N-hydrocarbyloxyamines, alone and in combination with other antioxidants or radical scavengers (including but not limited to synthetic phenolic antioxidants, amidic antioxidants or natural antioxidants or radical scavengers such as vitamin C or others, see below), have been found to increase the productivity of protein and other biosynthetic product manufacturing processes and/or the quality of the obtainable (especially obtained) products.

Most likely, although other mechanisms are not intended to be ruled out by this hypothetic mechanism, this improvement is due to the radical scavenging and antioxidative activity of these additives.

This makes it possible to increase the yield or the quality or both of products obtainable by biosynthetic routes and thus e.g. helps to mitigate the risk of lack of manufacturing capacity.

The following table shows the advantages and disadvantages of the known approaches and the advantages of the solution according to the present invention:

| Summary of advantages of new approach over state of the art solution | | |
|---|---|---|
| State of the art technique | Disadvantage of state of the art solution | Advantages of nitroxides, HALS, phenolic antioxidants |
| Natural response to oxidative stress | Insufficient under high stress and high productivity situations | No consumption of cellular energy |
| Natural and other synthetic antioxidants | Some such as Vitamin E are difficult to formulate and unstable Vitamin C is also a pro-oxidant in cells, not only antioxidant | Stability may be higher Easier to formulate Nitroxides are catalytically active (not stochiometrically) |
| Growth factors, cytokines and other growth stimulators | | New approach is probably more general and applies to various cell types |
| Engineering of cell lines for stress resistance and longer lifetime | Time consuming Can be process/product specific | More generic solution to radical/oxidative stress |
| Process optimization to minimize detrimental conditions | Time consuming Process/product specific | Generic approach |

None of the prior art disclosures ever suggested the use of nitroxiles and related compounds alone or in combination with other antioxidants such as specific phenols in biosynthetic methods using cell culture or cell free biosynthesis systems to obtain small and/or large molecular biosynthetic products, that is, in the manufacture of such products.

There is an increasing lack of capacity for sufficient production of biotechnologically manufactured products which in some cases already leads to anticipated bottlenecks, e.g. where eukaryotic cell culture systems are used.

It is thus important to find ways to increase the quality and the quantity or both of products obtained in biosynthetic processes.

DETAILED DESCRIPTION OF THE INVENTION (A) The invention, in a first embodiment, relates to a process or method for the manufacture of products by a biosynthetic process or method (together also called manufacturing process hereinafter) in bacterial cell culture systems, which process comprises adding one or more radical scavenging and/or antioxidative additives selected from the group consisting of sterically hindered nitroxyls, sterically hindered hydroxylamines, sterically hindered hydroxylamine salt compounds, sterically hindered amino compounds and sterically hindered N-hydrocarbyloxyamines (each or together also referred to as obligatory compound(s) hereinafter) without or with addition of one or more other (optional) antioxidants or radical scavengers, such as benzofuranone compounds, nitrones, (preferably sterically hindered) phenol antioxidants natural antioxidants or radical scavengers or coumestanes; to the medium in which the cell culture or cell free biosynthetic system is comprised, and leading part or all of the biosynthetic manufacturing process in the presence of said additive or additives, and preferably further purifying and isolating the desired product, without or especially in the presence of one or more of the obligatory additives and optionally one or more of the other antioxidants or radical scavengers; where the additives may be present in free and/or in salt form; where the purified or isolated product optionally can be further confectioned in a form for sale or use, e.g. a pharmaceutical composition, a nutraceutical, a food additive or supplement, an agricultural product, or the like, e.g. with an appropriate packaging and/or instructions for sale and/or use.

Preferred obligatory additives used in the present invention are one or more selected from the group consisting of
(i) sterically hindered nitroxyl compounds, sterically hindered hydroxylamine compounds, or sterically hindered hydroxylamine salt compounds of any one of the formulae IA, IB or IC

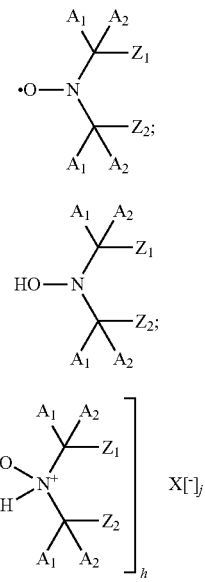

or hindered nitroxyl compounds in the form of an imidazoline nitroxide of the formula ID, IE, IF or IG,

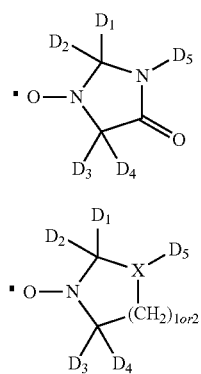

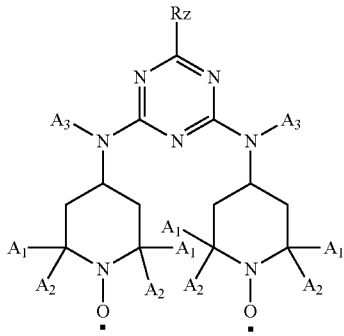

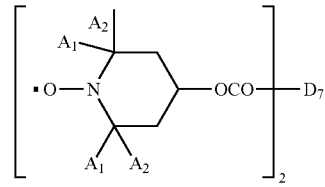

where in the above formulae
X is $CH_2$, O, S or N, with the proviso that $D_5$ is absent if X is O or S;
$A_1$ and $A_2$ are independently alkyl of 1 to 4 carbon atoms or are together $C_3$-$C_8$-alkylene, especially pentamethylene or tetramethylene;
$A_3$ is hydrogen or $C_1$-$C_{12}$alkyl;
Rz is chloro or —N(2-ethylhexyl)$_2$;
$Z_1$ and $Z_2$ are each alkyl of 1 to 4 carbon atoms, e.g. methyl, or
$Z_1$ and $Z_2$ together form a linking moiety which may additionally be substituted by an ester, ether, hydroxy, oxo, cyanohydrin, amide, amino, carboxy or urethane group,
h is the number of positive charges and
j is the number of negative charges,
X is an inorganic or organic anion,
where the total charge of cations h is equal to the total charge of anions j;
$D_1$, $D_2$, D and $D_4$ are each independently selected from the group consisting of unsubstituted or substituted $C_1$-$C_{18}$-alkyl and unsubstituted or substituted $C_6$-$C_{18}$-aryl, or one or more of the geminal pairs $D_1$ and $D_2$ and $D_3$ and $D_4$ can together form a 4-8-membered ring,
$D_5$ is selected from the group consisting of hydrogen, unsubstituted or substituted $C_{10}$-$C_{18}$-alkyl, unsubstituted or substituted $C_6$-$C_{18}$-aryl, acyl, or $D_5$ and any one of $D_1$ together can form a 5-8-membered ring; or X and $D_2$ together can form a 5-8 membered ring;
$D_6$ is hydrogen, $C_1$-$C_{18}$alkyl, $C_5$-$C_{12}$-cycloalkyl, $C_7$-$C_{15}$-arylalkyl or $C_8$-$C_{12}$aryl; and
$D_7$ is alkylene of 2 to 12 carbon atoms;
or the corresponding compounds of the formula IA, ID, IE, IF or IG wherein instead of the
N—O• (nitroxyl) moiety a moiety N-Rk or preferably (in the case of N-hydrocarbyloxyamines)
N—O-Rk is present wherein Rk is $C_1$-$C_{18}$alkyl, unsubstituted or $C_1$-$C_7$-alkyl substituted $C_3$-$C_8$-cycloalkyl, mono- or di-(phenyl and/or naphthyl)-$C_1$-$C_{18}$alkyl, norbornyl, naphthyl, phenyl or decahydronaphthyl or especially $C_1$-$C_{18}$alkyloxy, $C_1$-$C_7$-alkyl substituted $C_3$-$C_8$-cycloalkyloxy, mono- or di-(phenyl and/or naphthyl)-$C_1$-$C_{18}$alkyloxy, norbornyloxy, naphthyloxy, phenyloxy or decahydronahphthyloxy, where phenyl or naphthyl are unsubstituted or substituted preferably by one or more moieties independently selected from hydroxy, halo, methanesulfonyl, carboxy, carbamoyl, aminosulfonyl, sulfuryl, amino, mono- or di-$C_1$-$C_7$-alkylamino and cyano; and (ii) sterically hindered amino compounds, preferably a compound of the formula IA*, ID*, IE*,

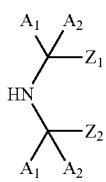

IA* or hindered amino compounds in the form of an imidazoline or other heterocyclic compound of the formula ID, IE, IF or IG,

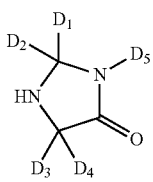

ID*

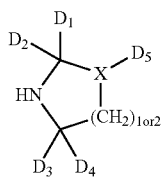

IE*

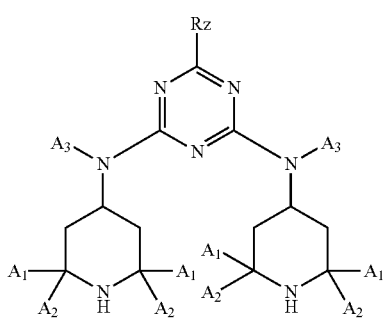

IF*

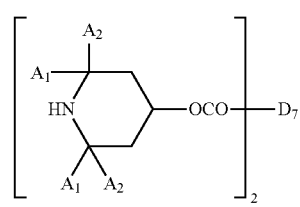

IG* wherein the symbols $A_1$, $A_2$, $A_3$, $D_1$, $D_2$, $D_3$, $D_4$, $D_5$, $Z_1$, $Z_2$ and Rz are as defined under (i) for the compounds mentioned there;

preferably compounds of any one of the formulae IIA or IIB,

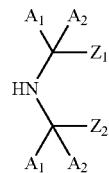

IIA

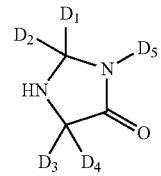

IIB wherein $A_1$, $A_2$, $Z_1$, $Z_2$, X and $D_1$ to $D_5$ are as defined above under (i);

where the additives may be present in free and/or in salt form.

A particularly preferred group of obligatory additives are compounds selected from sterically hindered nitroxyles and especially sterically hindered hydroxylamines and sterically hindered N-hydrocarbyloxyamines, especially of formulae IO, IP, IM, IN:

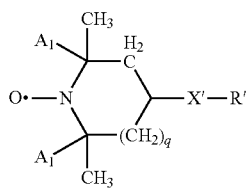

IO

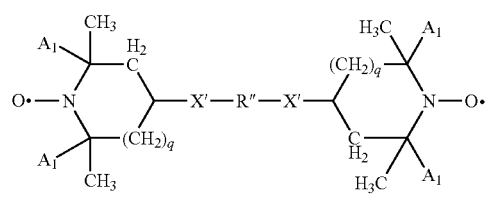

IP

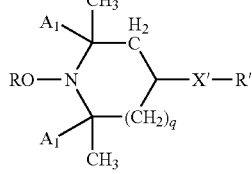

IM

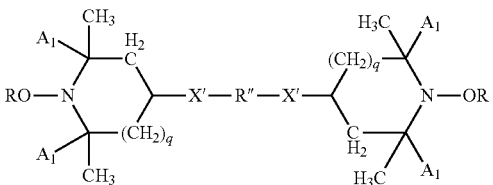

IN wherein q is 0 or 1, especially 1;
$A_1$ is methyl or ethyl;
R is H or hydrocarbyl, especially H or unsubstituted or substituted $C_1$-$C_8$hydrocarbyl such as $C_1$-$C_8$alkyl or $C_2$-$C_8$hydroxyalkyl;

X' is O or NH or a direct bond;

R' is as defined for R or is CO—R or CO—R'''-COOH or a suitable salt thereof such as an alkaline salt CO—R'''-COOMe with Me standing for ammonium or alkaline;

R'' is $C_1$-$C_{12}$alkylene, or $C_3$-$C_{12}$alkylene substituted by OH, COOH, COOMe with Me being ammonium or an alkaline atom, or is CO—R'''-CO;

R''' is a direct bond, $C_1$-$C_{12}$alkylene, or is $C_3$-$C_{12}$alkylene substituted by OH, COOH, COOMe with Me as defined above.

Most especially preferred are sterically hindered hydroxylamines such as those of the above formulae IM and IN wherein R is hydrogen.

One or more of these may be used alone as additives according to the invention, or in combination with one or more other (optional) antioxidants or radical scavengers especially selected from the group including but not limited to, preferably consisting of:

(α) benzofuranone compounds, especially of the formula III

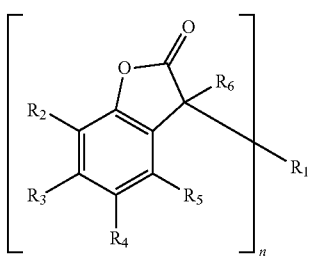

III wherein when n is 1, $R_1$ is an unsubstituted or substituted substituents: especially $C_1$-$C_{22}$alkyl; $C_1$-$C_{22}$alkylthio; $C_2$-$C_{22}$alkylthioalkyl; $C_5$-$C_7$cycloalkyl; phenyl; $C_7$-$C_9$-phenylalkyl; or $SO_3M$; carbocyclic or heterocyclic aromatic ring system and when n is 2, $R_1$ is unsubstituted or $C_1$-$C_4$alkyl- or hydroxy-substituted phenylene or naphthylene; or is —$R_6$—X—$R_7$—, $R_2$, $R_3$, $R_4$ and $R_5$ are each independently of one another hydrogen, halo, especially chloro, hydroxy, $C_1$-$C_{25}$ alkyl, $C_7$-$C_9$-phenylalkyl, unsubstituted or $C_1$-$C_4$alkyl-substituted phenyl, unsubstituted or $C_1$-$C_4$alkyl-substituted $C_5$-$C_8$cycloalkyl; $C_1$-$C_{18}$alkoxy, $C_1$-$C_{18}$alkylthio, $C_1$-$C_4$alkylamino, di-($C_1$-$C_4$ alkyl)amino, $C_1$-$C_{25}$alkanoyloxy, $C_1$-$C_{25}$alkanoylamino, $C_3$-$C_{25}$ alkenoyloxy, $C_3$-$C_{25}$ alkanoyloxy which is interrupted by oxygen, sulfur or >N—$R_8$; $C_6$-$C_9$cycloalkylcarbonyloxy, benzoyloxy or $C_1$-$C_{12}$ alkyl-substituted benzoyloxy; or each pair of substituents $R_2$ and $R_3$ or $R_3$ and $R_4$ or $R_4$ and $R_5$, together with the linking carbon atoms, forms a benzene ring; or $R_4$ can additionally be —$(CH_2)_p$—$COR_S$ or —$(CH_2)_c$, OH, or, if $R_3$ and $R_5$ are hydrogen, $R_4$ can additionally be a radical of formula A,

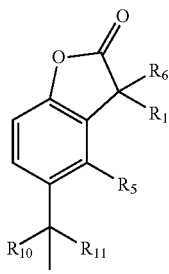

wherein $R_1$ is as defined above when n=1, $R_6$ and $R_7$ are each independently of the other unsubstituted or $C_1$-$C_4$ alkyl-substituted phenylene or naphthylene, $R_8$ is hydrogen or $C_1$-$C_8$alkyl, $R_9$ is hydroxy, (—$O^-$ 1/r $M^{r+}$). $C_1$-$C_{18}$alkoxy or —$N(R_{12})(R_{13})$, $R_{10}$ and $R_{11}$ are each independently of the other hydrogen, $CF_3$, $C_1$-$C_{12}$ alkyl or phenyl, or $R_{10}$ and $R_{11}$, together with the linking carbon atom, form a $C_5$-$C_8$ cycloalkylidene ring which is unsubstituted or substituted by 1 to 3 $C_1$-$C_4$ alkyl groups, $R_{14}$ is hydrogen or $C_1$-$C_{18}$alkyl, M is a metal cation of valency r, X is a direct bond, oxygen, sulfur or $NR_{14}$, n is 1 or 2, p is 0, 1 or 2, q is 1, 2, 3, 4, 5 or 6, and r is 1, 2 or 3;

(β) nitrones of any one of the formulae IVA and IVB,

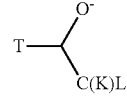

IVA

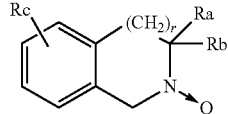

IVB wherein

T is $C_1$-$C_{18}$alkyl,

K is hydrogen, methyl or ethyl,

L is $C_1$-$C_{17}$alkyl, where preferably the sum of the carbon atoms in K and L is 7 to 17, Ra and Rb are independently selected from $C_1$-$C_3$alkyl or together form a $C_2$-$C_7$alkylene chain;

r is an integer from 0 to 2; and

Rc is a substitutent selected from the group consisting of hydrogen, halogen, $C_1$-$C_4$alkyl, $C_1$-$C_4$alkoxy, $CF_3$, $OCF_3$ and —OH;

(γ) especially sterically hindered, phenol compounds, preferably compounds of any one of the formula V and especially VI,

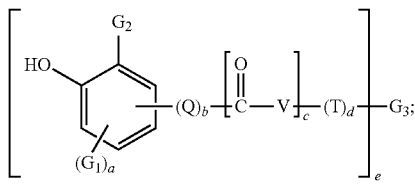

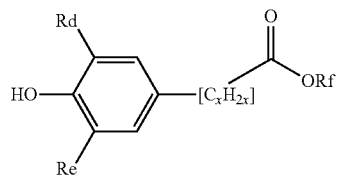

wherein $G_1$ is hydrogen; $C_1$-$C_{22}$alkyl; $C_2$-$C_{22}$alkylthio; $C_2$-$C_{22}$alkylthioalkyl; $C_5$-$C_7$cycloalkyl; phenyl; $C_7$-$C_9$-phenylalkyl; or $SO_3M$;

$G_2$ is $C_1$-$C_{22}$alkyl; $C_5$-$C_7$cycloalkyl; phenyl; or $C_7$-$C_9$-phenylalkyl;

Q is $-C_mH_{2m}-$;

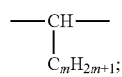

$-C_mH_{2m}-NH$; a radical of formula

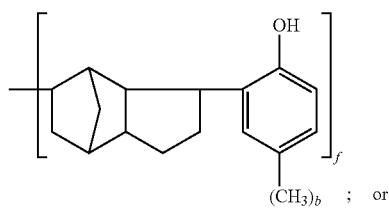

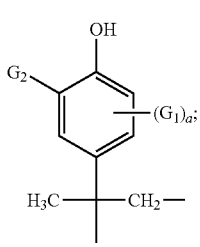

T is $-C_mH_{2m}-$; $-(CH_2)_m-O-CH_2-$; phenylene;

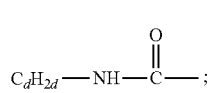

or a radical of formula

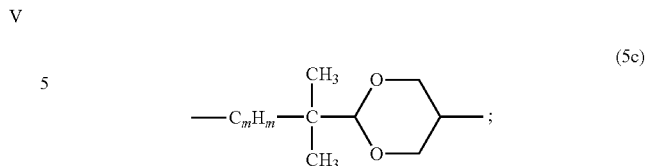

V is $-O-$; or $-NH-$;

a is 0; 1; or 2;

b, c and d are each independently of one another 0; or 1;

e is an integer from 1 to 4;

f is an integer from 1 to 3; and m and p are each independently of the other integer from 1 to 3;

q is 0 or an integer from 1 to 3;

if e=1, then $G_3$ is hydrogen; $C_1$-$C_{22}$alkyl; $C_5$-$C_7$cycloalkyl; $C_1$-$C_{22}$alkylthio; $C_2$-$C_{22}$alkylthioalkyl; $C_2$-$C_{18}$alkenyl; $C_1$-$C_{18}$phenylalkyl; M; $SO_3M$; a radical of formula

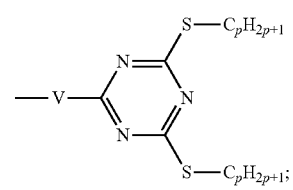

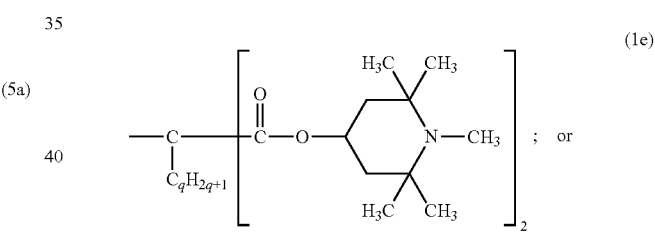

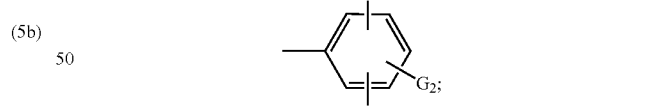

or $G_3$ is propyl substituted by OH and/or by $C_2$-$C_{22}$alkanoyloxy;

M is alkali; ammonium; H;

if e=2, then $G_3$ is a direct bond; $-CH_2-$;

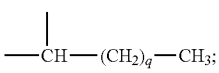

or $-S-$; or $G_3$ is propyl substituted by OH or $C_2$-$C_{22}$alkanoyloxy;

if
e=3, then
G₃ is the radical of formula

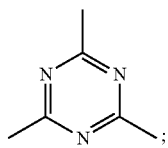 (1g)

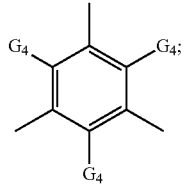 (1h)

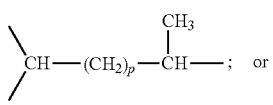 or (1i)

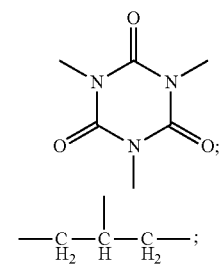 (1k)

if
e=4, then
G₃ is

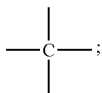

G₄ and G₅ are each independently of the other hydrogen; or C₁-C₂₂alkyl one of Rd and Re otherwise independently of one another represents hydrogen or C₁-C₄alkyl and the other represents C₃-C₄-alkyl;

x represents zero (direct bond) or an ineger from 1 to 3; and

Rf represents C₈-C₂₂alkyl; or a group of the formula 6A or 6B,

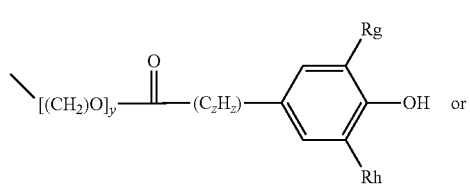 or 6A

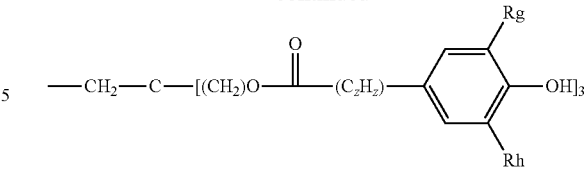

wherein one of Rg and Rh otherwise independently of one another represents hydrogen or C₁-C₄alkyl and the other one represents C₃-C₄alkyl;

y represents an integer from 2 to 6; and z represents zero (direct bond) or an integer from 1 to 3;

(δ) natural antioxidants and/or radical scavengers (including the corresponding chemically made analogs), e.g. selected from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, natural antioxidants and/or radical scavengers (including the corresponding chemically made analogs), e.g. selected from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, N-acetylcycleine, cystamine and the glycosyl, N-acetyl, methyl, ethyl, propyl, amyl, butyl, lauryl, palmitoyl, oleyl, linoleyl, cholesteryl and glyceryl derivatives thereof) and also salts thereof, dilauryl thiodipropionate, distear[gamma]l thiodipropionate, thiodi-propionic acid and derivatives thereof (e.g. esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin, chitosan and derivatives such as phosphonomethylated chitosan) and preferably those disclosed in the following disclosures (which regarding their generic or especially specific compound disclosure are incorporated by reference herein) U.S. Pat. No. 5,487,884; WO91/16035; WO91/16034; hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl) propionyl]sulfanilic acid (and salts thereof, for example the disodium salts), zinc and derivatives thereof (e.g. ZnO, ZnSO4), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredientscystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distear[gamma]l thio-dipropionate, thiodi-propionic acid and derivatives thereof (e.g. esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin, chitosan and derivatives such as phosphonomethylated chitosan) and preferably those disclosed in the following disclosures (which regarding their generic or especially specific compound disclosure are incorporated by reference herein) U.S. Pat. No. 5,487,884; WO91/16035; WO91/16034; hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosyl-rutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl] sulfanilic acid (and salts thereof, for example the disodium salts), zinc and derivatives thereof (e.g. ZnO, ZnSO4), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients; and (ε) coumestanes, especially as disclosed in WO 2008/110465 which is (preferably with regard to the passage starting on page 2, line 5 to the end on page 4, 4$^{Th}$ paragraph; more preferably the passage starting on page 4, last paragraph to the end on page 6, line 1; e.g. the passage consisting of page 6, 2$^{nd}$ paragraph; especially the passage starting on page 6 to the end on page 8, line 17; and very especially with regard to the single compounds mentioned from page 15, last paragraph, to page 19, compound B-4, e.g. the compounds mentioned in the Examples), such as those selected from the group consisting of:

compounds of general formula (I)

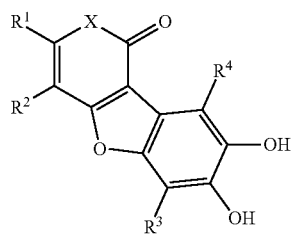

wherein

X is O, NH or $NR^{15}$, $R^1$, $R^2$, $R^3$ and $R^4$ are independently of each other H, halogen, especially fluorine, hydroxy, $C_1$-$C_{24}$alkyl, $C_1$-$C_{24}$alkyl which is substituted by at least one E and/or interrupted by at least one D, $C_1$-$C_{24}$ perfluoroalkyl, $C_6$-$C_{14}$perfluoroaryl, especially pentafluorophenyl, $C_5$-$C_{12}$cycloalkyl, $C_5$-$C_{12}$cycloalkyl which is substituted by G and/or interrupted by S—, —O—, or —$NR^{15}$—, —$NR^{15}R^{16}$, $C_1$-$C_{24}$alkylthio, —$PR^{17}R^{18}$, $C_5$-$C_{12}$cycloalkoxy, $C_5$-$C_{12}$cycloalkoxy which is substituted by G, $C_6$-$C_{24}$aryl, $C_6$-$C_{24}$aryl which is substituted by G, $C_1$-$C_{24}$alkyl, $C_5$-$C_{12}$cycloalkyl, $C_7$-$C_{25}$aralkyl, $C_1$-$C_{24}$ perfluoroalkyl, $C_6$-$C_{14}$ perfluoroaryl, especially pentafluorophenyl, or $C_1$-$C_{24}$haloalkyl; $C_2$-$C_{20}$heteroaryl, $C_2$-$C_{20}$heteroaryl which is substituted by G, fluorine, $C_1$-$C_{24}$alkyl, $C_5$-$C_{12}$cycloalkyl, $C_7$-$C_{25}$aralkyl, $C_1$-$C_{24}$ perfluoroalkyl, $C_6$-$C_{14}$perfluoroaryl, especially pentafluorophenyl, or $C_1$-$C_{24}$haloalkyl; $C_2$-$C_{24}$alkenyl, $C_2$-$C_{24}$alkynyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by G, $C_7$-$C_{25}$aralkoxy, $C_7$-$C_{25}$aralkoxy which is substituted by G, or —CO—$R^{19}$, or $R^1$ and $R^2$ are a group

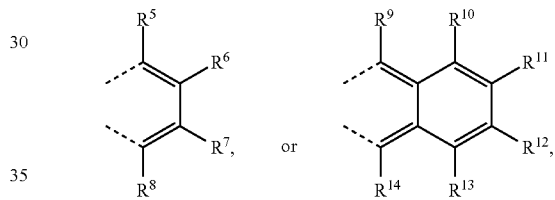

wherein $R^5$, $R^6$, $R^7$, $R^8$, $R^9$, $R^{10}$, $R^{11}$, $R^{12}$, $R^{13}$ and $R^{14}$ are independently of each other H, halogen, hydroxy, $C_1$-$C_{24}$alkyl, $C_1$-$C_{24}$alkyl which is substituted by at least one E and/or interrupted by at least one D, $C_1$-$C_{24}$ perfluoroalkyl, $C_6$-$C_{14}$ perfluoroaryl, especially pentafluorophenyl, $C_5$-$C_{12}$cycloalkyl, $C_5$-$C_{12}$cycloalkyl which is substituted by at least one G and/or interrupted by at least one S—, —O—, or —$NR^{15}$—, $C_5$-$C_{12}$cycloalkoxy, $C_5$-$C_{12}$cycloalkoxy which is substituted by G, $C_6$-$C_{24}$aryl, $C_6$-$C_{24}$aryl which is substituted by at least one G, $C_2$-$C_{20}$heteroaryl, $C_2$-$C_{20}$heteroaryl which is substituted by at least one G, $C_2$-$C_{24}$alkenyl, $C_2$-$C_{24}$alkynyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by at least one G, $C_7$-$C_{25}$aralkoxy, $C_7$-$C_{25}$aralkoxy which is substituted by at least one G, or at least —CO—$R^{19}$, D is —CO—; —COO—; —S—; —SO—; —$SO_2$—; —O—; —$NR^{15}$—; —$POR^{17}$—; —$CR^{20}$═$CR^{21}$—; or —C≡C—;

E is —$OR^{22}$; —$SR^{22}$; —$NR^{15}R^{16}$; —[$NR^{15}R^{16}R^{24}$]$^+Z^-$; —$COR^{19}$; —$COOR^{23}$; —$CONR^{15}R^{16}$; —CN; —$N_3$; —$OCOOR^{23}$; or halogen; and G is E, or $C_1$-$C_{24}$alkyl, wherein $R^{20}$, $R^{21}$, $R^{15}$, $R^{16}$ and $R^{24}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—; or $R^{15}$ and $R^{16}$ together form a five or six membered ring, in particular

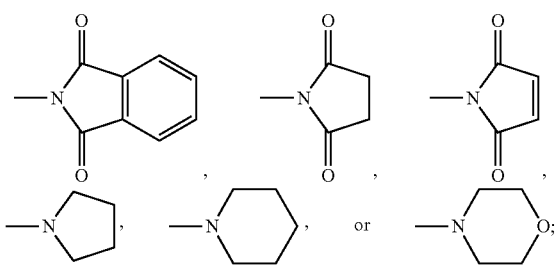

Z is halogen, preferably Cl;

$R^{19}$ and $R^{23}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—;

$R^{22}$ is H; $C_6$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—; and $R^{17}$ and $R^{18}$ are independently of each other $C_1$-$C_{24}$alkyl, $C_6$-$C_{18}$aryl, or $C_6$-$C_{18}$aryl, which is substituted by $C_1$-$C_{24}$alkyl;

$R^3$ and $R^4$ may further be a mono-, di- or oligosaccharide residue alpha- or beta-linked to the phenolic ring system either directly or via the phenolic oxygen;

where the compound(s) under α, β, γ, δ and/or δ may be used in the free form or in salt form.

(B) In a second embodiment, the invention relates to the products obtainable, especially obtained, in the process as described in the preceding paragraph.

(C) In yet another embodiment, the invention relates to the use of one or more of the additives mentioned in paragraph (A) to enhance the quantity and/or the quality of the product obtainable in a biosynthetic process of manufacture, said use comprising adding into, and/or using one or more of said additives within, a medium in which a cell culture or a cell free biosynthetic system is comprised, especially in a cell culture medium.

(D) In a fourth embodiment, the invention relates to a method of use, or the use, of said additives in reducing the detrimental effects of radicals in the manufacture of the products, as well as aspects related to these invention embodiments.

(E) In a fifth embodiment, the invention relates to a cell culture or cell free preparation in liquid or solid form that comprises one or more radical scavenging and/or antioxidative additives selected from the group consisting of sterically hindered nitroxyls, sterically hindered hydroxylamines, sterically hindered hydroxylamine salt compounds, sterically hindered amino compounds and sterically hindered N-hydrocarbyloxyamines (each also referred to as obligatory compound(s) hereinafter) without or with addition of one or more other (optional) antioxidants or radical scavengers, such as benzofuranone compounds, nitrones, (preferably sterically hindered) phenol antioxidants natural antioxidants or radical scavengers or coumestanes; or a mixture of two or more of these additives; where the additives may be present in free and/or in salt form. Said cell culture or cell free preparation may preferably be in the form of a dispersion, especially a suspension, or a solution, respectively, and may comprise other ingredients to complete the media required for cell culture or cell free processes according to (A) above or its preferred variants. The preparations may be solid, e.g. after drying by evaporation or preferably lyophilisation, or wet, e.g. in the case of cell pellets obtained by centrifugation, or they may be in the form of the complete medium including cells or the cell free biosynthetic components, respectively.

(F) In a sixth embodiment, the invention relates to a medium for cell culture, or a main component of a cell culture medium, e.g. the carbon source and/or the energy source or in case of a complex medium the extract, e.g. a fungal extract, such as yeast extract, or a bacterial extract, comprising one or more radical scavenging and/or antioxidative additives selected from the group consisting of sterically hindered nitroxyls, sterically hindered hydroxylamines, sterically hindered hydroxylamine salt compounds, sterically hindered amino compounds and sterically hindered N-hydrocarbyloxyamines (each also referred to as obligatory compound(s) hereinafter), especially as described herein as example or preferred, without or with addition of one or more other antioxidants or radical scavengers, such as benzofuranone compounds, nitrones, (preferably sterically hindered) phenol antioxidants natural antioxidants or radical scavengers or coumestanes; or a mixture of two or more of these additives, especially as defined as preferred or example herein; where the additives may be present in free and/or in salt form. This means especially the corresponding medium, or main component, in dry form.

The general terms used hereinbefore and hereinafter preferably have within the context of this disclosure the following meaning, unless otherwise indicated—any one or more of the more general expression used herein, especially in the claims, can, independently of other terms, be replaced with a more specific definition provided below, thus defining a preferred embodiment of the invention:

Throughout the description and claims of this specification, the words "comprise" and "include" and variations of the words, for example "comprising" and "comprises", usually mean "including but not limited to", and are not intended to (and do not) exclude other moieties, additives, components, integers or steps, in contrast to "contain" and variations thereof, such as "contains" or "containing", which mean that the components or features to which this word is attributed are limited to those mentioned. Where "comprises" or "comprising" is used, where appropriate and reasonable, this can be replaced by "consists of" or "consisting of" which leads to preferred invention embodiments.

$Z_1$ and $Z_2$ are each alkyl of 1 to 4 carbon atoms, e.g. methyl, or $Z_1$ and $Z_2$ together form a A linking moiety formed from $Z_1$ and $Z_2$ is preferably $C_1$-$C_{10}$alkylene, such as $C_2$-$C_5$-alkylene, more preferably ethylene, trimethylene or tetramethylene. Whereever mentioned, alkyl preferably comprises 1 to 20, more preferably 1 to 12, and especially 1 to 8 carbon atoms, including, within the limits defined, for example methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl.

Hydrocarbyl, whereever mentioned, generally stands for a $C_1$-$C_{20}$ hydrocarbon residue, which is unsubstituted or substituted, and preferably comprises alkyl as defined above, $C_3$-$C_8$cycloalkyl (especially cyclohexyl), or alkyl substituted by phenyl or cyclohexyl. Substituents to these hydrocarbon residues, if present, are preferably OH or COOH or suitable salts of COOH such as alkaline.

An ester substituent is preferably $C_1$-$C_{18}$-alkoxycarbonyl, phenyl- or napthyl-$C_1$-$C_6$-alkoxycarbonyl, phenyloxycarbonyl or naphthyloxycarbonyl, where phenyl or naphthyl where mentioned are unsubstituted or substituted by one or more substituents preferably independently selected from the group consisting of hydroxy, halo, carboxy, carbamoyl, aminosulfonyl, sulfuryl, $C_1$-$C_7$-alkoxy, $C_1$-$C_7$-alkane-sulfonyloxy, amino or mono- or di-($C_1$-$C_7$-alkyl)amino.

An ether substituent is preferably $C_1$-$C_{18}$-alkoxy, phenyl- or napthyl-$C_1$-$C_6$-alkoxy, phenyloxy or naphthyloxy, where phenyl or naphthyl where mentioned are unsubstituted or substituted by one or more substituents preferably independently selected from the group consisting of hydroxy, halo, carboxy, carbamoyl, aminosulfonyl, sulfuryl, $C_1$-$C_7$-alkoxy, $C_1$-$C_7$-alkane-sulfonyloxy, amino or mono- or di-($C_1$-$C_7$-alkyl)amino.

Cyanohydrin is CN.

An amide substituent is preferably $C_1$-$C_{18}$-alkylaminocarbonyl, N-mono- or N,N-di-($C_1$-$C_{10}$-alkyl, phenyl-$C_1$-$C_6$-alkyl or napthyl-$C_1$-$C_6$-alkyl)aminocarbonyl, phenylaminocarbonyl or naphthylaminocarbonyl, where phenyl or naphthyl where mentioned are unsubstituted or substituted by one or more substituents preferably independently selected from the group consisting of hydroxy, halo, carboxy, carbamoyl, aminosulfonyl, sulfuryl, $C_1$-$C_7$-alkoxy, $C_1$-$C_7$-alkanesulfonyloxy, amino or mono- or di-($C_1$-$C_7$-alkyl)amino.

A urethane group is preferably unsubstituted or mono- or disubstituted amino-carbonyloxy, where the substituents are selected from $C_1$-$C_7$alkyl, $C_1$-$C_7$-alkanoyl, benzenecarbonyl, naphthenecarbonyl, $C_1$-$C_7$-alkanesulfonyl, phenyl-$C_1$-$C_7$-alkyl and naphthyl-$C_1$-$C_7$-alkyl, where each of phenyl and naphthyl (including "benzene" and "naphthene") is unsubstituted or substituted by one or more substituents preferably independently selected from the group consisting of hydroxy, halo, carboxy, carbamoyl, aminosulfonyl, sulfuryl, $C_1$-$C_7$-alkoxy, $C_1$-$C_7$-alkane-sulfonyloxy, amino or mono- or di-($C_1$-$C_7$-alkyl)amino.

An inorganic or organic anion is preferably phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate.

Aryl where mentioned (also where numbers are given for the ring atoms, e.g. in $C_6$-$C_{18}$aryl, preferably has 6 to 14 ring carbon atoms and can be mono-, di- or tricyclic, e.g. phenyl, naphthyl or fluorenyl, and can be unsubstituted or substituted by one or more substituents preferably independently selected from the group consisting of $C_1$-$C_7$-alkyl, hydroxy, halo, carboxy, carbamoyl, aminosulfonyl, sulfuryl, $C_1$-$C_7$-alkoxy, $C_1$-$C_7$alkane-sulfonyloxy, amino or mono- or di-($C_1$-$C_7$-alkyl)amino.

Where "one or more" is mentioned regarding substituents, this preferably means 1 to 4, e.g. 1 to 3, for example 1 or 2 substituents, if not otherwise defined.

Where geminal pairs $D_1$ and $D_2$ or $D_3$ and $D_4$ or X and $D_2$ or $D_5$ and $D_1$ can together form a 4-8-membered ring, said ring can be a can be carbocyclic (which is preferred) or may comprise, instead of the corresponding number of carbon atoms, 1 or 2 heteroatoms independently selected from O, S or N.

Acyl is preferably the acyl moiety of an organic carbonic or an organic sulfonic acid, e.g. $C_1$-$C_{10}$-alkanoyl, phenyl- or naphthyl-$C_1$-$C_7$-alkanoyl, $C_1$-$C_{10}$-alkanesulfonyl, phenyl- or naphthyl-$C_1$-$C_7$-alkanesulfonyl, where alkanoyl, phenyl or naphthyl are unsubstituted or substituted by one or more substituents preferably independently selected from the group consisting of hydroxy, halo, carboxy, carbamoyl, aminosulfonyl, sulfuryl, $C_1$-$C_7$-alkoxy, $C_1$-$C_7$-alkane-sulfonyloxy, amino or mono- or di-($C_1$-$C_7$-alkyl)amino.

Halo (also as "halogen") is preferably fluoro, chloro, bromo or iodo, especially fluoro, chloro or bromo.

Among the suubstituents of $R_1$, especially $C_1$-$C_{22}$alkyl; $C_1$-$C_{22}$alkylthio; $C_2$-$C_{22}$alkylthioalkyl; $C_5$-$C_7$cycloalkyl; phenyl; $C_7$-$C_9$-phenylalkyl; or $SO_3M$ are to be mentioned, or one or more substituents preferably independently selected from the group consisting of hydroxy, halo, carboxy, carbamoyl, aminosulfonyl, sulfuryl, $C_1$-$C_7$-alkoxy, $C_1$-$C_7$-alkane-sulfonyloxy, amino or mono- or di-($C_1$-$C_7$-alkyl)amino.

A carbocyclic or heterocyclic aromatic ring system can be any saturated, unsaturated or partially saturated mono-, di- or polycyclic ring system.

Preferred carbocyclic ring systems are based on a benzene ring, or on a system of fused benzene rings, typically of 2 to 5, preferably 2 or 3, rings, one or more of which rings may be wholly or partially hydrogenated. It is preferred and for some embodiments of the invention essential that the linkage is through an aromatic ring.

Heterocyclic rings, which may themselves be aromatic or nonaromatic, may also be fused to the benzene ring or the fused benzene rings, preferably those containing 5 or 6 ring members, typically 1 to 3 hetero atoms selected from the group consisting of nitrogen, oxygen and sulfur.

Preferred heterocyclic aromatic ring systems are preferably 5- or 6-membered heterocyclic rings having aromaticity, which contain 1 to 3, preferably 1 or 2, hetero atoms selected from the group consisting of nitrogen, oxygen and sulfur. To these rings may be fused further carbocyclic or heterocyclic aromatic or non-aromatic rings, carbocyclic 6-membered, preferably aromatic, rings being preferred.

The carbocyclic of heterocyclic aromatic ring systems, as well as the heterocyclic rings, may be unsubstituted or substituted by one or more substituents preferably independently selected from the group consisting of hydroxy, halo, carboxy, carbamoyl, aminosulfonyl, sulfuryl, C1-C7-alkoxy, C1-C7-alkane-sulfonyloxy, amino or mono- or di-(C1-C7-alkyl)amino.

A metal cation can be of any type that is not toxic or otherwise detrimental in the system used; examples are mono-, di- or trivalent metal cations, preferably an alkali metal cation, an alkaline earth metal cation or an aluminium cation, typically $Na^+$, $K^+$, $Mg^{2+}$+, $Ca^{2+}$+ or $Al^{3+}$, or $Zn^{2+}$ or $Cu^{2+}$.

The sterically hindered nitroxyls, sterically hindered hydroxylamines and sterically hindered hydroxylamine salt compounds may preferably be selected from the preferred genera or especially the specific compounds disclosed in U.S. Pat. Nos. 7,390,904, 6,825,384 and US 2008/0305055, as well the sterically hindered amino compounds which can be manufactured therefrom by reduction, e.g. with appropriate reductants such as hydrogen in combination with palladium, platinum, ruthenium, iridium catalysts, sodium borohydride, sodium cyanoborohydride, lithiumaluminum hydride, ascorbic acid, sodium sulfite, sodium thiosulfate, hypophosphoric acids or salts thereof, Red-Al, Dibal-H, combination of an acid (e.g. hydrochloric acid, acetic acid) with metals (such as zinc, magnesium) or tin (II)-chloride., benzofuranone compounds e.g. from those disclosed in U.S. Pat. Nos. 5,607,624, 5,607,624, US 2003/0212170 and US 2008/0305055, nitrones e.g. from those disclosed in U.S. Pat. No. 4,898,901 and U.S. Pat. No. 5,677,315 and (preferably sterically hindered) phenol antioxidants e.g. from those disclosed in U.S. Pat. No. 7,323,505, WO00/32687 and US 2008/0305055.

Note the sterically hindered amino compounds may be oxidized under the manufacturing conditions to the corresponding nitroxyls, so that this may be an explanation for their radical scavenging and antioxidant efficiency. Also a change from nitroxyls, sterically hindered hydroxylamines and hydrocarbyloxyamines can be changed to each other under the conditions in a cell culture or cell free manufacture, so that they are to a certain extent mutually interchangeable.

The mentioned reference documents, without that this means that they are acknowledged as relevant prior art, are herewith enclosed by reference especially regarding there disclosure of the compounds mentioned and their manufacture.

Especially preferred are the following additives:

As sterically hindered nitroxyls, sterically hindered hydroxylamines and sterically hindered hydroxylamine salt compounds, among the preferred ones are those selected from the group consisting of Bis(1-cyclohexyloxy-2,2,6,6-tetramethylpiperidin-4-yl) sebacate; 1-Cyclohexyl-oxy-4-methoxy-2,2,6,6-tetramethylpiperidine; Bis(1-heptyloxy-2,2,6,6-tetramethylpiperidin-4-yl) sebacate; 1-Hexyloxy-4-methoxy-2,2,6,6-tetramethylpiperidine; Bis[1-(2-methyl-2-phenyl-propyloxy)-2,2,6,6-tetramethylpiperidin-4-yl] adipate; 1-(2-methyl-2-phenylpropyloxy)-4-benzoyloxy-2,2,6,6-tetramethylpiperidine; 2-Chloro-4,6-bis[N-(1-cyclohexyloxy-2,2,6,6-tetramethylpiperidin-4-yl) butylamino]-s-triazine; 2,4,6-Tris[N-(1-cyclohexyloxy-2,2,6,6-tetramethylpiperidin-4-yl)butylamino]-s-triazine; Bis(1-octyloxy-2,2,6,6-tetramethylpiperidin-4-yl) sebacate; 1-Cyclooctyloxy-2,2,6,6-tetramethylpiperidin-4-ol; the reaction product of bis(1-oxyl-2,2,6,6-tetramethylpiperidin-4-yl) sebacate and methylcyclohexane; the reaction product of bis(1-oxyl-2,2,6,6-tetramethylpiperidin-4-yl) succinate and norbornane; the reaction product of 1-oxyl-2,2,6,6-tetramethylpiperidin-4-ol and decahydronaphthalene; the reaction product of bis(1-oxyl-2,2,6,6-tetramethylpiperidin-4-yl) adipate and isooctane; the reaction product of 1-oxyl-4-benzoyloxy-2,2,6,6-tetramethylpiperidine and isooctane; Bis[1-(2,2-diphenylpropyloxy)-2,2,6,6-tetramethylpiperidin-4-yl] sebacate; 1-Cyclohexyloxy-2,2,6,6-tetramethylpiperidine; Bis(1-octadecyloxy-2,2,6,6-tetramethylpiperidin-4-yl) succinate; 1-Cyclohexyloxy-4-octadecanoyloxy-2,2,6,6-tetramethylpiperidine; 1-Octyloxy-4-benzoyloxy-2,2,6,6-tetramethylpiperidine; 1-Cyclohexyloxy-4-benzoyloxy-2,2,6,6-tetramethylpiperidine; 1-Cyclohexyloxy-2,2,6,6-tetramethylpiperidin-4-ol; 1-Cyclohexyloxy-2,2,6,6-tetramethylpiperidin-4-one; bis(1-oxyl-2,2-6-6-tetramethylpiperidin-4-yl) sebacate; bis(1-hydroxy-2,2-6-6-tetramethylpiperidin-4-yl) sebacate; 1-hydroxy-2,2-6-6-tetramethyl-4-acetoxypiperidinium citrate; 1-oxyl-2,2,6,6-tetramethyl-4-acetamidopiperidine; 1-hydroxy-2,2,6,6-tetramethyl-4-acetamidopiperidine; 1-hydroxy-2,2,6,6-tetramethyl-4-acetamidopiperidinium bisulfate; 1-oxyl-2,2,6,6-tetramethyl-4-oxo-piperidine; 1-hydroxy-2,2,6,6-tetramethyl-4-oxo-piperidine; 1-hydroxy-2,2,6,6-tetramethyl-4-oxo-piperidinium acetate; 1-oxyl-2,2,6,6-tetramethyl-4-methoxy-piperidine; 1-hydroxy-2,2,6,6-tetramethyl-4-methoxy-piperidine; 1-hydroxyl-2,2,6,6-tetramethyl-4-methoxy-piperidinium acetate; 1-oxyl-2,2,6,6-tetramethyl-4-acetoxypiperidine; 1-hydroxy-2,2,6,6-tetramethyl-4-acetoxypiperidine; 1-oxyl-2,2,6,6-tetramethyl-4-propoxy-piperidine; 1-hydroxy-2,2,6,6-tetramethyl-4-propoxy-piperidinium acetate; 1-hydroxy-2,2,6,6-tetramethyl-4-propoxy-piperidine; 1-oxyl-2,2,6,6-tetramethyl-4-(2-hydroxy-4-oxapentoxy)piperidine; 1-hydroxy-2,2,6,6-tetramethyl-4-(2-hydroxy-4-oxapentoxy) piperidinium acetate; 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; tetra(1-hydroxy-2,2,6,6-tetramethyl-4-hydroxypiperidinium) ethylenediaminetetraacetate; tetra(1-hydroxy-2,2,6,6-tetramethyl-4-acetamidopiperidinium) ethylenediaminetetraacetate; tetra(1-hydroxy-2,2,6,6-tetramethyl-4-oxopiperidinium) ethylenediaminetetraacetate; penta(1-hydroxy-2,2,6,6-tetramethyl-4-hydroxypiperidinium)diethylenetriaminepentaacetate; penta(1-hydroxy-2,2,6,6-tetramethyl-4-acetamidopiperidinium)diethylenetriaminepentaacetate; penta(1-hydroxy-2,2,6,6-tetramethyl-4-oxopiperidinium)diethylenetriaminepentaacetate; tri(1-hydroxy-2,2,6,6-tetramethyl-4-hydroxypiperidinium) nitrilotriacetate; tri(1-hydroxy-2,2,6,6-tetramethyl-4-acetamidopiperidinium) nitrilotriacetate; tri(1-hydroxy-2,2,6,6-tetramethyl-4-oxopiperidinium) nitrilotriacetate; penta(1-hydroxy-2,2,6,6-tetramethyl-4-hydroxypiperidinium) diethylenetriaminepentamethylenephosphonate; penta(1-hydroxy-2,2,6,6-tetramethyl-4-acetamidopiperidinium)diethylenetriaminepentamethylenephosphonate; penta(1-hydroxy-2,2,6,6-tetramethyl-4-oxopiperidinium) diethylenetriaminepentamethylenephosphonate; 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; tetra(1-hydroxy-2,2,6,6-tetramethyl-4-hydroxypiperidinium) ethylenediaminetetraacetate; tetra(1-hydroxy-2,2,6,6-tetramethyl-4-acetamidopiperidinium) ethylenediaminetetraacetate; tetra(1-hydroxy-2,2,6,6-tetramethyl-4-oxopiperidinium) ethylenediaminetetraacetate; penta(1-hydroxy-2,2,6,6-tetramethyl-4-hydroxypiperidinium) diethylenetriaminepentaacetate; penta(1-hydroxy-2,2,6,6-tetramethyl-4-acetamidopiperidinium) diethylenetriaminepentaacetate; penta(1-hydroxy-2,2,6,6-tetramethyl-4-oxopiperidinium) diethylenetriaminepentaacetate; 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; 1-hydroxy-2,2,6,6-tetramethyl-4-hydroxypiperidinium DTPA; bis(1-hydroxy-2,2,6,6-tetramethyl-4-hydroxypiperidinium) DTPA; tris(1-hydroxy-2,2,6,6-tetramethyl-4-hydroxypiperidinium) DTPA; tetrakis(1-hydroxy-2,2,6,6-tetramethyl-4-hydroxypiperidinium) DTPA; pentakis(1-hydroxy-2,2,6,6-tetramethyl-4-hydroxypiperidinium) DTPA; 1-hydroxy-2,2,6,6-tetramethyl-4-hydroxypiperidinium E DTA; bis(1-hydroxy-2,2,6,6-tetramethyl-4-hydroxypiperidinium) EDTA; tris(1-hydroxy-2,2,6,6-tetramethyl-4-hydroxypiperidinium) EDTA; tetrakis(1-hydroxy-2,2,6,6-tetramethyl-4-hydroxypiperidinium) E DTA; 1-hydroxy-2,2,6,6-tetramethyl-4-oxo-piperidinium citrate; bis(1-hydroxy-2,2,6,6-tetramethyl-4-oxo-piperidinium) citrate; tris(1-hydroxy-2,2,6,6-tetramethyl-4-oxo-piperidinium) citrate; 1-hydroxy-2,2,6,6-tetramethyl-4-oxo-piperidinium DTPA; bis(1-hydroxy-2,2,6,6-tetramethyl-4-oxopiperidinium) DTPA; tris(1-hydroxy-2,2,6,6-tetramethyl-4-oxo-piperidinium) DTPA; tetrakis(1-hydroxy-2,2,6,6-tetramethyl-4-oxo-piperidinium) DTPA; pentakis(1-hydroxy-2,2,6,6-tetramethyl-4-oxo-piperidinium) DTPA; 1-hydroxy-2,2,6,6-tetramethyl-4-oxo-piperidinium EDTA; bis(1-hydroxy-2,2,6,6-tetramethyl-4-oxo-piperidinium) EDTA; tris(1-hydroxy-2,2,6,6-tetramethyl-4-oxo-piperidinium) EDTA; tetrakis(1-hydroxy-2,2,6,6-tetramethyl-4-oxo-piperidinium) EDTA; 1-hydroxy-2,2,6,6-tetramethyl-4-acetamidopiperidinium citrate; bis(1-hydroxy-2,2,6,6-tetramethyl-4-acetamidopiperidinium) citrate; tris(1-hydroxy-2,2,6,6-tetramethyl-4-acetamidopiperidinium) citrate; 1-hydroxy-2,2,6,6-tetramethyl-4-acetamidopiperidinium DTPA; bis(1-hydroxy-2,2,6,6-tetramethyl-4-acetamidopiperidinium) DTPA; tris(1-hydroxy-2,2,6,6-tetramethyl-4-acetamidopiperidinium) DTPA; tetrakis(1-hydroxy-2,2,6,6-tetramethyl-4-acetamidopiperidinium) DTPA; pentakis(1-hydroxy-2,2,6,6-tetramethyl-4-acetamidopiperidinium) DTPA; 1-hydroxy-2,2,6,6-tetramethyl-4-acetamidopiperidinium EDTA; bis(1-hydroxy-2,2,6,6-tetramethyl-4-acetamidopiperid in ium) EDTA; tris(1-hydroxy-2,2,6,6-tetramethyl-4-acetamidopiperidinium) EDTA; tetrakis(1-hydroxy-2,2,6,6-tetramethyl-4-hydroxypiperidinium) EDTA; 1-hydroxy-2,2,6,6-tetramethyl-4-acetoxypiperidinium citrate; bis(1-hydroxy-2,2,6,6-tetramethyl-4-acetoxypiperidinium) citrate; tris(1-hydroxy-2,2,6,6-tetramethyl-4-acetoxypiperidinium) citrate; 1-hydroxy-2,2,6,6-tetramethyl-4-acetoxypiperidinium DTPA; bis(1-hydroxy-2,2,6,6-tetramethyl-4-acetoxypiperidinium) DTPA; tris(1-hydroxy-2,2,6,6-tetramethyl-4-acetoxypiperidinium) DTPA; tetrakis(1-hydroxy-2,2,6,6-tetramethyl-4-acetoxypiperidinium) DTPA; pentakis(1-hydroxy-2,2,6,6-tetramethyl-4-acetoxypiperidinium) DTPA; 1-hydroxy-2,2,6,6-tetramethyl-4-acetoxypiperidinium EDTA; bis(1-hydroxy-2,2,6,6-tetramethyl-4-acetoxypiperidinium) EDTA; tris(1-hydroxy-2,2,6,6-tetramethyl-4-acetoxypiperidinium) EDTA and tetrakis-(1-hydroxy-2,2,6,6-tetramethyl-4-acetoxypiperidinium) EDTA;

especially from 2,2,6,6,-tetramethylpiperidine N-oxyl (TEMPO) and the 4-substituted derivatives thereof including 4-methoxy-TEMPO, 4-ethoxy-TEMPO, 4-acetoxy-TEMPO, 4-acetamino-TEMPO, 4-hydroxy-TEMPO, 4-benzoyloxy-TEMPO, 4-amino-TEMPO, N,N-dimethylamino-TEMPO and 4-oxo-TEMPO (see e.g. U.S. Pat. Nos. 7,390,904, 6,825,384 and US 2008/0305055).

As sterically hindered amino compounds, among the preferred ones are those selected from the group consisting of the compounds mentioned as sterically hindered nitroxyls, sterically hindered hydroxylamines and sterically hindered hydroxylamine salt compounds in the preceding section in the reduced form (with N instead of the N—O■). Especially preferred are 2,2,6,6,-tetramethylpiperidine (TEMPO) and the 4-substituted derivatives thereof including 4-methoxy-2,2,6,6,-tetramethylpiperidine, 4-ethoxy-2,2,6,6-tetramethylpiperidine, 4-acetoxy-2,2,6,6-tetramethylpiperidine, 4-acetamino-2,2,6,6-tetramethylpiperidine, 4-hydroxy-2,2,6,6-tetramethylpiperidine, 4-benzoyloxy-2,2,6,6-tetramethylpiperidine, 4-amino-2,2,6,6-tetramethylpiperidine, N,N-dimethylamino-2,2,6,6-tetramethylpiperidine and 4-oxo-2,2,6,6-tetramethylpiperidine (see e.g. U.S. Pat. Nos. 7,390,904, 6,825,384 and US 2008/0305055).

As benzofuranone compounds which may be present in addition to the obligatory compound(s), among the preferred ones are the ones selected from the group consisting of those with the formulae:

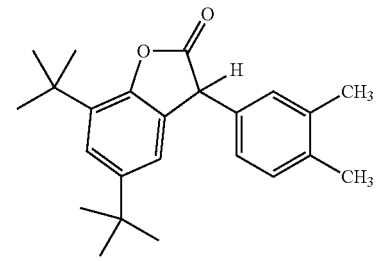

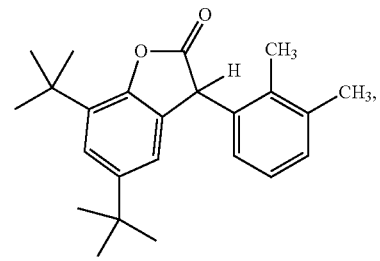

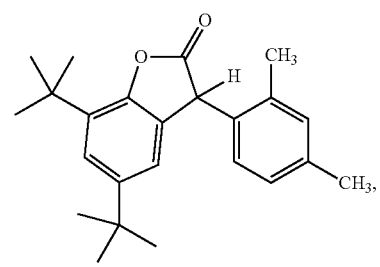

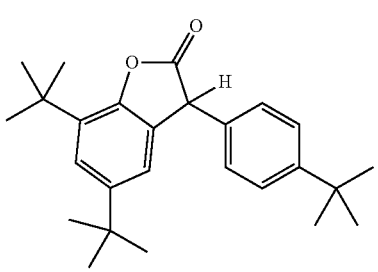

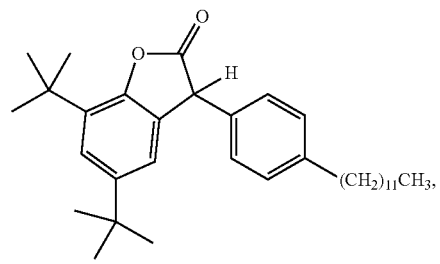

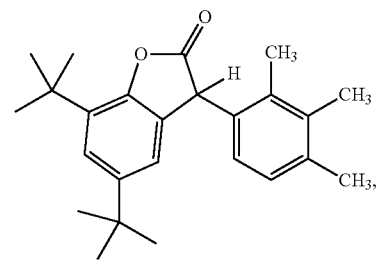

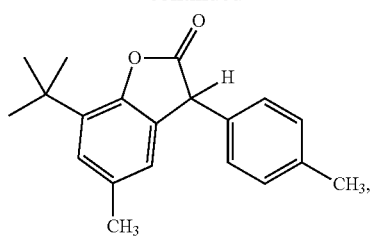
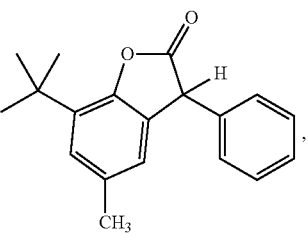
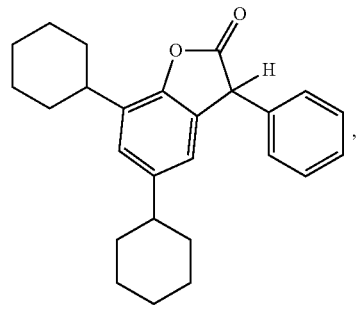
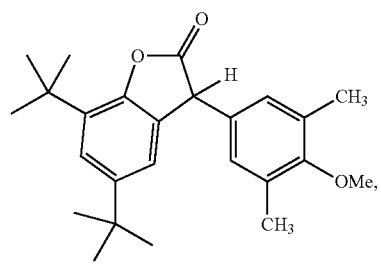
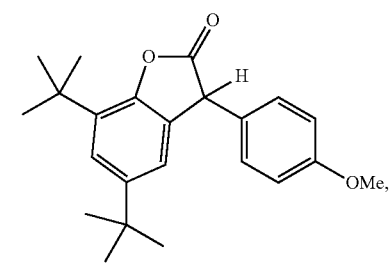
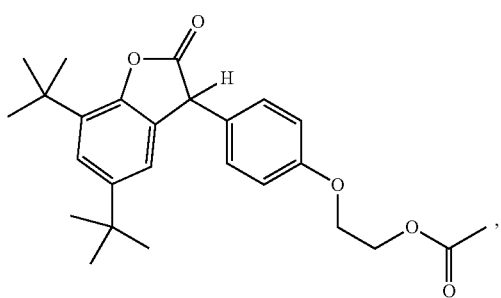
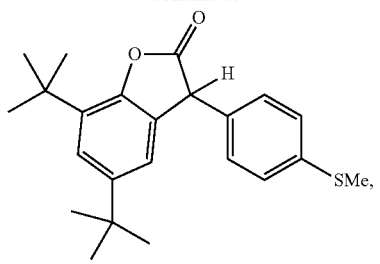
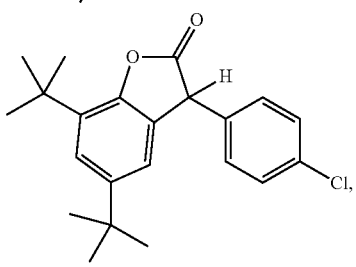
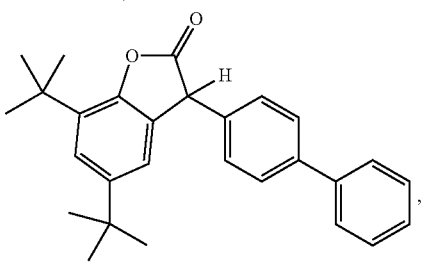
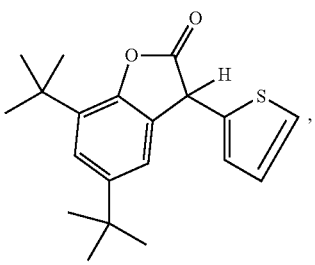
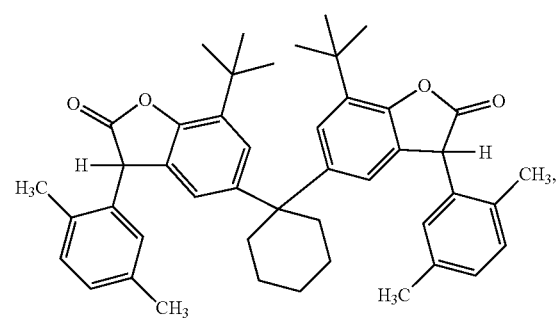
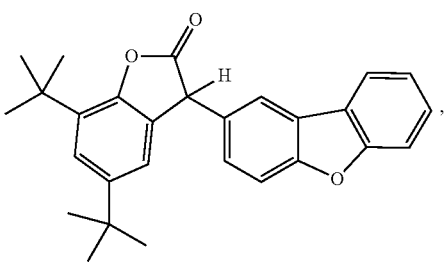

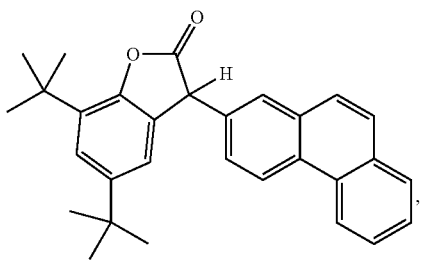
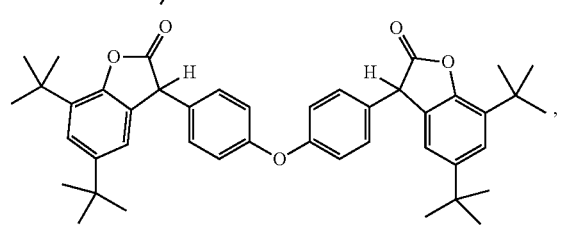
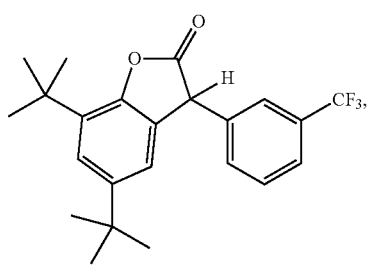
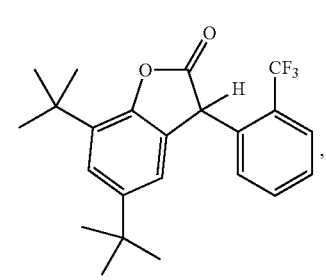
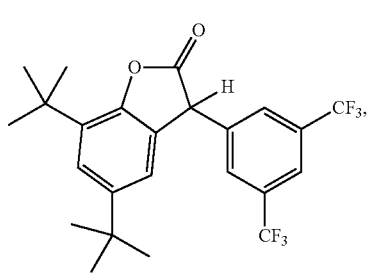
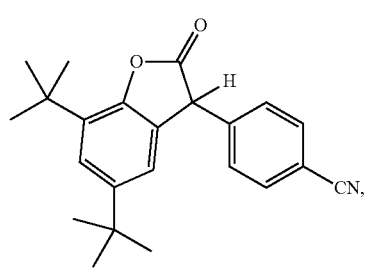
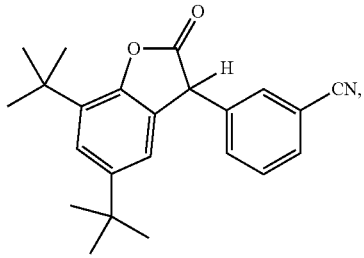
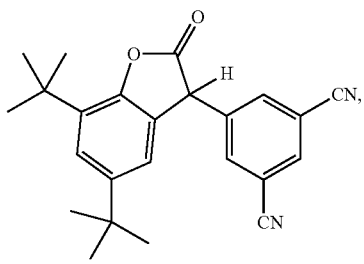
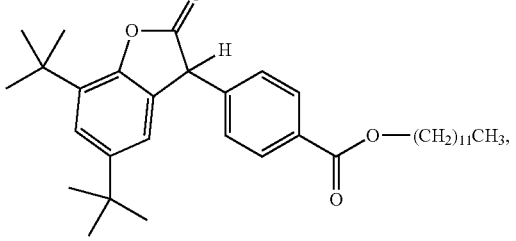
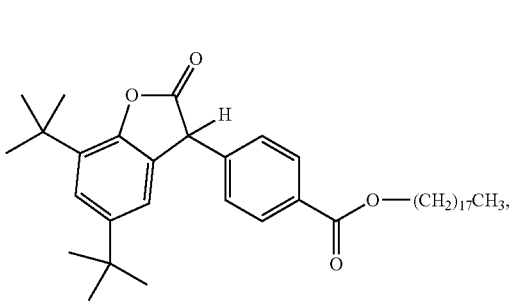
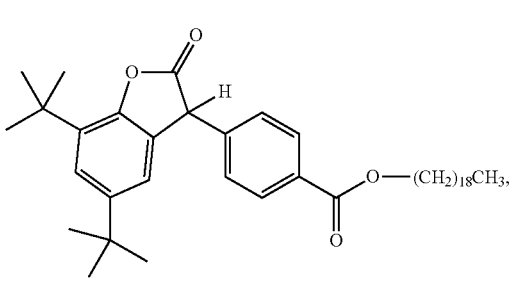
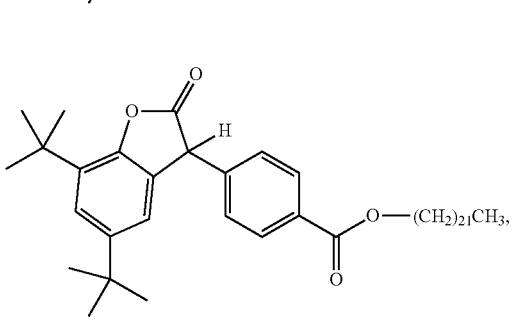

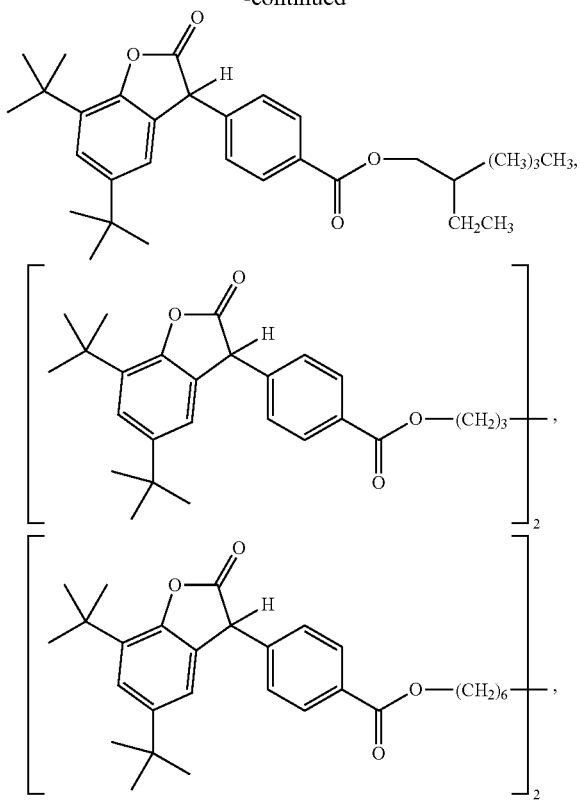

and from those with the names 5,7-di-tert-butyl-3-(2,5-dimethylphenyl)-3H-benzofuran-2-one, 5,7-di-tert-butyl-3-(4-prop-2-yl-phenyl)-3H-benzofuran-2-one, 5,7-di-tert-butyl-3-(4-ethyl-phenyl)-3H-benzofuran-2-one, 5,7-di-tert-butyl-3-(2,3,4,5,6-pentamethylphenyl)-3H-benzofuran-2-one, 5,7-di-tert-butyl-3-phenyl-3H-benzofuran-2-one, 5,7-di-tert-butyl-3-(4-methyl-phenyl)-3H-benzofuran-2-one, 4,4'-bis(5,7-di-tert-butyl-3H-benzofuran-2-on-3-yl)-N-methyl-diphenylamine, 5,7-di-tert-butyl-3-(3,5-dimethyl-4-hydroxyphenyl)-3H-benzofuran-2-one, 7-tert-butyl-5-methyl-3-(9-methyl-9H-carbazol-3-yl)-3H-benzofuran-2-one, 5,7-di-tert-butyl-3-(9H-fluoren-3-yl)-3H-benzofuran-2-one, 3-(3,4-dimethylphenyl)-5,7-di-tert-butyl-3H-benzofuran-2-one, 3-(2,3-dimethylphenyl)-5,7-di-tert-butyl-3H-benzofuran-2-one, 3-(N-methylcarbamoyloxy)-5-methyl-7-tert-butyl-3H-benzofuran-2-one, 7-tert-butyl-3-chloro-5-methyl-3H-benzofuran-2-one, 5,7-di-tert-butyl-3-(4-trifluoromethyl-phenyl)-3H-benzofuranone, 5,7-di-tert-butyl-3-(4-fluoro-phenyl)-3H-benzofuranone, 5,7-di-tert-butyl-3-(4-methoxycarbonyl-phenyl)-3H-benzofuranone and 5,7-di-tert-butyl-3-(4-n-octyloxycarbonyl-phenyl)-3H-benzofuranone (see e.g. U.S. Pat. Nos. 5,607,624, 5,607,624, US 2003/0212170 and US 2008/0305055).

As nitrones which may be present in addition to the obligatory compound(s), among the preferred ones are the ones selected from the group consisting of N-decyl-alpha-nonyl nitrone, the nitrone derived by oxidation with tert-butyl hydroperoxide solution in toluene from N,N-di(hydrogenated tallow) hydroxylamine, N-tert-butyl-alpha-phenyl nitrone, N-octadecyl-alpha-heptadecyl nitrone, 3,4-dihydro-3,3-dimethylisoquinoline N-oxide, 3,3-dimethyl-7-methoxy-3,4-dihydroisoquinoline-N-oxide, 7-chloro-3,3-dimethyl-3,4-dihydroisoquinoline-N-oxide, 7-fluoro-3,3-dimethyl-3,4-dihydroisoquinoline-N-oxide, spiro [cyclohexane-1,3']-3,4-dihydroisoquinoline-N-oxide, spiro [cyclopentane-1,3']-1H-dihydroisoquinoline 2-oxide, 6-chloro spiro[cyclopentane-1,3']-1H-isoindole-N-oxide, 7-fluoro-spiro[cyclopentane-1,3']-1H-isoindole-N-oxide, 3,3-dimethyl-7-trifluoro-methyl-3,4-dihydroisoquinoline-N-oxide, 3,3-dimethyl-7-hydroxy-3,4-dihydroisoquinoline-N-oxide, spiro[cyclopentane-1,1'-[1H]-isoindole-N-oxide, 3,3-dimethyl-[1H]-isoindole-N-oxide, 5-chloro-3,3-dimethyl-3,4-dihydroisoquinoline-N-oxide, 3,3-dimethyl-4,5-dihydro-3H-2-benzazepine-1-oxide, 8-chloro-3,3-dimethyl-3,4-dihydroisoquinoline-N-oxide, 6,8-dichloro-3,3-dimethyl-3,4-dihydroisoquinoline-N-oxide, 6-chloro-3,3-dimethyl-3,4-dihydroisoquinoline-N-oxide, spiro [cyclohexane-1,3]-3,4-dihydroisoquinoline-N-oxide, spiro [cyclohexane-1,3]-7-chloro-3,4-dihydroisoquinoline-N-oxide, spiro [cyclohexane-1,3']-6-methoxy-3,4-dihydroisoquinoline-N-oxide, spiro[cyclohexane-1,3']-8-methoxy-3,4-dihydro-isoquinoline-N-oxide, 3,3-dimethyl-6,7-dimethoxy-3,4-dihydroisoquino-line-N-oxide, 3,3-dimethyl-6-methoxy-3,4-dihydroisoquinoline-N-oxide and 3,3-dimethyl-8-methoxy-3,4-dihydro isoquinoline-N-oxide (see e.g. U.S. Pat. Nos. 4,898,901 and 5,677,315).

As (preferably sterically hindered) phenol antioxidants that may be present in addition to the obligatory compound(s), among the preferred ones are the ones selected from the group consisting of 3,5-di-tert-butyl-4-hydroxy-hydrocinnamic acid and from those with the formulae

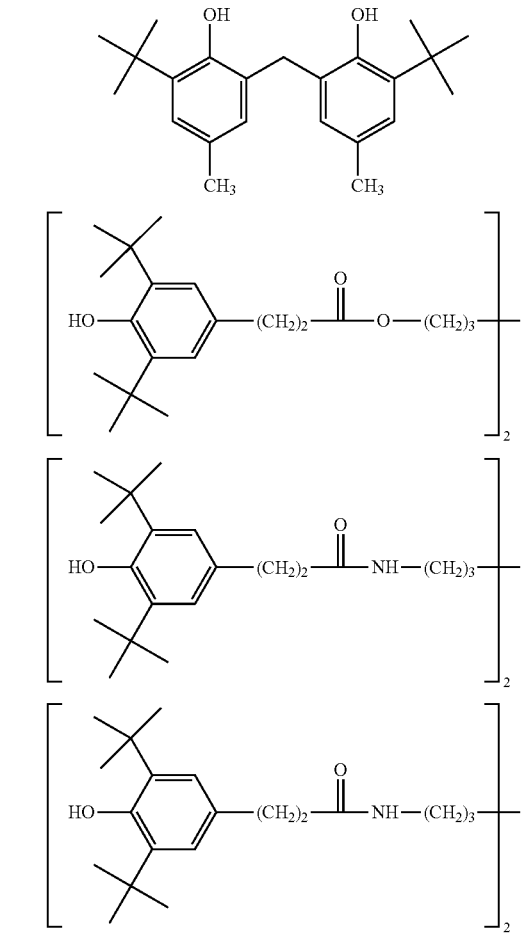

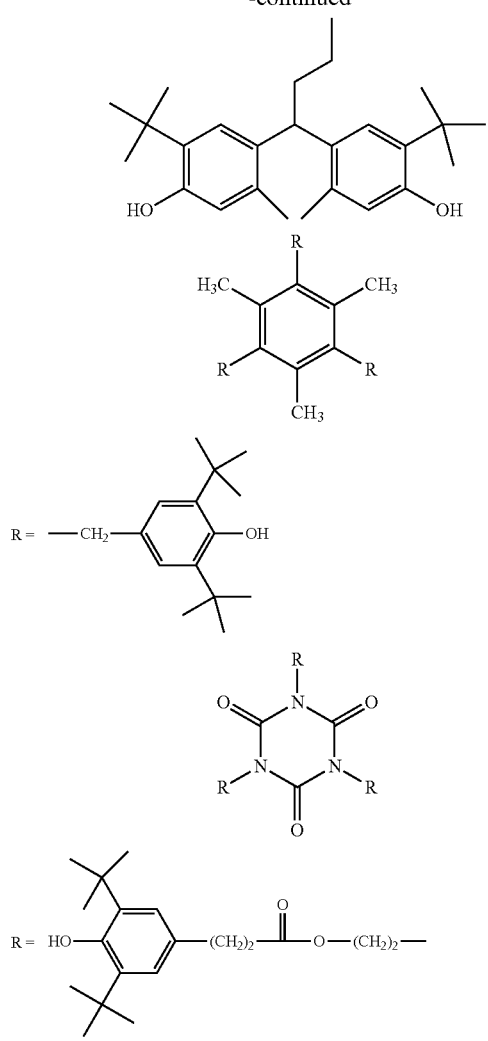
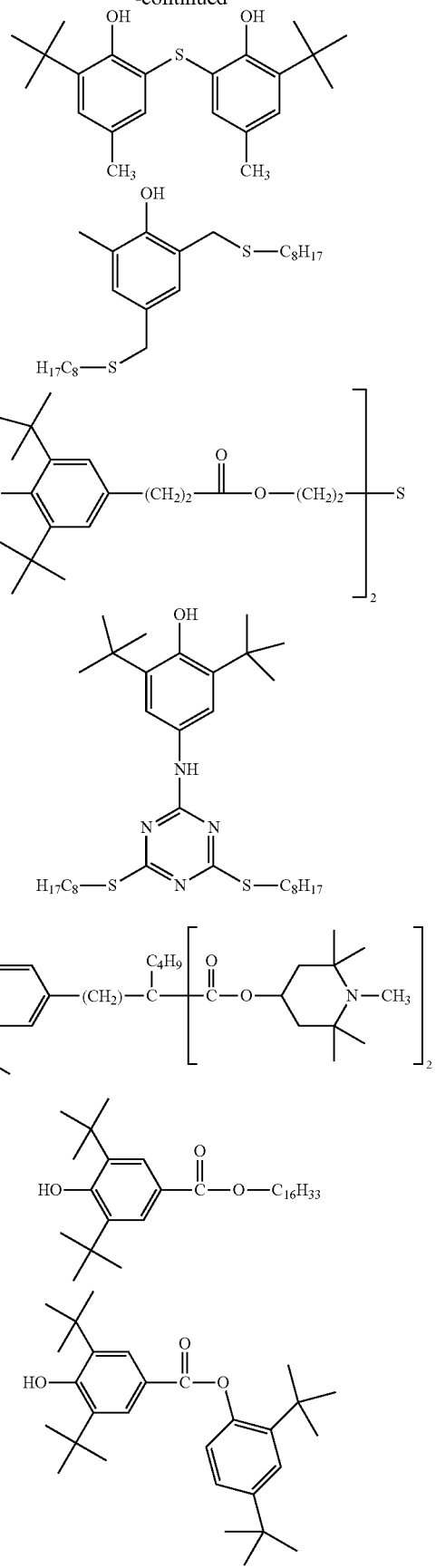

-continued

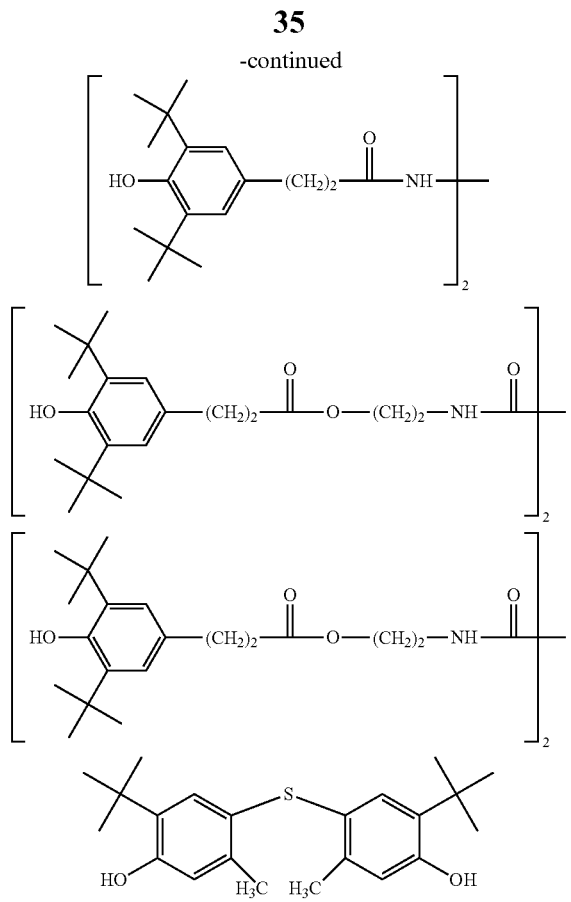

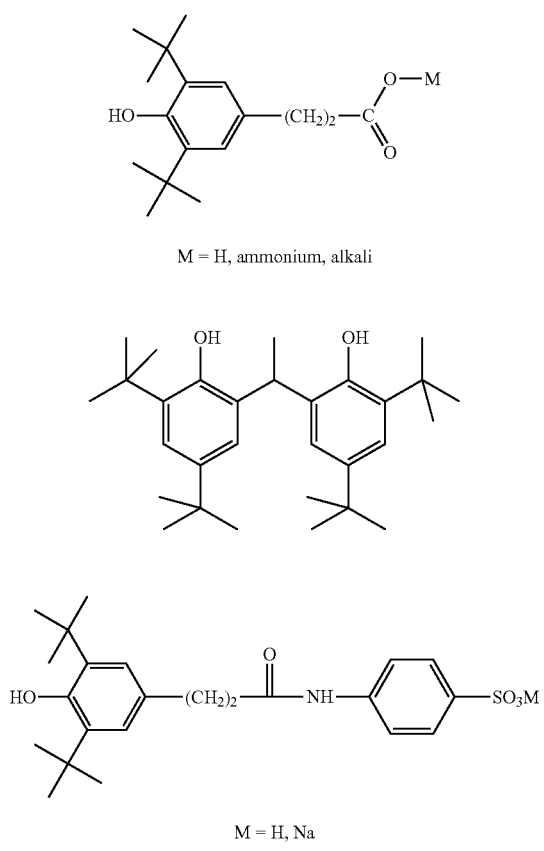

-continued (see e.g. U.S. Pat. No. 7,323,505, WO00/32687 and US 2008/0305055).

As natural antioxidants or radical scavengers that may be present in addition to the obligatory compound(s), the following may be mentioned as preferred: amino acids (e.g. glycine, histidine, tyrosine, tryptophan), urocanic acid D,L-carnosine, D-carnosine, L-carnosine, anserine, carotinoids, carotenes, lycopene, chlorogenic acid, lipoic acid, dihydrolipoic acid, aurothioglycose, propylthiouracil, thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl derivatives thereof, dilauryl thiodipropionate, distear[gamma]l thiodipropionate, thiodipropionic acid, buthionine sulfoximine, homocysteine sulfoximine, buthionine sulfone, penta-, hexa-, hepta-thionine sulfoximine, hydroxy fatty acids, palmitic acid, phytic acid, lactoferrin, chitosan, phosphonomethylated chitosan, citric acid, lactic acid, malic acid, humic acid, bile acid, bile extracts, bilirubin, biliverdin, EDTA, EDDS, EGTA, linolenic acid, linoleic acid, oleic acid, folic acid, ubiquinone, ubiquinol, vitamin C, ascorbyl palmitate, magnesium ascorbyl phosphate, ascorbyl acetate, tocopherols, vitamin E acetate, vitamin A, vitamin A palmitate, coniferyl benzoate of benzoin resin, rutinic acid, glycosylrutin, ferulic acid, furfurylidene glucitol, butyl hydroxytoluene, butyl hydroxyanisole, nordihydroguaiaretic acid, trihydroxybutyrophenone, uric acid, mannose, superoxide dismutase, N-[3-(3,5-di-tert-butyl-4-hydroxyphenyl)propionyl]sulfanilic acid, zinc, ZnO, ZnSO4, selenium, selenium methionine, stilbene, stilbene oxide or trans-stilbene oxide.

As coumestanes that may be present in addition to the obligatory compound(s), the following may be mentioned as preferred:

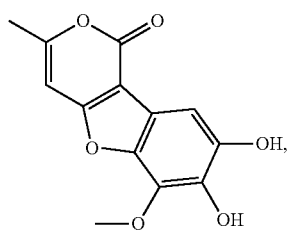 (A-1)
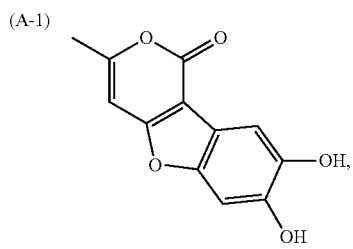 (A-2)
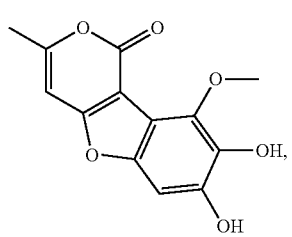 (A-3)
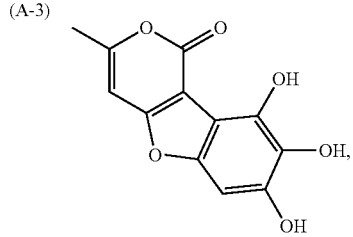 (A-4)
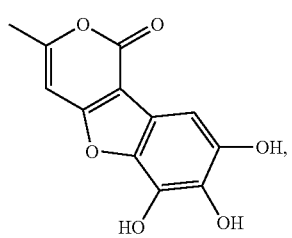 (A-5)
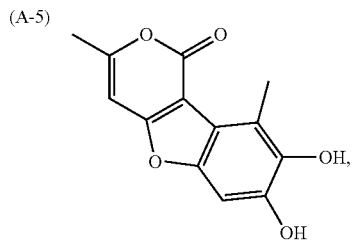 (A-6)
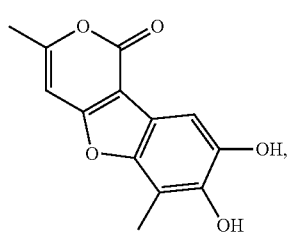 (A-7)
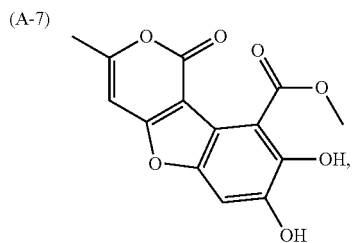 (A-8)
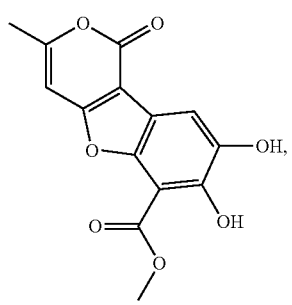 (A-9)
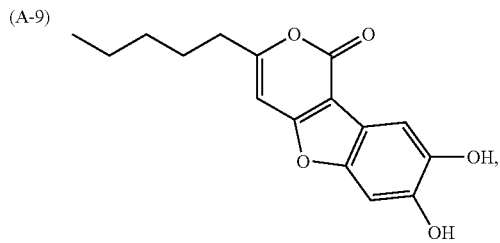 (A-10)
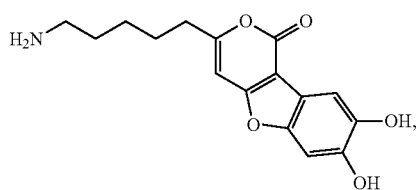 (A-11)
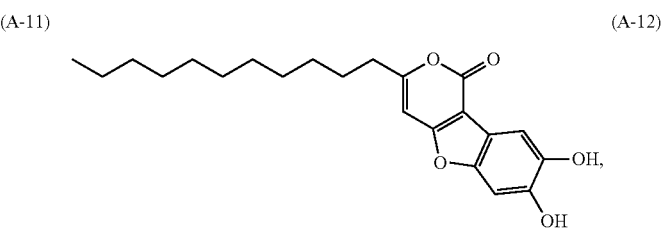 (A-12)

-continued
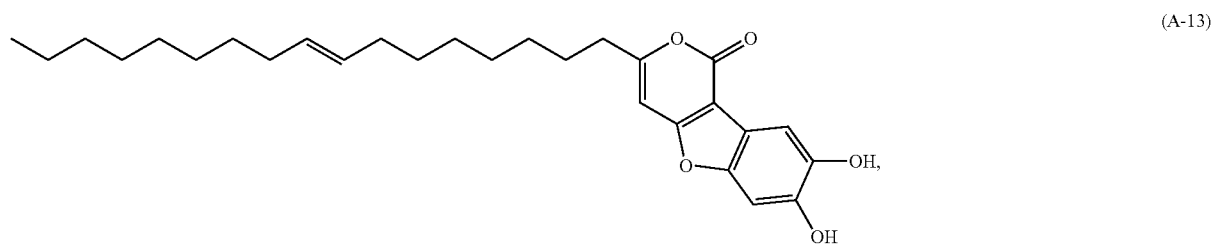
(A-13)
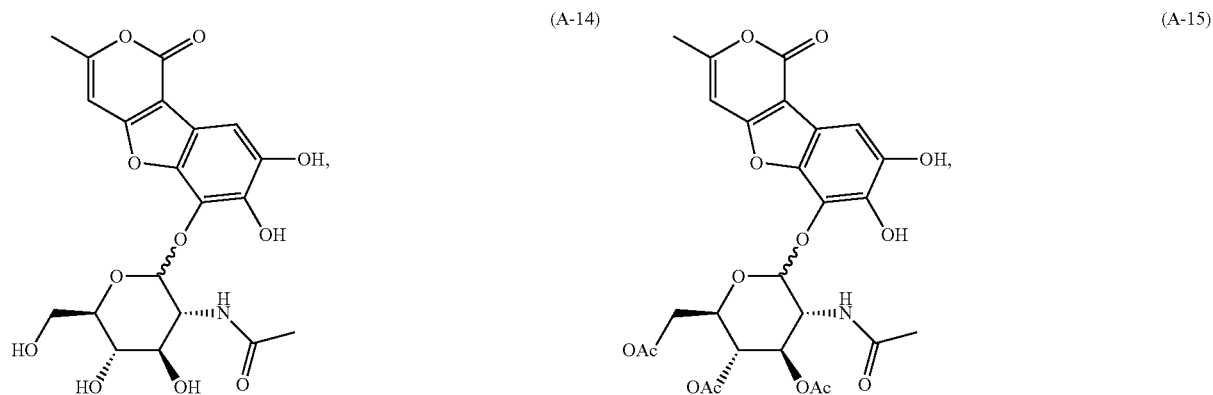
(A-14) (A-15)
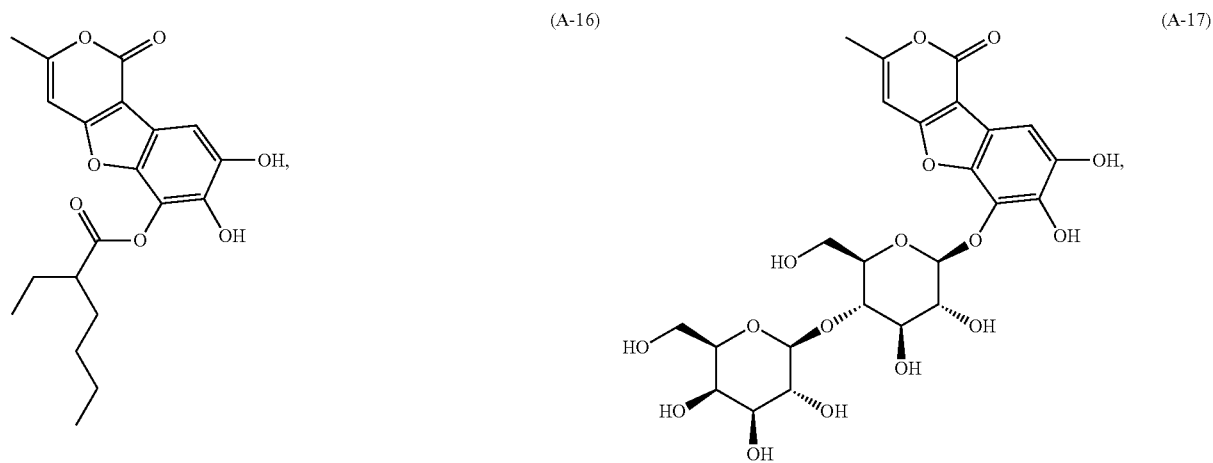
(A-16) (A-17)
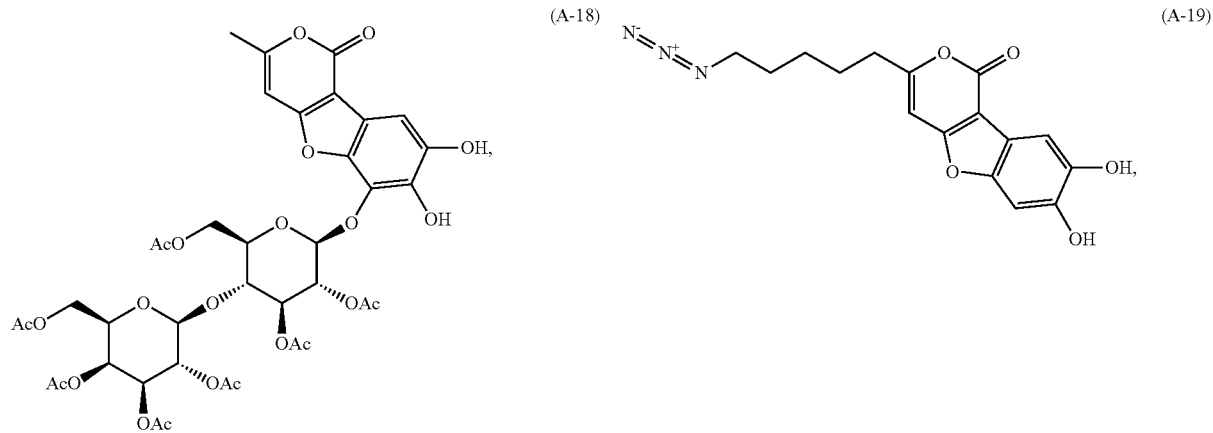
(A-18) (A-19)

-continued
(A-20) 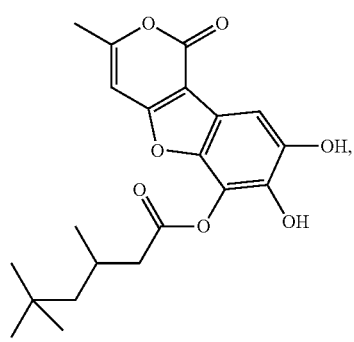
(A-21) 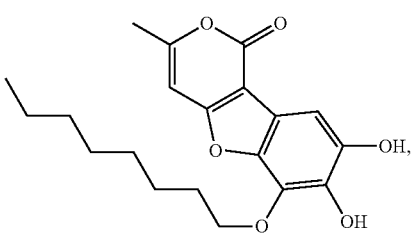
(A-22) 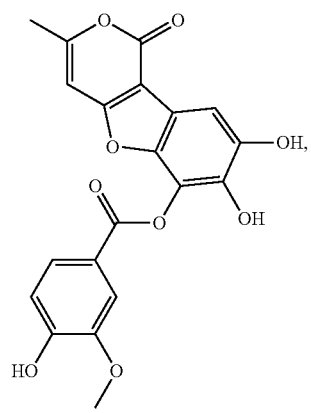
(A-23) 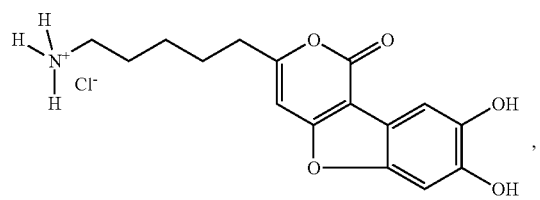
(A-24) 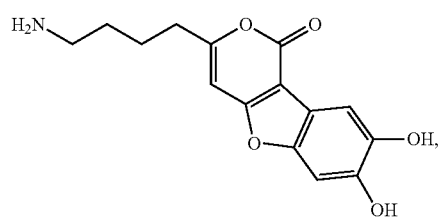
(A-25) 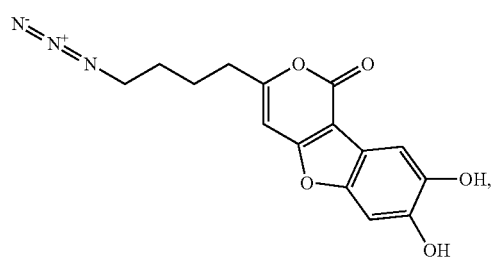
(A-26) 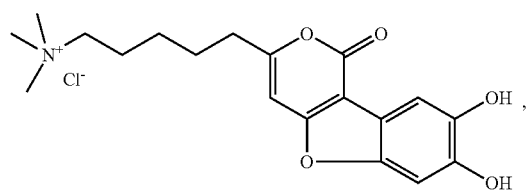
(A-27) 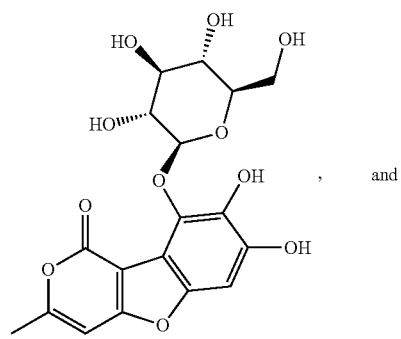
, and
(A-28) 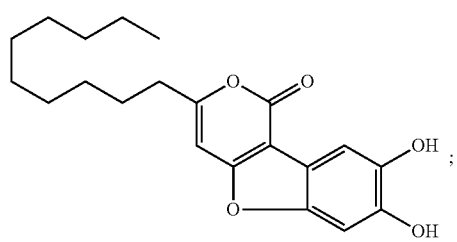
(B-1) 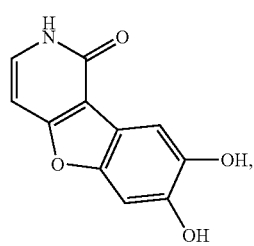

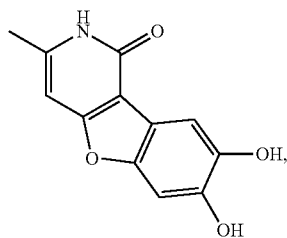

(B-2)

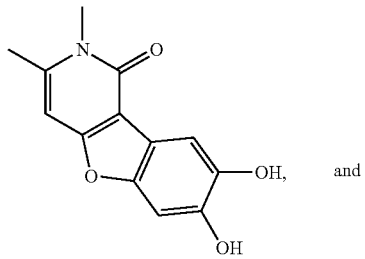

(B-3)

and

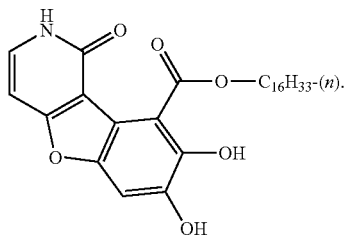

(B-4)

In all cases, the additive(s), where salt-forming groups (e.g. amino, imino, carboxyl, sulfoxyl, phenolic hydroxy or the like) are present, may also be used in the form of salts, or in the free form, or as mixture of salt(s) and free form.

Especially preferred are (a) sterically hindered nitroxyls, sterically hindered hydroxylamines and sterically hindered hydroxylamine salt compounds, more especially sterically hindered nitroxyls; and (b) sterically hindered amines, especially as defined under (i) and/or (ii) above or more especially as defined in the preceding paragraphs or in the subsequent paragraph; alone (preferred) or in combination with any one of the compounds mentioned under (α) to (ε) above, e.g. (c) sterically hindered phenols; or combinations of two or more compounds selected from those falling under (a) and (b) and (c) just mentioned; most especially sterically hindered nitroxyls; where in each case the more preferred of these compounds are as defined above or below. Among the sterically hindered nitroxyls, sterically hindered hydroxylamines and sterically hindered hydroxylamine salt compounds, those carrying no hydroxyl substituent are especially preferred.

Highly preferred are 4-hydroxy-2,2,6,6-tetramethylpiperidin-1-oxyl and 4-hydroxy-2,2,6,6-tetramethylpiperidin, or combinations of two or all three thereof, alone or in combination with 3,5-di-tert-butyl-4-hydroxy-hydrocinnamic acid, and/or a salt thereof.

The additive(s) can be present in free form and/or in salt form, e.g. as salts with metal cations, such as sodium, potassium or calcium cations, or bases, e.g. ammonium or alkylammonium salts, or as salts with organic or inorganic anions (acid additions salts), e.g. as acetates, methanesulfonates, tolylsulfonates, halogenides, such as chlorides or bromides, sulfates, phosphates or the like, or, where both one or more negatively and positively charged groups are present in one molecule, as internal salts, or any mixtures thereof. Preferred are nutraceutically and/or pharmacologically acceptable salts.

Some are always in the form of salts (e.g. hydroxylamine salt compounds).

The obligatory (and if used optional) additive(s), and/or a salt thereof, may be present during the whole cultication or biosynthesis process or only during parts thereof, e.g. before or after the maximum cell density has been reached or the like.

Products obtainable according to the methods and processes according to the invention can be small molecular entities or macromolecules—they are all preferably organic molecules.

They can be obtained in free form and/or in the form of (especially pharmaceutically acceptable) salts, e.g. acid addition salts where they comprise basic groups, e.g. amino, e.g. with organic or inorganic acids, such as hydrochloric acid or methane sulfonic acid, or salts with bases where they comprise acidic groups, e.g. carboxyl or sulfonic acids groups, e.g. with ammonia, a pharmaceutically acceptable positively charged metal ion, such as $Na^+$, or organic amines, such as tetra-alkyl-ammonium salts, and/or, where they contain both acidic and basic groups, inner salts. Solvates, e.g. hydrates, are also possible alternatives. Also internal salts are possible where one or more positive and negative groups are present in a molecule (e.g. in proteins or amino acids). Preferred are nutraceutically and/or pharmaceutically acceptable salts. Of course salts can be converted into the free form and vice versa according to procedures known in the art.

Proteins or other macromolecules that can be produced according to the invention are not limited and may be natural, recombinant or other forms as appropriate.

Among the proteins to be produced, e.g. the following may be mentioned (r stands for recombinant, h for human):

Antibodies, such as

Amevive® (=alefacept, against proriasis) (Biogen), Bexxar® (tositumomab against lymphoma) (Cirica/GlaxoSmithKline), Campath® (alemtuzumab against leukaemia etc.) (Ilex/Berlex), Enbrel® (etanercept, against TNF-alfa, rheumatoid arthritis) (Amgen/Wyeth) Herceptin® (trastuzumab, against breast cancer etc.) (Genentech), Humira® (alamimumab, against rheumatoid arthritis) (Abbott), Mylotarg® (gemtuzumab ozogamicin, humanized antibody against CD33, fused to bacterial toxin, e.g. against leukaemia) (Wyeth), OKT-3 (muromonab-CD3, against leukaemia) (Johnson & Johnson), raptiva (efalizumab; psoriasis) (Genentech/Serono), Remicade (infliximab, against Colitis Ulcerosa etc.) (Johnson & Johnson), Lucentis® (ranibizumab, against uveitis) (Novartis) or Avastin® (bevacizumab against cancer or uveitis);

Hormones, e.g. (for example human or bovine) growth hormone, pegylated forms thereof, e.g. pegylated rhGH analogue, insulin, e.g. Insulin HisPro 393-409, Insulin glusiline, Insulin aspart, Insulin glurgin, Insulin detemir, Insulin human or the like, sexual hormones, e.g. Follistim®/Puregon® (follitropin beta, against infertility) (Organon), human chorionic gonadotropin, human luteinizing hormone, PTH, such as rPTH, calcitonin, such as r salmon calcitonin, or glucagon, e.g. rh glucagons;

Vaccines, e.g. hepatitis B vaccine, malaria antigen, Dengue Virus type 2 envelope protein, or cattle food-and-mouth disease vaccine;

Toxins, e.g. cholera toxin, r Choleratoxin B subunit, heat labile enterotoxin or protein A, pertussis toxin;

Enzymes, e.g. tissue plasminogen activator (e.g. htPA)), hydrolases, e.g. esterases, such as lipases, or peptidases or proteases, such as chymosin (e.g. bovine), pepsin, trypsin, papain, *Fusarium* alkaline protease, or matrix mealloproteinases, rennin, e.g. *Mucor* rennin, or other enzymes, such as adenosine-deaminase, α-glucosidase, α-galactosidase A, alglucerase, pegademase, dornase, imiglucerase (e.g. Cerezyme® (=beta-glucocerebrosidase—e.g. against Morbus Gaucher Type 1) (Genzyme), pegaspargase, sacrosidase, rasbaricase, agalsidase beta, (e.g. Fabrazyme® (agalsidase beta=recombinant human alpha-galactosidase enzyme, against Morbus Fabry) (Genzyme), laronidase (e.g. Aldurazyme® (laronidase, against mucopolysaccharidosis) (Genzyme/BioMarin)), superoxide dismutase, asparaginase, e.g. *Erwinia*-L-asparaginase, $T_4$ endonuclease, glucocerebrosidase, butyrylcholinesterase, chondroitinase, aglucerase, collagenase, alteplase, dieteplase, chloramfenicol acetyl transferase, transglutaminase, creatinine iminohydrolase, α-amylase, trypsin inhibitor, SFV, β-lactamase, urate oxidase, phytase, laccase, xylanase, β-D-glucuronidase or naproxen esterase;

Proteins useful in cancer treatment, e.g. Elitek® (rasburicase against pancreatic cancer) (Sanofi/Synthelabo);

Proteins useful in the treatment of bone disorders, e.g. Forteo® (ezetimib, against osteoporosis) (Eli Lilly);

Batch proteins, e.g. casein, serum albumin (e.g. human), leptin or human caseinomacropeptide;

Interferons, e.g. of the α, β or γ family, such as interferon γ-1b, e.g. Actimune® (interferon gamma-1b, against chronic granulomatous diseases, malignant osteopetrosis etc.) (Intermune), recombinant interferon β-1b, Avonex® (interferon beta-1, against Multiple Sclerosis etc.) (Biogen), Betaseron®/Betaferon® (interferon beta-1b, against Multiple Sclerosis) (Berlex/Schering), human leukocyte interferon, a consensus interferon, interferon alpha1, pegylated interferons, e.g. (Peg) rh interferon α-2 or α-2b, interferon alfacon-1 or recombinant interferon γ-1b;

Interleukins or related proteins such as interleukin receptor antagonists, e.g. Interleukin-1-β, rh IL-1 receptor antagonist, r IL-2, r IL-diphteria toxin fusion or r IL-11;

Blood factors or thrombolytic agents, such as tissue Plasminogen Activator (tPA), Activase® (tissue plasminogen activator, thrombolytic) (Genentech) or BeneFIX® (recombinant factor IX, against hemophilia) (Wyeth BioPharma (GI));

Haematopoietic growth factors, such as erythropoietien, Colony-stimulating factor, Granulocyte-Macrophage Stimulating Factor (GM-CSF), Aranesp® (darbepoetin alfa, against anaemia etc.) (Amgen), Epogen® (erythropoietin alfa, against anemia) (Amgen) or Leucomax® (molgramostim, granulocyte-macrophage colony stimulating factor, hematopoietic), pegylated rh G-CSF or rh GM-CSF other than mentioned;

Other growth factors, e.g. (e.g. human) Epidermal Growth Factor, human transforming growth factor alpha, TGF-α, Insulin-like Growth Factor I, (e.g. human) Nerve Growth Factor or Platelet Derived Growth Factor;

Tumor Necrosis Factor, e.g. hTNF-β or rh TNF-α;

Other proteins, e.g. rHBsAg, RospA, rh B-type natriuretic peptide, cB2 cannabinoid receptor, erythrocyte binding factor, hirudin, avidin or cystatin C.

Among the nucleic acids to be produced (which includes derivatives thereof), there may be mentioned Antisense therapeutics, e.g. Fomivirsen;

Ribozymes, e.g. as therapeutic agents (e.g. hammerhead riboyzmes), as enzymes which tailor defined RNA sequences, as biosensors, or for applications in functional genomics and gene discovery;

Gene therapeutics, including vectors commonly used to package the DNA and cross the cell membrane to deliver DNA to the nucleus of the target cell. Viral vectors are commonly used delivery devices for DNA. Viruses can be used to carry therapeutic genes in addition to their own DNA. Retroviruses are especially well suited to this task as they integrate their DNA into the host genome, ensuring longlasting effects. Non-viral mechanisms of gene-delivery include intramuscular injection of naked DNA. Injection of PCR product has also had some success. Other mechanisms of delivery of naked DNA includes electroporation and the use of a gene gun which shoots gold particles covered in DNA into the cell. Also the use of synthetic nucleotides to disrupt gene expression is possible;

siRNAs, which are able to knock down essentially any gene of interest, e.g. indicated for age-related macular degeneration, aka AMD) or for siRNA-based treatment that counteracts the Human Immunodeficiency Virus (HIV).

The general term "antibody" or "antibodies", within the present disclosure and if not specified otherwise, is intended to include polyclonal or monoclonal antibodies, bispecific antibodies, humanized antibodies, chimeric antibodies, single chain antibodies, or fragments of any one or more of these forms that still recognize, especially show a (substantially or fully selective) binding affinity to (preferably with a dissociation constant K of $10^{-4}$ or lower, more preferably of $10^{-6}$ or lower, still more preferably of $10^{-8}$ or lower), a macromolecule, e.g. a protein, or fragments thereof, including one or both of conformational or (preferably) primary structure related (e.g. phosphotyrosine comprising) epitopes. Thus, "antibody" refers especially to a protein functionally defined as a binding protein (a molecule able to bind to a specific (conformational and/or primary structure related) epitope on an antigen) and structurally defined as comprising an amino acid sequence that is recognized by a person skilled in the art as being derived from the framework region of an immunoglobulin encoding gene. Structurally, the simplest naturally occurring antibody (e.g. IgG) comprised four polypeptide chains, two copies of heavy (H) chain and two copies of light (L) chain, all covalently linked by disulfide bonds. Specificity of binding to the epitope is found in the variable (V) region of the H and L chains. Regions of the antibodies that are primarily structural are constant (C). The term "antibody" includes whole antibodies, still binding fragments, modifications or derivatives of an antibody. It can also be a recombinant product, or a bispecific antibody or chimeric antibody, such as a humanized antibody. Antibodies can be a polyclonal mixture or (more than one or especially one) monoclonal. They can be intact immunoglobulins derived from a natural source or natural sources and can be immunoreactive (binding) portions of intact immunoglobulins. Antibodies may show a variety of forms (derivatives), including, for example, Fv (consisting of $V_L$ and $V_H$ domains), a dAB fragment (consisting of a $V_H$ domain; see Ward et al., Nature 341: 544-546, 1989), an isolated complementarity determining region (CDR), Fab (consisting of the $V_L$, $V_H$, $C_L$ and $C_{H1}$ domains), and $F(ab)_2$ (a bivalent fragment comprising two Fab fragments linked by a disulfide bridge at the hinge region) as well as in single chains. Single chain antibodies (SCA), in which genes for a heavy chain and a light chain are combined into a single coding sequence, may also be used. Some SCA are recombinant molecules containing the variable region of the light chain, the variable region of the heavy chain and a suitable polypeptide linker linking them. Recognizing or recognition especially means that there is a (preferably specific, e.g. 100-fold, preferably 1000-fold, more preferably 10,000-fold or in each case lower dissociations constant than for any other molecule present in a sample) binding with high affinity, e.g. with a dissociation constant of $10^{-4}$, more preferably $10^{-6}$, yet more preferably $10^{-8}$ or in each case lower, to the respective molecule of interest. Dissociation constants, where mentioned, are preferably measured in phosphate buffered saline pH 7.4 which can be prepared as follows: A 10 liter stock of 10×PBS can be prepared by dissolving 800 g NaCl, 20 g KCl, 144 g Na2HPO4 and 24 g KH2PO4 in 8 L of distilled water, and topping up to 10 L. The pH is ~6.8, but when diluted to 1×PBS it should change to 7.4. On dilution, the resultant 1×PBS will have a final concentration: 137 mM NaCl, 10 mM Phosphate, 2.7 mM KCl, pH 7.4.

Also small molecular entities can be manufactured according to the invention.

As examples,

Sugars, e.g. mono-, die- or trisaccharides, such as glucose, fructose, galactose, xylose, ribose, sucrose, lactose, maltose, trehalose, cellobiose, kojibiose, nigerose, isomaltose, β,β-trehalose, sophorose, laminaribiose, gentiobiose, turanose, maltulose, palatinose, gentiobiulose, mannobiose, melibiose, melibiulose, rutinose, rutinulose, xylobiose, nigerotriose, maltotriose, melezitose, maltutriulose, raffinose or kestose;

Amino acids or derivatives thereof, e.g. the 22 natural proteinogenic amino acids (including the 20 standard amino acids and selenocysteine and pyrrolysine), or other, such as keratin or taurin and amines such as 1,5 diaminopentane;

Organic acids such as tartaric acid, itaconic acid, succinic acid, fumaric acid, maleic acid, 2,5-furandicarboxylic acid, 3-hydroxypropionic acid, glutaric acid, levulic acid, lactic acid, propionic acid, gluconic acid, aconitic acid and diaminopimelic acid, citric acid;

purine and pyrimidine bases; nucleosides and nucleotides, for example nicotinamide adenine dinucleotide (NAD) and adenosine-5'-monophosphate (AMP);

alcohols including primary alcohols such as ethanol, propanol, butanol, higher-functionality alcohols having 3 or more, for example 3, 4, 5 or 6, OH groups, for example glycerol, sorbitol, mannitol, xylitol and arabinitol, longer-chain alcohols having at least 4 carbon atoms, for example 4 to 22 carbon atoms, diols having preferably 3 to 8 carbon atoms, for example propanediol and butanediol; carbohydrates, for example hyaluronic acid and trehalose;

aromatic compounds, for example aromatic amines, vanillin and indigo;

carotenoids, for example lycopene, β-carotin, astaxanthin, zeaxanthin and canthaxanthin; ketones having preferably 3 to 10 carbon atoms and, if appropriate, 1 or more hydroxyl groups, for example acetone and acetoin;

lactones, for example γ-butyrolactone, cyclodextrins, biopolymers, for example polyhydroxyacetate, polyesters, polysaccharides, polyisoprenoids, polyamides, polyhydroxyalkanoates, for example poly-3-hydroxybutyric acid and copolyesters with other organic hydroxycarboxylic acids such as 3-hydroxyvaleric acid, 4-hydroxybutyric acid and precursors and derivatives of the abovementioned compounds;

Vitamins such as ascorbic acid, vitamins D, e.g. $D_2$ or $D_3$, vitamin E, vitamin $B_1$ (thiamine), vitamin $B_2$ (riboflavine), vitamin A (retinol), vitamin $B_6$ (pyridoxine), vitamin $B_{12}$ (cobalamine or cyanocobalamine), vitamin $B_{15}$ (pangramic acid), folic acid, nicotinamide, pantothenic acid, vitamin F (unsaturated fatty acids, e.g. omega-3 unsaturated fatty acids and the like) vitamin H (biotine), vitamins K (phylloquinones), vitamin P (flavonoids), vitamin U (methylmethioniumchloride)

Steroids, such as saponines, steroid hormones, e.g. estrogens, gestagens, androgens, glucocorticoids, miner corticoids, colecalciferol or ecdysones, cholic acids, heart glycosides, steroid alkaloids or the like;

Antibiotics or their precursors, e.g. 6-deoxyerythronolide, penicillins, cephalosporins, polymixins, quinolones, sulfonamides, aminoglykosides, macrolides, tetracyclins, cyclic lipopeptides, such as daptomycin, glycylcyclines, e.g. tigecycline, oxazolidinones, e.g. linezolid or chloramphenicol;

Other oligopeptides, e.g. opioids, such as enkephalin, endorphines or dynorphines;

Lipids other than those already mentioned (e.g. as "vitamins"), e.g. fatty acids, monoglycerides, diglycerides, phospholipids, glycerophospholipids, sphingolipids, sterol lipids, prenol lipids, saccharolipids or polyketides;

Other small molecular entities, e.g. epothilones, paclitaxel, docetaxel, halichondrin B, discodermolide or bengamide;

Other compounds which are suitable are described by Gutcho in Chemicals by Fermentation, Noyes Data Corporation (1973), ISBN: 0818805086 or other e.g. pharmacologically, agriculturally, nutritionally, scientifically or otherwise interesting product molecules may be mentioned.

For example, pharmacologically (or also nutraceutically or as food supplement) useful product molecules may be useful in the prophylactical and/or therapeutical treatment of various disorders or diseases, including infection, e.g. by virus, bacteria, fungi, prions or the like, such as influenza, AIDS or hepatitis; treatment of metabolic disorders, e.g. syndrome X or diabetes; treatment of immunologic disorders or inflammation; treatment of diseases or disorders of the central nervous system; respiratory diseases; diseases of the gastrointestinal tract, diseases of the musculo-skeletal system, e.g. ALS or osteoporosis; proliferative diseases, e.g. tumor or cancer diseases; malnutrition; diseases or disorders of the nervous system, such as Alzheimer's disease, Parkinson's disease, depression, Multiple Sclerosis, schizophrenia or the like; or other diseases or disorders; where the term "treatment" also includes prophylactic treatment, especially where the products manufactured according to the invention are used as nutraceuticals.

Pharmacological or nutraceutical formulations may be formulations of any type known in the art for macromolecules and/or small chemical entities.

The present invention thus relates also to pharmaceutical (this term here including nutraceutical or food supplement) compositions comprising a macromolecular of small chemical entity product manufactured by a process according to the invention as active ingredient. Especially preferred are compositions for enteral, especially oral, nasal, rectal or the like, or parenteral administration, e.g. by injection or infusion. The compositions comprise the active ingredient on its own or, preferably, together with a pharmaceutically acceptable carrier. The dose of the active ingredient depends on the disease to be treated, and on the species, age, weight and individual condition, as well as the method of administration.

Preferred is a pharmaceutical composition that is suitable for administration to a warm-blooded animal, especially man, suffering from a disease that responds to an active ingredient manufactured in accordance to the invention in a therapeutically or prophylactically advantageous way; for example a disorder of disease as mentioned above; comprising an amount of the active ingredient, or of a salt thereof if salt-forming groups are present, that is effective in the beneficial modulation said disorder or disease, preferably in the treatment or prophylaxis of the disease or disorder, together with at least one pharmaceutically acceptable carrier.

The pharmaceutical compositions comprise from approximately 0.0001% to approximately 95% active ingredient, dosage forms that are in single dose form preferably comprising from approximately 0.001% to approximately 20% active ingredient, and dosage forms that are not in single dose form preferably comprising from approximately 0.001% to approximately 10% active ingredient. Unit dose forms, such as dragées, tablets, ampoules or capsules, comprise from approximately 0.0005 mg to approximately 0.5 g of the active ingredient, preferably from 0.005 mg to approximately 20 mg.

The pharmaceutical compositions of the present invention are prepared in a manner known per se, for example by means of conventional mixing, granulating, confectioning, dissolving or lyophilising processes. For example pharmaceutical compositions for oral administration can be obtained by combining the active ingredient with one or more solid carriers, where necessary granulating a resulting mixture and processing the mixture or the granules, if desired or appropriate with the addition of further excipients, to form tablets or dragée cores.

Suitable carriers are especially fillers, such as sugars, e.g. lactose, saccharose, mannitol or sorbitol, cellulose preparations and/or calcium phosphates, e.g. tricalcium phosphate or calcium hydrogen phosphate, and binders, such as starches, e.g. corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, and also carboxymethyl starch, crosslinked polyvinylpyrrolidone or alginic acid or a salt thereof, such as sodium alginate. Additional excipients are especially flow conditioners and lubricants, e.g. silicic acid, talc, stearic acid or salts thereof, such as magnesium or calcium stearate, and/or polyethylene glycol, or derivatives thereof. For vaccines, adjuvants may be useful or required, e.g. Freund's Adjuvant, Immunostimulatory omplexes (ISCOMS), CpG dinucleotides comprising oligonucleotides, bacterial toxins, such as cholera toxin, heat labile enterotoxin or protein A, or monophosphoryl lipid A (LPS).

Dragée cores may be provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, e.g. for identification purposes or to indicate different doses of active ingredient.

Orally administrable pharmaceutical compositions are also dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talcum or magnesium stearate, and, where appropriate, stabilisers. In soft capsules, the active ingredient is preferably dissolved or suspended in suitable liquid excipients, e.g. fatty oils, âLauroglycol (Gattefossé S. A., Saint Priest, France), âGelucire (Gattefossé S. A., Saint Priest, France) or sesame oil, paraffin oil or liquid polyethylene glycols, such as PEG 300 or 400 (Fluke, Switzerland), or polypropylene glykols, to each of which stabilisers or detergents may also be added.

Other oral forms of administration are, for example, syrups prepared in customary manner that comprise the active ingredient e.g. in suspended form and in a concentration of approximately from 0.001% to 20%, preferably approximately 0.001% to about 2%, or in a similar concentration that provides a suitable single dose when administered, for example, in measures of 5 or 10 ml. Also suitable, for example, are powdered or liquid concentrates for preparing shakes, e.g. in milk. Such concentrates can also be packed in single-dose quantities.

Transdermal Delivery Systems are possible, especially with neutral active ingredients according to the invention. Suitable formulations comprise, for example, about 0.0001% to about 2% by weight of active ingredient. In a preferred aspect, there are provided formulations which comprise about 2% to 99.9999% (or the balance to 100%) of a short chain aliphatic alcohol. Suitable alcohols include ethanol, isopropanol, propylene glycol and glycerol. In a more preferred aspect, these formulations may additionally comprise a flux enhancer. Suitable flux enhancers include, for example, decylmethylsulfoxide, dimethylsufoxide as well as cyclic ketones, lactones, anhydrides and esters. Some of these flux enhancers also increase retention of the active ingredient and thus act to increase the concentration of it in the skin itself. For formulations for direct (local) treatment, such as topical application to the skin, it is preferred to use a flux enhancer which not only maximizes transdermal flux, but increases retention of the active ingredient in the skin. Certain cyclic ketone and lactone enhancers have been reported to increase local retention as well and, thus, comprise a preferred class of enhancers for topical administration of the active ingredient. In formulations for systemic treatment, it is preferable to use a flux enhancer which maximizes flux with a minimal local retention of the active ingredient.

Suitable rectally administrable pharmaceutical compositions are e.g. suppositories that consist of a combination of the active ingredient with a suppository base. Suitable suppository bases are e.g. natural or synthetic triglycerides, paraffin hydrocarbons, polyethylene glycols or higher alkanols.

For parenteral administration (which is preferred) there are suitable, especially, aqueous solutions of an active ingredient in water-soluble form, e.g. in the form of a water-soluble salt, or aqueous injection suspensions that comprise viscosity-increasing substances, e.g. sodium carboxymethylcellulose, sorbitol and/or dextran, and, where appropriate, stabilisers. The active ingredient, where appropriate together with excipients, may also be in the form of a lyophilisate and may be made into a solution prior to parenteral administration by the addition of suitable solvents.

Solutions as used e.g. for parenteral administration may also be used as infusion solutions.

The invention relates also to a method of treating the above-mentioned pathological conditions. For this purpose, an active ingredient of the present invention, or a pharmaceutically acceptable salt thereof, may be administered prophylactically or therapeutically, preferably in an amount that is effective against the mentioned diseases, to a warm-blooded animal, e.g. man, requiring such treatment, preferably in the form of pharmaceutical compositions. The dose of the active ingredient depends on the species of the warm-blooded animal to be treated, its body weight, its age and individual status, individual pharmacokinetic circumstances, the disease to be treated and the application route. Preferably, for a body weight of approximately 70 kg a daily dose of from 0.001 mg to 1000 mg, e.g. from approximately 0.01 mg to approximately 100 mg, preferably from approximately 0.05 mg to approximately 50 mg, of the active ingredient is administered.

Proteins, e.g. antibodies, may be formulated as enteral, e.g. nasal, or preferably parenteral, e.g. injection or infusion, formulations.

The invention therefore also concerns pharmaceutical compositions a therapeutically or nutraceutically effective amount of a macromolecule produces according to the invention, e.g. an antibody, e.g. a recombinant antibody, or especially a monoclonal antibody, and a pharmaceutically or nutraceutically acceptable carrier. Preferred are pharmaceutical compositions for parenteral application. Compositions for intramuscular, subcutaneous or intravenous application are e.g. isotonic aqueous solutions or suspensions, optionally prepared shortly before use from lyophilized or concentrated preparations.

Suspensions in oil may contain as oily component the vegetable, synthetic or semi-synthetic oils customary for injection purposes. The pharmaceutical compositions may be sterilized and contain adjuncts, e.g. for conserving, stabilizing, wetting, emulsifying or solubilizing the ingredients, salts for the regulation of the osmotic pressure, buffer and/or compounds regulating the viscosity, e.g. sodium carboxycellulose, carboxymethylcellulose, sodium carboxymethylcellulose, dextran, polyvinylpyrrolidine or gelatine.

The pharmaceutical compositions of the invention of macromolecules may comprise from approximately 0.001% to approximately 50% of active ingredients. They may be in dosage unit form, such as ready-to-use ampoules or vials, or also in lyophylized solid form.

In general, the therapeutically effective dose for mammals is between approximately 0.5 μg and 25 μg of a macromolecule manufactured according to the invention or of a monoclonal antibody of the invention per kg body weight depending on the type of macromolecule, the status of the patient and the mode of application. The specific mode of administration and the appropriate dosage will be selected by the attending physician taking into account the particulars of the patient, the state of the disease, the type of tumor treated, and the like. The pharmaceutical compositions of the invention are prepared by methods known in the art, e.g. by conventional mixing, dissolving, confectioning or lyophilizing processes.

Pharmaceutical compositions for injection are e.g. processed, filled into ampoules or vials, and sealed under aseptic conditions according to methods known in the art.

Among the systems useful for the manufacturing process and the other embodiments of the invention in cell culture systems or cell free biosynthetic systems, especially in cell culture systems, there may be mentioned inter alia the following:

Many systems are known for cell culture manufacture, e.g. using high-density growth, fed-batch or dialysis processes.

Among the possible organisms (also collectively referred to as "microorganisms" hereinafter, although this word is usually used in a different sense in biology)) useful in the processes and methods according to the invention, bacterial cells
(including mycoplasms) such as *Escherichia coli, Corynebacterium glutamicum, Bacillus megaterium*, bacteria of the genus *Brevibacterium* such as *B. ketoglutamicum, B. linens* or *B. paraffinolyticum, Burkholderia* species such as *B. glutamicum*, bacteria from the genus *Bacillus*, e.g. *Bacillus subtilis, Bacillus megaterium, Bacillus lichenifonnis* or *Bacillus brevis*, lactic acid bacteria or other bacteria, e.g. *Streptomyces lividans, Ralstonia eutrophia, Pseudomonas fluorescens* or *Staphylococcus carnosus* may be employed with advantage.

The selection of an appropriate system depends on factors known in the art, e.g. using a system providing correct signal peptide cleavage if required, proper proteolytic processing, proper acylation, e.g. palmitoylation or myristoylation, amidation, carboxymethylation, phosphorylation, N- and/or O-glycosylation, disulfide bridge formation, prenylation, proper folding of macromolecules and the like. The corresponding systems are known to the person skilled in the art.

Macromolecules according to the invention can be produced in cell culture or cell free systems, preferably in cell culture, e.g. by using their natural genes or after transformation with nucleic acids.

Nucleic acids are preferably DNA or RNA (in general, oligo- or polynucleotides).

Isolated nucleic acids coding for a macromolecule obtainable according to the invention, especially recombinant nucleic acids, are preferably obtained and defined as follows:

A nucleic acid, especially a gene, coding for a macromolecule obtainable according to the invention can, for example, be obtained by identifying at least a part of the sequence of an isolated macromolecule (protein), deducing DNA sequences coding for the partial protein sequence, preparing an oligonucleotide or a mixture of oligonucleotides (taking into consideration the degeneracy of the genetic code) as probe(s), probing a DNA library derived from the microbial strain naturally expressing the macromolecule (the term DNA library also including a "cDNA-library"), isolating the gene, and cloning it into a suitable vector for transformation of the microorganism or cell to be genetically modified. All these methods (especially those depicted below for identification of, transformation with and expression of nucleic acids coding for an enzyme of the invention) are standard practice, e.g. as described in Sambrook et al., Molecular Cloning—A Laboratory Manual, $2^{nd}$ edition, Cold Spring Harbor Press, 1989, or in in Gassen et al., "Gentechnische Methoden—Eine Sammlung von Arbeitsanleitungen für das molekularbiologische Labor", Spektrum Akademischer Verlag, Heidelberg 1999, in F. M. Asubel (Hg.) "Short Protocols in Molecular Biology", $3^{rd}$ ed., New York, Wiley 1997; or in Asubel et al., "Current Protocols in Molecular Biology", Vol. 1-3, Greene Publishing Associates and Wiley-Interscience, New York, 1987.

The partial sequencing of a protein to be manufactured or obtainalble according to the invention is, for example, made using selective endoproteases for selective digestion, e.g. endo-protease Lys-C, endoprotease Glu-C, chymotrypsin, thermolysin or preferably trypsin (cleaving C-terminally from the basic amino acids arginine or lysine) and, after separation, e.g. electrophoretically on a gel or by chromatography (e.g. HPLC), determining the terminal sequences of the resulting peptides, e.g. by exopeptidases, e.g. carboxypeptidases, such as carboxypeptidase A, B or P). An example is (e.g. tryptic) digestion, then MS/MS analysis (TOF).

DNA libraries can also be obtained by PCR methods.

A cDNA library (obtainable e.g. after extraction of the mRNA from the cells, transformation into DNA using reverse transcriptase, introduction of sticky ends, introduction into a cloning vector, and introduction of that vector into an appropriate host cell, e.g. a plasmid vector into a bacterium, such as a bacteriophage λ vector or a cosmid into E. coli, a yeast artificial into a yeast, such as Saccaromyces cerevisiae, a Pichia-pastoris vector into Pichia pastoris, or the like) or a DNA library (e.g. obtainable from selective digests of isolated DNA with restriction endonucleases, especially of type II, e.g. Alu I, Bam HI, Bgl I, Bst I, Eco RI, Eco RII, Fok I, Fnu DI, Hae II, Hae III, Hind III, Hind III, Hpa I, Msp I, Not I, Pst I, Sac I, Sal I, Sau 3A, Sma I, Taq I, Xho I, Xma I or as mentioned in the examples; if necessary, filling up recessed termini with Klenow fragment of E. coli DNA polymerase I, then ligating, e.g. with bacteriophage T4 DNA ligase, into a bacteriophage λ or cosmid vector for expression in E. coli or into a yeast artificial chromosome vector for expression in yeast) of the genomic DNA of the microorganism from which the enzyme of the invention can be isolated is then screened by stringent hybridization for matching polynucleotides (for appropriate conditions for stringent hybrid-disation see, for example, Sambrook et al., loc. cit., chapter 9) using (radioactive or fluorescence labeled) probes deduced from the known peptide fragments based on the genetic code which are produced according to standard procedures (fully degenerate, partially degenerate or using "guessmers"), which polynucleotides can then be isolated (e.g. from agar gels or the like) and sequenced. Longer nucleotides can be separated e.g. using pulsed field electrophoresis.

Hybridization is done using standard procedures, if necessary removing possible disturbing non-coding sequences, e.g. by PCR amplifying only the desired sequence parts or by endonuclease digestion, e.g. using dot blots of colonies of microorganisms from the DNA library. The positive clones can then be isolated.

The sequencing is done using standard procedures, e.g. the Maxam-Gilbert or the Sanger method.

If necessary, by combination of overlapping partial sequences the complete sequence coding for a macromolecule obtainable according to the invention (or one subunit thereof, if more than one polypeptide form the complete macromolecule) can be determined.

From this sequence, the corresponding amino acid sequence of the enzyme is (or, if more than one polypeptide forms it, the subunits thereof, the amino acid sequences are) easily determined, using the genetic code.

In another approach, the full amino acid sequence of the macromolecule obtainable according to the invention can be determined (e.g. by different endopeptidase digests and matching of overlapping sequenced partial peptides) and a DNA coding the protein can be produced synthetically. It is also very easily possible to screen a suitable DNA library in a host, e.g. E. coli, for expression of temperature resistant alcohol dehydrogenase activity to obtain a transformed clone expressing the biocatalyst. Still another method makes use of antibodies against a macromolecule obtainable according to the invention that can be obtained using standard procedures (up to and including the production of monoclonal antibodies obtained from myelomas obtained according to standard procedures) in order to isolate the ribosomes carrying the mRNA coding for the enzyme, transforming it into the corresponding DNA (e.g. with reverse transcriptase) and sequencing or genetically engineering the resulting macro-molecule.

A nucleic acid useful according to the invention is preferably present in isolated form or in recombinant form (then also in a microorganism, see below).

A nucleic acid useful according to the invention may also comprise modified (especially recombinant, but also naturally occurring) nucleic acids where, when compared with the form sequenced as described above, one or more nucleic acids are deleted, inserted, exchanged or added terminally, as long as the polypeptide or polypeptides for which they code still displays the desired function.

Terminal additions may comprise the addition of sequences for vectors or host nucleic acids into which the coding sequence may be combined.

More preferably, the modified nucleic acids are modified such as to code for a macromolecule obtainable according to the invention, obtained e.g. by recombinant technology (resulting in a recombinant nucleic acid) or alternatively from natural sources, where the amino acid sequence of the macromolecule comprises deletions, insertions, terminal additions or exchanges (especially conservative exchanges, e.g. of lipophilic against lipophilic, basic against basic, acidic against acidic, polar against polar amino acids, or the like) of amino acids (preferably of up to 20, in case of terminal additions up to 1000; more preferably of up to 5, in case of terminal additions of up to 200 amino acids, respectively), or any combination of such changes, when compared to the sequence of the macromolecule as known from the literature or found in a natural organism, as long as the basic activity is still present.

Most preferably, the modified nucleic acids contain 1 to 50, more preferably 1 to 12, additional nucleotides by insertion (especially additions yielding no frame shift), 1 to 50, more preferably 1 to 12 changes in nucleic acids, preferably resulting in conservative amino acid changes, and/or 1 to 50, more preferably 1 to 12, deletions of nucleotides, especially without frame shift.

The invention also relates to the manufacturing of probes, especially in radiolabelled or fluorescence labelled form, that are hybridizable under stringent conditions to genomic or cDNA or other nucleic acids coding and that code for the sequences of partial amino acid sequences, or for parts thereof, said probes preferably having a length of 6 to 24, more preferably of 12 to 21 nucleotides.

The embodiment of the invention relating to microorganisms transformed with a nucleic acid coding for a macromolecule obtainable according to the invention preferably relates to micro-organisms appropriate for expressing the gene, but also those that comprise the nucleic acid for pure conservation or replication purposes.

Appropriate microorganisms are named above.

The microorganisms, especially host cells, can be transformed with nucleic acids as such that code for a macromolecule obtainable according to the invention; however, usually they are transformed with suitable vectors, e.g. plasmids, cosmids, yeast artificial chromosome or the like, which may comprise partial sequences (e.g. useful in sequence determination) or total sequences for the macromolecule (e.g. useful in the expression and manufacture of the macromolecule).

Transformation of host cells is made according to standard procedures known in the art and appropriate for the respective host cells, e.g. according to the calcium chloride method, by electroporation, transformation after spheroblast formation into fungi, transformation with polyethylene glycol, transformation with lithium chloride, or the like. Virus or the like are modified by introduction of the sequences comprising the coding sequences for the enzyme of the invention.

Especially, the invention relates to the use of the microorganisms, especially host cells, in the production of said macromolecules.

Expression systems suitable for production of a macromolecule obtainable according to the invention are especially phage-based expression systems in bacteria, e.g. bacteriophage 2 or cosmids for *E. coli* as host, yeast artificial chromosomes for expression in Saccharromyces cerevisiae, the *Pichia pastoris* expression system used for expression in *Pichia pastoris*, expression systems in *Schizosaccaromyces pombe*, the baculovirus expression system or the like. In each of these systems, the nucleotide sequences coding for a macromolecule obtainable according to the invention can be expressed, either as such or with additional N- or C-terminal sequences, e.g. such that allow for direct export of the resulting polypeptide outside the expressing cells. These extra sequences, if disturbing the activity or otherwise not desired, can then be cleaved off using appropriate endoproteases known in the art.

Small chemical entities can be obtained from natural microorganisms, microorganisms selected according to standard selection methods or recombinant microorganisms. The latter may be transformed with nucleic acids expressing genes encoding one or more biocatalysts necessary for the biosynthesis of the desired products, e.g. single genes or gene clusters. The nucleic acids can otherwise be obtained and the cells transformed as described above.

Among the Culture Media to be used, any culture media known to the skilled person in the art as appropriate for the specific microorganism to be grown may be used. Among the possible media there are chemically defined media or media which comprise less defined components (e.g. hydrolysates of proteins, of yeast or the like), or combinations of such media.

Methods of culturing microorganisms as defined above include those described in standard textbooks such as "Mikrobiologische Methoden —Eine Einführung in grundlegende Arbeitstechniken (Microbiological Methods —An Introduction into Basic Working Techniques), Eckhard Bast, 2. edition, Spektrum Akademischer Verlag, Heidelberg/Berlin 2001, or "Basic Methods in Antibody Production and Characterization, G. C. Howard and D. R. Bethell (eds.), CRC Press, Boca Raton, London, New York and Washington, D.C., 2001), D.C. Darling and S.J. Morgan, John Wiley & Sons, Ltd, US, 1994; Culture of Animal Cells: A Manual of Basic Technique, R. Ian Freshney, Wiley & Sons, 5th ed., 2005; Plant Cell Culture (Methods Express Series), Arthur Kornberg, Scion Publishing Ltd (Dezember 2008); Cell Culture Technology for Pharmaceutical and Cell-Based Therapies (Biotechnology and Bioprocessing), Sadettin Ozturk and Wei-Shou Hu (eds.), Marcel Dekker Inc; Auflage: illustrated edition (19, September 2005); Bacterial Cell Culture: Essential Data, A. S. Ball, John Wiley & Sons Ltd (1997); Cell Culture Manual 2008-2009, $3^{rd}$ edition, Sigma-Aldrich or the like, all of which are incorporated by reference herewith concerning the culturing methods and media used.

Among the possible hosts and culture conditions, the following may be mentioned:

| Host organism | Production strains | Media | Culture conditions |
|---|---|---|---|
| *Escherichia coli* | K-12, W3110, HB101, BL21, BL21 (DE) and derivatives, Origami | Complex such as Luria Bertani Broth (Bertani G 1951 J. Bacteriol. 62: 293-300) Mineral media with glucose or glycerol as carbon source (D J Korz et al 1995 J Biotechnol 39: 59-65 | High-cell density cultivation as fed-batch process Mostly intracellular expression |
| *Bacillus* | B. subtilis, B. megaterium, B. licheniformis | Complex such as Luria Bertani Broth (Bertani G 1951 J. Bacteriol. 62: 293-300) Mineral medium with glucose (A Martinez et al 1997 Appl Microbiol Biotechnol 47: 40-45) | High cell density cultivation Mostly secretory production |
| *Pichia pastoris* | GS115 (mut$^+$), KM71 (mut$^s$), SMD1163 (protease deficient) | Semicomplex media with tryptone, yeast nitrogen base and glycerol/methanol as carbon source | High cell censity cultivation in fedbatch mode Secretory production |
| *Sacharomyces cerevisiae* | | Complex such as Luria Bertani Broth (Bertani G 1951 J. Bacteriol. 62: 293-300) Mineral medium with glucose (C. Verduyn et al, 1992, Yeast 8: 501-517 | Batch and High cell density fed batch processes Intracellular and secretory production |
| *Aspergillus* | A. niger, A. nidulans, A. oryzae, A. sojae | Mineral media supplemented with peptone, tryptone | Submerged and solid-state fermentation |

The additives useful according to the invention, namely the one or more obligatory compounds selected from sterically hindered nitroxyls, sterically hindered hydroxylamines, sterically hindered hydroxylamine salt compounds, sterically hindered amino compounds and sterically hindered N-hydrocarbyloxyamines, are preferably added in a concentration in the range totalling from 0.0001 to 10% by weight of the complete culture or cell free medium (including its solvent(s)), in one other embodiment from 0.001 to 9% by weight, in another embodiment from 0.005 to 8% by weight, in another embodiment from 0.008 to 7% by weight, in yet another embodiment in the range from 0.01 to 5% by weight or especially 0.002 to 1% by weight.

If one or more (optional) other antioxidants or radical scavengers, such as benzofuranone compounds, nitrones, (preferably sterically hindered) phenol antioxidants natural antioxidants or radical scavengers or coumestanes; or a mixture of two or more of these additives, are added to the medium, their concentration preferably also (independently of that of the obligatory compound(s)) in the complete medium preferably lies in the range totalling from 0.0001 to 10% by weight, in one other embodiment from 0.001 to 9% by weight, in another embodiment from 0.005 to 8% by weight, in another embodiment from 0.008 to 7% by weight, in yet another embodiment from 0.01 to 6% by weight.

In the case of a cell culture or cell free preparation in solid form that comprises one or more radical scavenging and/or antioxidative additives selected from the group consisting of sterically hindered nitroxyls, sterically hindered hydroxylamines, sterically hindered hydroxylamine salt compounds, sterically hindered amino compounds and sterically hindered N-hydrocarbyloxyamines as obligatory compound(s), the one or more obligatory compounds are preferably included in a concentration in the range totalling from 0.0005 to 30% by weight of the dry complete culture or cell free medium, in one other embodiment from 0.005 to 25% by weight, in another embodiment from 0.01 to 12% by weight, in another embodiment from 0.02 to 10% by weight, in yet another embodiment in the range from 0.01 to 8% by weight.
without or with addition of one or more other antioxidants or radical scavengers, such as benzofuranone compounds, nitrones, (preferably sterically hindered) phenol antioxidants natural antioxidants or radical scavengers or coumestanes; or a mixture of two or more of these additives; where the additives may be present in free and/or in salt form.

In a (dry) medium for cell culture, or a main component of a cell culture medium (in dry form), the one or more obligatory compounds are preferably included in a concentration in the range totalling from 0.0005 to 30% by weight of the dry complete culture or cell free medium, in one other embodiment from 0.005 to 25% by weight, in another embodiment from 0.01 to 12% by weight, in another embodiment from 0.02 to 10% by weight, in yet another embodiment in the range from 0.01 to 8% by weight, without or with addition of one or more other antioxidants or radical scavengers, such as benzofuranone compounds, nitrones, (preferably sterically hindered) phenol antioxidants natural antioxidants or radical scavengers or coumestanes; or a mixture of two or more of these additives; where the additives may be present in free and/or in salt form.

In both preceding paragraphs, the optional antioxidants or radicals scavengers may be present in comparable amounts as given for the obligatory compound(s).

For isolation, it is possible to isolate a product by disrupting cells, e.g. from cytoplasmic inclusion bodies, or as periplasmic products (which e.g. show appropriate disulfide bridging and/or appropriate secretion signals) or after secretory release out of the microorganisms from the culturing medium.

The isolation or purification may be performed in the absence or in the presence of one or more (obligatory) compounds selected from sterically hindered nitroxyls, sterically hindered hydroxylamines, sterically hindered hydroxylamine salt compounds, sterically hindered amino compounds and sterically hindered N-hydrocarbyloxyamines to achieve protection against radicals and oxidative stress where useful, with the addition of one or more other (optional) antioxidants and/or radical scavengers.

Isolation and purification methods may include initial bulk extraction, other extraction methods e.g. with aqueous and/or hydrophobic solvents (including ionic liquids and/or standard solvents), supercritical fluid extraction (e.g. with $CO_2$), salting out (e.g. with ammonium sulphate), solvent partition techniques, size exclusion chromatography, ion exchange chromatography, reversed phase chromatography, hydrophobic chromatography, affinity chromatography, countercurrent chromatography, chiral chromatography or other chromatographic techniques, including low pressure, medium pressure or high pressure liquid chromatography, dialysis, precipitation, such as crystallization, e.g. from solutes or emulsions, electrophoresis, such as gel electrophoresis, zonal electrophoresis, gradient gel electrophoresis, isoelectric focussing, 2D electrophoresis, electroblotting, capillary electrophoresis or the like, filtering, immunological techniques, such as immunoprecipitation or immune agglutination, centrifugation, Western blotting, Eastern blotting, Southern blotting, Northern blotting, concentration (e.g. by solvent evaporation), desalting, hybridisation methods for nucleic acids, phenol extraction, ethanol precipitation of nucleic acids, restriction cleavage, pulsed field gel electrophoresis, dot blotting, slot blotting, electroelution, polymerase chain reaction, or the like, or combinations of two or more these techniques, all of which are known to the person skilled in the art. The scale of the methods depends on whether individual molecules (e.g. specific nucleic acids or antibodies or the like for single patient treatment e.g. in the case of "personal medicine") or mass products (such as vitamins, vaccines or the like) have to be obtained. Examples for description of appropriate methods can be found, for example, in:

Natural Products Isolation (Methods in Biotechnology), Satyajit D. Sarker (ed.), Humana Press; 2nd edition (2005); Isolation and Purification of Proteins (Biotechnology and Bioprocessing Series), Rajni Hatti-Kaul and Bo Mattiasson (eds.), CRC, 1st edition (2003); Recombinant Protein Protocols: Detection and Isolation (Methods in Molecular Biology), Rocky S. Tuan (ed.), Humana Press; 1st edition (1997); Protein Purification Protocols (Methods in Molecular Biology), Paul Cutler (ed.), Humana Press; 2nd edition (2003); Nucleic Acids Isolation Methods (Paperback), B. Bowien, American Scientific Publishers (2003); Nucleic Acid Isolation and Purification; (Paperback), Boehringer Mannheim (1998); Handbook of Nucleic Acid Purification (Hardcover), Dongyou Liu (ed.), CRC; 1 edition (2009); Laboratory Techniques in Biochemistry and Molecular Biology, Volume 3, Part 2, Techniques of Lipidology: Isolation, Analysis and Identification of Lipids (Vol 3) (Paperback), Morris Kates, Elsevier Science Ltd; 2 Revised edition (December 1986); Microbial Production of L-Amino Acids (Advances in Biochemical Engineering/Biotechnology), Robert Faurie and Jürgen Thommel (eds.), Springer; 1st edition (2003).

Among the possible purification methods for the products obtainable according to the invention, the following may be mentioned:

TABLE

Purification methods for bioproducts

| Product type | Purification method |
| --- | --- |
| Polysaccharides | Concentration, precipitation with solvents |
| Lipids | Extraction, milling, pressing |
| Nucleic acids | Adsorption, precipitation |
| Proteins | Adsorption chromatography (Ion exchange, affinity, hydrophobic interaction), gel permeation chromatography |
| Organic acids/ amino acids | Precipitation, crystallisation, extraction, adsorption on e.g. ion exchange resins |
| Alcohols | Distillation, extraction |
| Vitamins | Extraction, adsorption |

Where it is desired to enhance the quantity and/or the quality of a product obtainable according to the present invention over that without the presence of the additives according to the invention, the quality can be determined e.g. in terms of purity, specific activity, molecular integrity or the like, or combinations of such parameters, while the quantity can be determined as yield, e.g. yield per liter of medium, or the like, according to standard procedures known in the art, respectively.

All references mentioned within the present disclsoure are preferably included by reference herein concerning the methods referred to therein, without that this is intended to mean that they are relevant prior art for the present invention.

The following examples are intended to illustrate the invention without limiting its scope.

If not mentioned, the antioxidant(s) used (also called stabilizers in the Examples) are added in the medium in a final concentration of 5 mM.

EXAMPLE 1

Expression of Green Fluorescent Protein in Escherichia coli JM109 in Shake Flask Cultivation in Mineral Medium Cultivation Precultures are prepared in 250 mL baffled shake flasks containing 25 mL sterile mineral medium [macronutrients in g/L: Glycerol (25), $(NH_4)_2$-citrate (1.0), $Na_2HPO_4$ $2H_2O$ (9.0), $KH_2PO_4$ (1.82), $NH_4Cl$ (1.52), $MgSO_4$ (0.12), $(NH_4)_2SO_4$ (0.6); Ampicillin (100 µg/L); micronutrients in mg/L: $Na_2$-EDTA (8.4), thiamine (4.5), Fe(III) citrate (12.5), $Na_2MoO4$ $2xH_2O$ (2.5), $H_3BO_3$ (3), $CoCl_2$ $6xH_2O$ (2.5), $CuSO_4$ $5xH_2O$ (0.45) $MnCl_2 4xH_2O$ (15), $ZnCl_2$ (8) adjusted to pH 7.0]. Cultures are inoculated with 250 µL of a glycerol stock stored at −80° C. of E. coli JM109 (Promega Inc, Wallisellen, C H; Genotype: endA1, recA1, gyrA96, thi, hsdR17 ($r_k^-$, $m_k^+$), re/A1, supE44, Δ(lac-proAB), [F'' traD36, proAB, laql$^q$ZΔM15]) harboring the plasmid pBAD-GFPuv (Biorad Inc., Reinach, C H; Genbank U62637.1, containing the GFPuv gene under control of the ara promoter; GFP=Green Fluorescent Protein). Precultures are incubated at 37° C. for 10-12 h.

Experimental cultures are performed in a volume of 25 mL of the above described medium in 250 mL baffled shake flasks. Stabilizers according to the invention are added to a final concentration of 5 mM as indicated from sterile stock solutions. Cultures are started by inoculating with the preculture to an optical density at 600 nm ($OD_{600}$) of 0.25. Growth of the culture is monitored by reading optical density at 600 nm. Cultures are induced by adding L-arabinose to a final concentration of 0.2% (w/v) when the $OD_{600}$ reaches 0.5. Samples of 1 mL are taken 6 and 20 h after induction for $OD_{600}$ reading and GFP quantification. For GFP quantification 1 mL of the culture is harvested after 2-4 h and after 20 h after induction. Cells are collected by centrifugation at 16 000 g and the cell pellet is stored at −20° C. for further analysis.

Analytics

The measurement of GFP expression by whole cell fluorescence measurements follows the procedure of Scholz et al. (Eur. J. Biochem., 2000,267, 1565-1570). Frozen cell pellets are thawed, resuspended in 1 mL PBS [NaCl (8 g/L), KCl (0.2), of $Na_2HPO_4$ (1.44), $KH_2PO_4$ (0.24), adjusted to pH 7.4] and subsequently diluted to an optical density of 0.1. GFP fluorescence of whole cells is measured in a Eclipse Fluorometer (Varian) with an excitation wavelength of 400 nm and an emission wavelength of 512 nm. Specific relative fluorescence [RFU/$OD_{600}$] is calculated by dividing the relative fluorescence emmision units by the optical density of the suspension at 600 nm.

Results and conditions are given in the following table:

TABLE 1

Effect of additives on growth and GFPuv expression in E. coli JM109 (Values are the mean of two separate determinations taken 20 h after inoculation)

| | Additives | Growth (Final $OD_{600}$) | GFP expression (Relative fluorescence unit*$OD_{600}^{-1}$) |
|---|---|---|---|
| Experiment 1 | Control, no additive | 13.7 | 0 |
| | 4-Hydroxy-2,2,6,6-tetramethyl-piperidine AND Vitamin C | 11.8 | 216 |
| | 4-Hydroxy-2,2,6,6-tetramethyl-piperidine AND 3,5-di-tert-butyl-4-hydroxy-hydrocinnamic acid | 13.8 | 5750 |
| Experiment 2 | Control, no additive | 11.0 | 1423 |
| | 4-Hydroxy-2,2,6,6-tetramethylpiperidin-1-oxyl | 9.5 | 7276 |
| | 4-Hydroxy-2,2,6,6-tetramethyl-piperidine | 10.9 | 1646 |
| Experiment 3 | Control, no additive | 10.4 | 1189 |
| | Tris(tetramethylhydroxypiperidinol) citrate (TINOGARD QS) | 11.4 | 2675 |

These data demonstrate that shake flask experiments show a general trend that addition of nitroxides +/− antioxidants result in an increase of GFP expression.

EXAMPLE 2

Expression of Green Fluorescent Protein in Escherichia coli BL21 (DE3) in Shake Flask Cultivation in Complex Medium Cultivation Precultures are prepared in 250 mL baffled shake flasks containing 25 mL sterile LB medium [Tryptone (10.0 g/L), yeast extract (5.0), NaCl (10.0), kanamycin 30 (mg/L); adjusted to pH 7.0 with NaOH]. Cultures are inoculated with 250 µL of a glycerol stock stored at −80° C. of E. coli BL21 [Novagen, Madison, USA; Genotype: E ompT hsdS$_B$ ($r_B^-$ $m_B^-$) gal dcm (DE3)] harboring the plasmid pET28a-GFPuv which is obtained by inserting the GFPuv gene (isolated from pBAD-GFPuv through PCR) into the EcoRI site of pET28a (Novagen, Madison, USA) which placed the GFPuv gene under the control of the T7/Lac promotor system. Precultures are incubated at 37° C. for 10-12 h.

Experimental cultures are performed in a volume of 25 mL of the above described medium in 250 mL baffled shake flasks. Stabilizers are added to a final concentration of 5 mM as indicated from sterile stock solutions. Cultures are started by inoculating with the preculture to an $OD_{600}$ at 600 nm of 0.25. Samples are taken for $OD_{600}$ measurements. Cultures are induced by adding IPTG (Isopropyl-β-D-thiogalactoside) to a final concentration of 0.5 mM when the OD600 reaches 0.5. Samples of 1 mL are taken after induction for $OD_{600}$ reading and GFP quantification. For GFP quantification 1 mL of the culture is harvested after 2-4 h and after 20 h after induction. Cells are collected by centrifugation at 16 000 g and the cell pellet is stored at −20° C. for further analysis. Analysis of in vivo GFP fluorescence is performed by the method described in Example 1.

TABLE 2

Effect of additives on GFPuv expression in *E. coli* BL21 in batch mode in shake flask culture (Values are the mean of two separate determinations taken 20 h after induction)

| | Additives | Growth (Final OD$_{600}$) | GFP expression (Relative fluorescence unit*OD$_{600}^{-1}$) |
|---|---|---|---|
| Experiment 1 | Control, no additive | 3.4 | 584 |
| | 4-Hydroxy-2,2,6,6-tetramethylpiperidin-1-oxyl | 2.4 | 1909 |
| Experiment 2 | Control, no additive | 3.3 | 195 |
| | 4-Hydroxy-2,2,6,6-tetramethylpiperidin-1-oxyl | 2.61 | 319 |
| | 1,4-dihydroxy-2,2,6,6-tetramethylpiperidine | 3.19 | 222 |

That also 1,4-dihydroxy-2,2,6,6-tetramethylpiperidine shows at least some effect and is not detrimental, supports the view that the nitroxyls and their respective amines can both be used as they are modified to each other in the cultures.

EXAMPLE 3

Expression of Green Fluorescent Protein in *E. Coli* JM109 in High Cell Density Fed-Batch Cultivation in Mineral Medium Precultures A first preculture of *E. coli* JM109 harboring the plasmid pBAD-GFPuv is initiated from glycerol stocks stored at −80° C. in 3 mL of LB medium containing 0.01% (v/v) Antifoam A (Fluka). After growth for 10-12 h it is used to seed 2×100 mL of mineral medium (as described in Example 1) containing 0.01% Antifoam A (silicone fluid containing a suspension of finely powdered silica to enhance its defoaming efficiency; Dow Corning Corporation, Midland, Mich., USA), in 1 L baffled shake flasks. After 10-12 h this culture is centrifuged resuspended in 50 mL mineral medium and is used to inoculate the main culture.

Fedbatch Culture

Cultivation is performed in BioFlow110 bioreactors (Total volume 2.2 L; New Brunswick Scientific, Nürtingen, Germany) filled with 1 L of mineral medium plus 0.01% (v/v) Antifoam A for the batch phase. Reactors are equipped with pH, pO$_2$ and foam probes, mass flow controllers to control gas flow and ratio of air and pure oxygen and pumps for automated dosage of base (14% [v/v] aqueous NH$_3$), antifoam (25% [v/v] Antifoam A) and nutrient feed solution. The agitation is set to 500 rpm and air is supplied at a gas flow rate of 2 L/min. The fedbatch culture is incoculated to an OD$_{600}$ of 0.25-0.5 and allowed to grow unlimited with a specific growth rate of ~0.5 h$^{-1}$. Growth is monitored by measuring OD$_{600}$. When the disolved oxygen concentration decreases to 30%, automated adjustment of the air:oxygen ratio in the gas mix is started to control dO$_2$ to 30% using a PID loop. When the gas mix consisted of 100% oxygen a further increase in oxygen transfer is achieved through increasing the agitation rate up to a maximum level of 1200 rpm. When glycerol in the batch medium is completely consumed, as indicated by a distinct drop of pure oxygen in the gas mix, feeding solutions (first containing 70 g/L glycerol and later as cell density increased 200 g/L glycerol in mineral medium) are pumped into the reactor by a predefined exponential fed scheme. The feeding rate is calculated to allow the cells to grow at a growth rate of approximately 0.15 h$^{-1}$. During the feeding phase dO$_2$ is also kept at 30%. 3-6 h after starting the feeding protein expression is induced by the addition of 0.2 (w/v) L-arabinose. Samples are taken every hour for OD$_{600}$ reading and to obtain cell pellets which are stored at −20° C. for further analysis. Analysis of in vivo GFP fluorescence is performed by the method described in Example 1.

TABLE 3

Growth and GFP expression in high cell density fedbatch cultivation of *E. coli* JM109

| Experiment | Additive | Optical density Value | Optical density Factor | GFP expression (RFU/OD$_{600}$) Value | GFP expression (RFU/OD$_{600}$) Factor | Process Time (h) |
|---|---|---|---|---|---|---|
| Experiment 1 | Control (=no additive) | 9.86 | 1 | 211 | 1 | 26.75 |
| | 4-Hydroxy-2,2,6,6-tetramethylpiperidin-1-oxyl | 11.86 | 1.20 | 535 | 2.53 | 26.75 |
| Experiment 2 | Control | 6.67 | 1 | 0 | 1 | 18 |
| | 4-Hydroxy-2,2,6,6-tetramethylpiperidin-1-oxyl | 11.42 | 1.7 | 190 | n.a. | 18 |
| Experiment 3 | Control | 18.56 | 1 | 1723 | 1 | 14 |
| | 4-Hydroxy-2,2,6,6-tetramethylpiperidin-1-oxyl AND Vitamin C | 21 | 1.13 | 2489 | 1.44 | 14 |
| Experiment 4a) | Control | 92.92 | 1 | 1781 | 1 | 18.5 |
| | 4-Hydroxy-2,2,6,6-tetramethylpiperidin-1-oxyl AND 3,5-di-tert-butyl-4-hydroxy-hydrocinnamic acid | 80.5 | 0.87 | 3309 | 1.86 | 18.5 |
| Experiment 4b) | Control | 78.8 | 1 | 1551 | 1 | 23.25 |
| | 4-Hydroxy-2,2,6,6-tetramethylpiperidin-1-oxyl AND 3,5-di-tert-butyl-4-hydroxy-hydrocinnamic acid | 74.12 | 0.94 | 2428 | 1.57 | 23.25 |
| Experiment 5 | Control | 11.9 | 1 | 0 | 1 | 22.3 |
| | 1,4-dihydroxy-2,2,6,6- | 38.4 | 3.23 | 2539 | n.a. | 22.3 |

TABLE 3-continued

Growth and GFP expression in high cell density fedbatch cultivation of *E. coli* JM109

| Experiment | Additive | Optical density Value | Factor | GFP expression (RFU/OD$_{600}$) Value | Factor | Process Time (h) |
|---|---|---|---|---|---|---|
| | tetramethylpiperidine AND Vitamin C | | | | | |
| Experiment 6 | Control | 10.3 | 1 | 1038 | 1 | 24.75 |
| | 4-Hydroxy-2,2,6,6-tetramethyl-piperidine | 24.7 | 2.39 | 5507 | 5.3 | 24.75 |
| Experiment 7 | Control | 56.4 | 1 | 5765 | 1 | 17 |
| | 4-Hydroxy-2,2,6,6-tetramethyl-piperidine | 57.1 | 1.01 | 6438 | 1.12 | 17 | n.a.—not applicable

This Example also shows that it is possible to combine other antioxidants such as 3,5-di-tert-butyl-4-hydroxycinnamic acid or vitamin C with the antioxidants belonging to the "obligatory" ones described above and in the claims as mentioned in the table.

EXAMPLE 4

Expression of Green Fluorescent Protein in *E. Coli* BL21 in High Cell Density Fed-Batch Cultivation in Mineral Medium Precultures

*E. coli* BL21 [Novagen, Madison, USA; Genotype: E ompT hsdS$_B$ (r$_B^-$ m$_B^-$) gal dcm (DE3)] harboring the plasmid pET28a-GFPuv was constructed as detailed in Example 2. A first preculture is initiated from glycerol stocks stored at −80° C. in 3 mL of LB medium containing 0.01% (v/v) Antifoam A (Fluke). After growth for 10-12 h it is used to seed 2×100 mL of mineral medium (as described in Example 1) containing 0.01% Antifoam A (silicone fluid containing a suspension of finely powdered silica to enhance its defoaming efficiency; Dow Corning Corporation, Midland, Mich., USA), in 1 L baffled shake flasks. After 10-12 h this culture is centrifuged, resuspended in 50 mL mineral medium and is used to inoculate the main culture.

Fedbatch Culture

Cultivation is performed in BioFlow110 bioreactors (Total volume 2.2 L; New Brunswick Scientific, Nürtingen, Germany) filled with 1 L of mineral medium plus 0.01% (v/v) Antifoam A for the batch phase. Reactors are equipped with pH, pO$_2$ and foam probes, mass flow controllers to control gas flow and ratio of air and pure oxygen and pumps for automated dosage of base (14% [v/v] aqueous NH$_3$), antifoam (25% [v/v] Antifoam A) and nutrient feed solution. The agitation is set to 500 rpm and air is supplied at a gas flow rate of 2 L/min. The fedbatch culture is inoculated to an OD$_{600}$ of 0.25-0.5 and allowed to grow unlimited with a specific growth rate of ~0.5 h$^{-1}$. Growth is monitored by measuring OD$_{600}$. When the dissolved oxygen concentration decreases to 30%, automated adjustment of the air:oxygen ratio in the gas mix is started to control dO$_2$ to 30% using a PID loop. When the gas mix consisted of 100% oxygen a further increase in oxygen transfer is achieved through increasing the agitation rate up to a maximum level of 1200 rpm. When glycerol in the batch medium is completely consumed, as indicated by a distinct drop of pure oxygen in the gas mix, feeding solutions (first containing 70 g/L glycerol and later as cell density increased 200 g/L glycerol in mineral medium) are pumped into the reactor by a predefined exponential fed scheme. The feeding rate is calculated to allow the cells to grow at a growth rate of approximately 0.15 h$^{-1}$. During the feeding phase dO$_2$ is also kept at 30%. 3-6 h after starting the feeding protein expression is induced by the addition of 0.2 (w/v) L-arabinose. Samples are taken every hour for OD$_{600}$ reading and to obtain cell pellets which are stored at −20° C. for further analysis. Analysis of in vivo GFP fluorescence is performed by the method described in Example 1.

TABLE 4

Time course of growth and GFP expression in in *E. coli* BL21 in high cell density fed-batch cultivation in mineral medium

| Cultivation time (h) | Time after induction (h) | OD 4-Hydroxy-2,2,6,6-tetra-methylpiperidin-1-oxyl | Control | Factor | RFU/OD 4-Hydroxy-2,2,6,6-tetra-methylpiperidin-1-oxyl | Control | Factor |
|---|---|---|---|---|---|---|---|
| 16.5 | 2.5 | 43.57 | 30.11 | 1.45 | 107.9 | 9.1 | 11.86 |
| 20.8 | 6.0 | 68.52 | 48.46 | 1.41 | 678.8 | 264.7 | 2.56 |
| 32.5 | 18 | 94.75 | 83.39 | 1.14 | 873 | 486.5 | 1.79 |

EXAMPLE 5

Expression of FimH-CRD in *Escherichia coli* HM 125 in Shake Flask Cultivation in Mineral Medium The effect of nitroxide-type additives on the expression of carbohydrate recognition domain of FimH 8FimH-CRD) is tested. FimH is a protein located at the tip the type I pillum formed by *E. coli*. In pathogenic bacteria pilli take part in the attachment of the pathogens to the host cells and pilli forming proteins are promising drug targets (Nishiyama et al. 2003. J Mol Biol 330: 513-525). The carbohydrate recognition domain of FimH comprises 156 amino acids at the N-terminus.

Cloning

Standard molecular techniques are used for the cloning of the FimH carbohydrate recognition domain (FimH-CRD). The plasmid pfimHs-trc, encoding FimH lectin domain (1-156 amino acids M. Vetsch P et. al. 2002—J. Mol. Biol. 322: 827-840), is kindly provided by R. Glockshuber (ETH Zürich, Switzerland). The FimH-CRD fragment is amplified by polymerase chain reaction using specific forward primer containing the restriction site NdeI and a specific reverse primer containing the thrombin cleavage site and the restriction site XhoI, respectively. The insert is ligated into the corresponding cloning site in pET21b. The resulting contrast is named pET21b-FimH-CRD.

Cultivation

Precultures are prepared in 25 mL sterile LB medium [Tryptone (10.0 g/L), yeast extract (5.0 g/L), NaCl (10.0 g/L), ampicillin 100 (mg/L); adjusted to pH 7.0 with NaOH]. Cultures are inoculated with a glycerol stock stored at −80° C. of the protease deficient strain $E.$ $coli$ HM125 (Meerman H J & Georgiou G. 1994. Biotechnology (NY) 2, 1107-1110) harboring the plasmid pET21b-FimH-CRD Vector. Precultures are incubated at 37° C. for 10-12 h. Experimental cultures are performed in a volume of 500 mL of modified M9 medium [$Na_2HPO_4 \times 7H_2O$ (12.8 g/L), $KH_2PO_4$ (3 g/L), NaCl (0.5 g/L), $NH_4Cl$ (1 g/L), D-glucose (4 g/L), $MgSO_4$ (0.12 g/L), $CaCl_2$ (0.01 g/L) and vitamins (in mg/L): riboflavin (0.1), choline chloride (1), folic Acid (1), niacinamide (1), p-amino benzoic acid (1), pyridoxal-HCl (1), thiamine-HCl (1), myo-Inositol (2)] supplemented with 100 mg/L ampicillin. Cultures are inoculated with 5 mL of the preoculture and grown at 30° C. and 150 rpm) until the optical density at 600 nm ($OD_{600}$) reached 0.8-1.0. Then 1 mM IPTG and the stabilizer(s) (obligatory additive) according to the invention are added to final concentrations of 5, 10 and 20 mM as indicated from sterile stock solutions and the cultures are grown overnight. Then the cells are cooled on ice for 5 min and harvested by centrifugation at 5'000 rpm for 20 min at 4° C. Cell are harvested by centrifugation and biomass is quantified by weighing the wet cell pellets. The pellet is suspended in a cold solution of 50 mM Tris-HCl, pH 7.5, 150 mM NaCl, 5 mM EDTA, 1 mg/mL polymyxin B sulfate and stirred for two hours at 4° C. After centrifugation at 11'000 rpm for 20 min at 4° C., the supernatant (periplasmic extract) is dialyzed overnight against 50 mM $NaH_2PO_4$, 300 mM NaCl and 10 mM imidazole, pH 8 (binding buffer) and applied to a Ni-NTA column (Sigma, Buchs, Switzerland) attached to a Bio-Logic fast protein liquid chromatography system (BioRad, Reinach BL, Switzerland). The column is washed with binding buffer and afterwards eluted with 50 mM $NaH_2PO_4$, 300 mM NaCl and 250 mM imidazole, pH 8 (elution buffer). Fractions containing FimH-CRD-Th-6H is are pooled and dialyzed against water and then against 20 mM HEPES, 150 mM NaCl and 1 mM $CaCl_2$, pH 7.4.

The concentration of protein is determined by HPLC method (Agilent 1100/1200 series) using BSA as standard (Sigma). The column Poros R1/10 10 µm (100×2 mm, Morvay Analytik) is kept at 60° C.; eluents are A: 0.1% trifluoroacetic acid (TFA) in $H_2O$ and B: 90% MeCN+0.09% TFA. A gradient of 20% B to 90% B is run within 20 min at a flow rate of 0.2 mL/min. The detection is monitored at 210 nm. Results are compiled in the following tables 5 and 6.

TABLE 5

Effect of 4-Hydroxy-2,2,6,6-tetramethylpiperidin-1-oxyl (TEMPO) on growth and expression of FimH in $E.$ $coli$ HM125 (Values are the mean of triplicate determinations)

|  | Control | TEMPO 5 mM | TEMPO 10 mM | TEMPO 20 mM |
|---|---|---|---|---|
| Cell pellet (g/L) | 7.99 ± 0.25 | 7.78 ± 0.45 | 7.44 ± 0.32 | 6.54 ± 0.2 |
| FimH (mg/L) | 6.48 ± 0.36 | 8.85 ± 0.21 | 8.61 ± 0.14 | 8.26 ± 0.54 |
| mg FimH/g cell | 0.81 | 1.14 | 1.15 | 1.26 |

The results show that expression of FimH is increased in the presence of the additive while cell growth is reduced.

TABLE 6

Effect of 1,4-dihydroxy-2,2,6,6-tetramethylpiperidine (TEMPOL) on growth and expression of FimH in $E.$ $coli$ HM125 (Values are the mean of triplicate determinations)

| Yield of | Control | TEMPOL 5 mM | TEMPOL 10 mM | TEMPOL 20 mM |
|---|---|---|---|---|
| Cell pellet (g/L) | 7.99 ± 0.25 | 8.22 ± 0.35 | 7.86 ± 0.25 | 7.94 ± 0.33 |
| FimH (mg/L) | 6.48 ± 0.36 | 9.1 ± 0.56 | 9.59 ± 0.49 | 10.08 ± 0.66 |
| mg FimH/g cell | 0.81 | 1.1 | 1.22 | 1.26 |

The results show that expression of FimH is increased in the presence of the additive and cell growth is unaffected by the additive.

The results further show that addition of the sterically hindered hydroxylamine gives a distinctly improved yield over addition of the sterically hindered nitroxyl.

The invention claimed is:

1. A process for manufacturing a product in a cell culture system comprising bacterial cells, the process comprising:
   adding at least one first additive selected from the group consisting of a sterically hindered nitroxyl, a sterically hindered hydroxylamine, a sterically hindered hydroxylamine salt compound, a sterically hindered amino compound, and a sterically hindered N-hydrocarbyloxyamine, -to a medium comprising a cell culture to produce a product from the cell in the cell culture, wherein the at least one first additive is added in an amount of 0.0001 to 10% by weight, based on a total weight of the culture; and
   optionally adding at least one second additive selected from the group consisting of selected from the group consisting of a benzofuranone compound, a nitrone, a phenol antioxidant, a natural antioxidant, a radical scavenger, and a coumestane to the medium,
   wherein a part or all of the process is carried out in the presence of the first additive or the first and second additives, and
   each additive may be present in free form, salt form, or both,
   wherein
   (i) the sterically hindered nitroxyl compound, sterically hindered hydroxylamine compound, sterically hindered hydroxylamine salt compound is of formulae IA, IB or IC

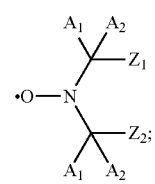

IA

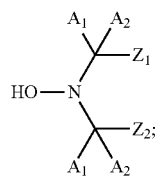

IB

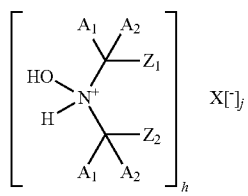

IC the sterically hindered nitroxyl compound is an imidazoline nitroxide of the formula ID, IE, IF or IG,

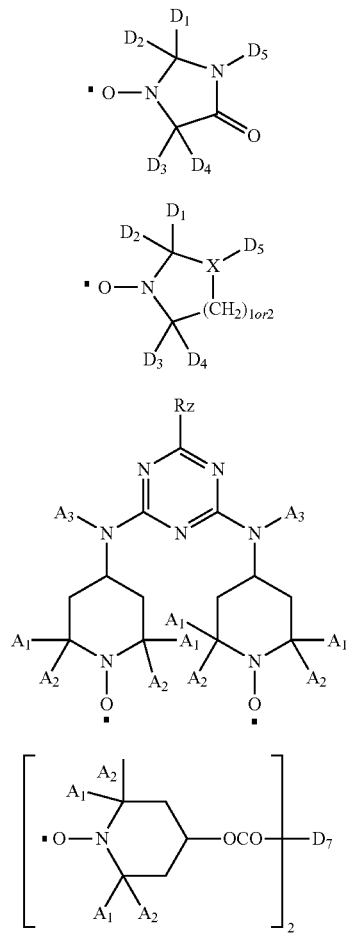

ID

IE

IF

IG wherein a compound of the formula IA, ID, IE, IF or IG instead of the N—O (nitroxyl) moiety comprises a moiety N-Rk, wherein Rk is $C_1$-$C_{18}$alkyl, unsubstituted or $C_1$-$C_7$-alkyl substituted $C_3$-$C_8$-cycloalkyl, mono- or di-(phenyl and/or naphthyl)-$C_1$-$C_{18}$alkyl, norbornyl, naphthyl, phenyl or decahydronaphthyl, wherein phenyl or naphthyl are unsubsituted or substituted by one or more moieties independently selected from hydroxy, halo, methanesulfonyl, carboxy, carbamoyl, aminosulfonyl, sulfuryl, amino, mono- or di-$C_1$-$C_7$-alkylamino and cyano;

(ii) the sterically hindered amino compound is of the formula IA*, ID*, IE*, IF* or IG*,

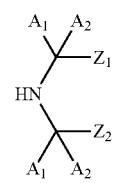

IA*

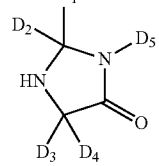

ID*

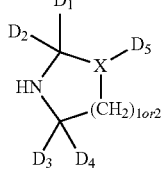

IE*

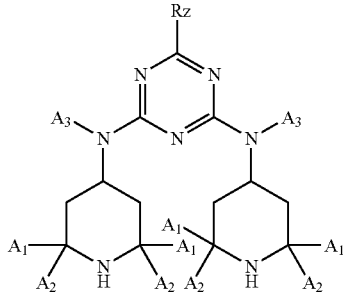

IF*

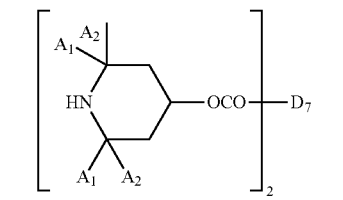

IG* wherein

X is $CH_2$, O, S or N, with the proviso that $D_5$ is absent if X is O or S;

$A_1$ and $A_2$ are independently alkyl of 1 to 4 carbon atoms or are together $C_3$-$C_8$-alkylene;

$A_3$ is hydrogen or $C_1$-$C_{12}$alkyl;

Rz is chloro or —N(2-ethylhexyl)$_2$;

$Z_1$ and $Z_2$ are each alkyl of 1 to 4 carbon atoms or $Z_1$ and $Z_2$ together form a linking moiety which may additionally be substituted by an ester, ether, hydroxy, oxo, cyanohydrin, amide, amino, carboxy or urethane group, h is the number of positive charges and j is the number of negative charges, X is an inorganic or organic anion, where the total charge of cations h is equal to the total charge of anions j;

$D_1$, $D_2$, D and $D_4$ are each independently selected from the group consisting of unsubstituted or substituted $C_1$-$C_{18}$-alkyl and unsubstituted or substituted $C_6$-$C_{18}$-aryl, or one or more of the geminal pairs $D_1$ and $D_2$ and $D_3$ and $D_4$ can together form a 4-8-membered ring, $D_5$ is selected from the group consisting of hydrogen, unsubstituted or substituted $C_1$-$C_{18}$-alkyl, unsubstituted or substituted $C_6$-$C_{18}$-aryl, acyl, or $D_5$ and any one of $D_1$ together can form a 5-8-membered ring; or X and $D_2$ together can form a 5-8 membered ring;

$D_6$ is hydrogen, $C_1$-$C_{18}$alkyl, $C_5$-$C_{12}$-cycloalkyl, $C_7$-$C_{15}$-arylalkyl or $C_6$-$C_{12}$aryl; and $D_7$ is alkylene of 2 to 12 carbon atoms.

2. The process of claim 1, further comprising:

purifying and isolating the product, optionally in the presence of at least one selected from the group consisting of the first additive and the second additive, wherein each additive may be present in free form, salt form, or both.

3. The process of claim 1, wherein the first additive is at least one sterically hindered nitroxyl.

4. The process of claim 1, wherein the bacterial cell is selected from the group consisting of *Escherichia coli, Corynebacterium glutamicum, Brevibacterium, Burkholderia, Bacillus*, a lactic acid bacteria, *Streptomyces lividans, Ralstonia eutrophia, Pseudomonas fluorescens*, and *Staphylococcus carnosus*.

5. The process of claim 1, wherein the product produced by the cell is at least one selected from the group consisting of an antibody, a hormone, a vaccine, a toxin, an enzyme, a protein, a batch protein, an interferon, an interleukin, an inerleukin receptor antagonist, a blood factor, a thrombolytic agent, a hematopoietic growth factor, a growth factor, a tumor necrosis factor, a nucleic acid, and a small molecule, and the product is obtained in free form, salt form, or both.

6. The process of claim 1, further comprising:

mixing the product with at least one selected from the group consisting a pharmaceutically acceptable carrier material and a nutraceutically acceptable carrier material, to obtain a pharmaceutical or nutraceutical composition.

7. A process for enhancing quantity, quality, or both of a product produced by a bacterial cell in a cell culture, the process comprising:

adding at least one first additive selected from the group consisting of a sterically hindered nitroxyl, a sterically hindered hydroxylamine, a sterically hindered hydroxylamine salt compound, a sterically hindered amino compound, and a sterically hindered N-hydrocarbyloxyamine, -to the cell culture comprising the bacterial cell that produces the product, wherein the at least one first additive is added in an amount of 0.0001 to 10% by weight, based on a total weight of the culture; and optionally adding at least one second additive selected from the group consisting of selected from the group consisting of a benzofuranone compound, a nitrone, a phenol antioxidant, a natural antioxidant, a radical scavenger, and a coumestane to the medium, wherein a part or all of the process is carried out in the presence of the first additive or the first and second additives, and each additive may be present in free form, salt form, or both, wherein (i) the sterically hindered nitroxyl compound, sterically hindered hydroxylamine compound, sterically hindered hydroxylamine salt compound is of formulae IA, IB or IC

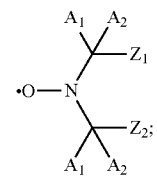

IA

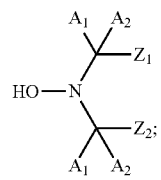

IB

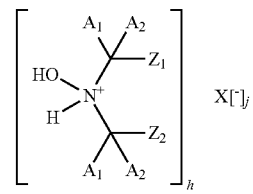

IC the sterically hindered nitroxyl compound is an imidazoline nitroxide of the formula ID, IE, IF or IG,

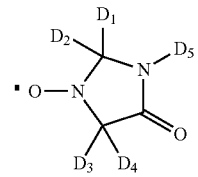

ID

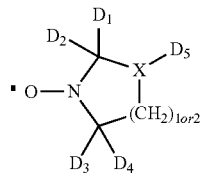

IE

IF

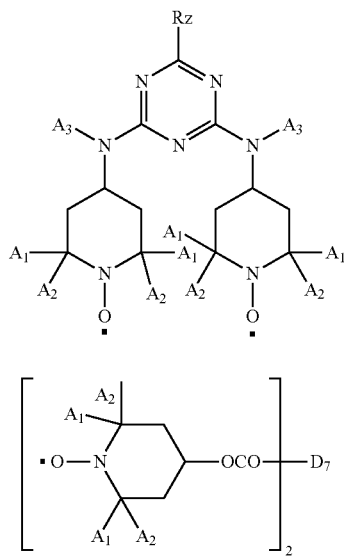

IG wherein a compound of the formula IA, ID, IE, IF or IG instead of the N—O (nitroxyl) moiety comprises a moiety N-Rk, wherein Rk is $C_1$-$C_{18}$alkyl, unsubstituted or $C_1$-$C_7$-alkyl substituted $C_3$-$C_8$-cycloalkyl, mono- or di-(phenyl and/or naphthyl)-$C_1$-$C_{18}$alkyl, norbornyl, naphthyl, phenyl or decahydronaphthyl, wherein phenyl or naphthyl are unsubsituted or substituted by one or more moieties independently selected from hydroxy, halo, methanesulfonyl, carboxy, carbamoyl, aminosulfonyl, sulfuryl, amino, mono- or di-$C_1$-$C_7$-alkylamino and cyano;

(ii) the sterically hindered amino compound is of the formula IA*, ID*, IE*, IF* or IG*,

IA*

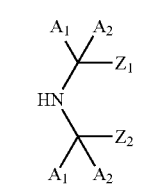

ID*

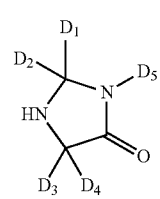

IE*

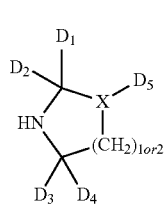

IF*

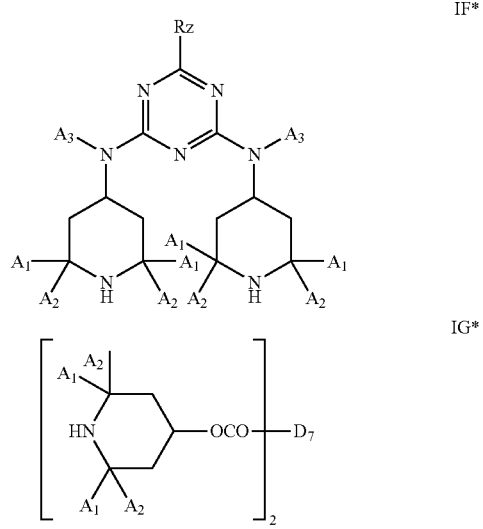

IG* wherein
X is $CH_2$, O, S or N, with the proviso that $D_5$ is absent if X is O or S;
$A_1$ and $A_2$ are independently alkyl of 1 to 4 carbon atoms or are together $C_3$-$C_8$-alkylene;
$A_3$ is hydrogen or $C_1$-$C_{12}$alkyl;
Rz is chloro or —N(2-ethylhexyl)$_2$;
$Z_1$ and $Z_2$ are each alkyl of 1 to 4 carbon atoms or $Z_1$ and $Z_2$ together form a linking moiety which may additionally be substituted by an ester, ether, hydroxy, oxo, cyanohydrin, amide, amino, carboxy or urethane group,
h is the number of positive charges and
j is the number of negative charges,
X is an inorganic or organic anion,
where the total charge of cations h is equal to the total charge of anions j;
$D_1$, $D_2$, D and $D_4$ are each independently selected from the group consisting of unsubstituted or substituted $C_1$-$C_{18}$-alkyl and unsubstituted or substituted $C_6$-$C_{18}$-aryl, or one or more of the geminal pairs $D_1$ and $D_2$ and $D_3$ and $D_4$ can together form a 4-8-membered ring,
$D_5$ is selected from the group consisting of hydrogen, unsubstituted or substituted $C_1$-$C_{18}$-alkyl, unsubstituted or substituted $C_6$-$C_{18}$-aryl, acyl, or $D_5$ and any one of $D_1$ together can form a 5-8-membered ring; or X and $D_2$ together can form a 5-8 membered ring;
$D_6$ is hydrogen, $C_1$-$C_{18}$alkyl, $C_5$-$C_{12}$-cycloalkyl, $C_7$-$C_{15}$-arylalkyl or $C_6$-$C_{12}$aryl; and
$D_7$ is alkylene of 2 to 12 carbon atoms.

8. The process of claim 1, where a concentration of the first additive in the culture medium is in a range of 0.002 to 1% by weight, based on a total weight of the culture.

9. The process of claim 1, wherein the first additive is the sterically hindered nitroxyl compound, sterically hindered hydroxylamine compound, sterically hindered hydroxylamine salt compound is of formulae IA, IB or IC.

10. The process of claim 1, wherein the first additive is the sterically hindered nitroxyl compound is an imidazoline nitroxide of the formula ID, IE, IF or IG.

11. The process of claim 1, wherein the first additive is the compound of the formula IA, ID, IE, IF or IG instead of the N—O (nitroxyl) moiety comprises a moiety N-Rk.

12. The process of claim 1, wherein the first additive is the sterically hindered amino compound is of the formula IA*, ID*, IE*, IF* or IG*.

13. The process of claim 1, wherein the first additive is at least one selected from the group consisting of bis(1-cyclohexyloxy-2,2,6,6-tetramethylpiperidin-4-yl) sebacate, 1-cyclohexyloxy-4-methoxy-2,2,6,6-tetramethylpiperidine, bis(1-heptyloxy-2,2,6,6-tetramethylpiperidin-4-yl) sebacate, 1-hexyloxy-4-methoxy-2,2,6,6-tetramethylpiperidine, bis[1-(2-methyl-2-phenylpropyloxy)-2,2,6,6-tetramethylpiperidin-4-yl] adipate, 1-(2-methyl-2-phenylpropyloxy)-4-benzoyloxy-2,2,6,6-tetramethylpiperidine, 2-chloro-4,6-bis[N-(1-cyclohexyloxy-2,2,6,6-tetramethylpiperidin-4-yl) butylamino]-s-triazine, 2,4,6-tris[N-(1-cyclohexyloxy-2,2,6,6-tetramethylpiperidin-4-yl)butylamino]-s-triazine, bis(1-octyloxy-2,2,6,6-tetramethylpiperidin-4-yl) sebacate, 1-cyclooctyloxy-2,2,6,6-tetramethylpiperidin-4-ol, a reaction product of bis(1-oxyl-2,2,6,6-tetramethylpiperidin-4-yl) sebacate and methylcyclohexane, a reaction product of bis(1-oxyl-2,2,6,6-tetramethylpiperidin-4-yl) succinate and norbornane, a reaction product of 1-oxyl-2,2,6,6-tetramethylpiperidin-4-ol and decahydronaphthalene, a reaction product of bis(1-oxyl-2,2,6,6-tetramethylpiperidin-4-yl) adipate and isooctane, a reaction product of 1-oxyl-4-benzoyloxy-2,2,6,6-tetramethylpiperidine and isooctane, bis[1-(2,2-diphenylpropyloxy)-2,2,6,6-tetramethylpiperidin-4-yl] sebacate, 1-cyclohexyloxy-2,2,6,6-tetramethylpiperidine, bis(1-octadecyloxy-2,2,6,6-tetramethylpiperidin-4-yl) succinate, 1-cyclohexyloxy-4-octadecanoyloxy-2,2,6,6-tetramethylpiperidine, 1-octyloxy-4-benzoyloxy-2,2,6,6-tetramethylpiperidine, 1-cyclohexyloxy-2,2,6,6-tetramethylpiperidine, 1-cyclohexyloxy-2,2,6,6-tetramethylpiperidin-4-ol, 1-cyclohexyloxy-2,2,6,6-tetramethylpiperidin-4-one, bis(1-oxyl-2,2-6-6-tetramethylpiperidin-4-yl) sebacate, bis(1-hydroxy-2,2-6-6-tetramethylpiperidin-4-yl) sebacate, 1-hydroxy-2,2-6-6-tetramethyl-4-acetoxypiperidinium citrate, 1-oxyl-2,2,6,6-tetramethyl-4-acetamidopiperidine, 1-hydroxy-2,2,6,6-tetramethyl-4-acetamidopiperidine,1-hydroxy-2,2,6,6-tetramethyl-4-acetamidopiperidinium bisulfate, 1-oxyl-2,2,6,6-tetramethyl-4-oxo-piperidine, 1-hydroxy-2,2,6,6-tetramethyl-4-oxo-piperidine, 1-hydroxy-2,2,6,6-tetramethyl-4-oxo-piperidinium acetate, 1-oxyl-2,2,6,6-tetramethyl-4-methoxy-piperidine, 1-hydroxy-2,2,6,6-tetramethyl-4-methoxy-piperidine, 1-hydroxyl-2,2,6,6-tetramethyl-4-methoxy-piperidinium acetate, 1-oxyl-2,2,6,6-tetramethyl-4-acetoxypiperidine, 1-hydroxy-2,2,6,6-tetramethyl-4-acetoxypiperidine, 1-oxyl-2,2,6,6-tetramethyl-4-propoxy-piperidine, 1-hydroxy-2,2,6,6-tetramethyl-4-propoxy-piperidinium acetate, 1-hydroxy-2,2,6,6-tetramethyl-4-propoxy-piperidine, 1-oxyl-2,2,6,6-tetramethyl-4-(2-hydroxy-4-oxapentoxy)piperidine, 1-hydroxy-2,2,6,6-tetramethyl-4-(2-hydroxy-4oxapentoxy) piperidinium acetate, 1-oxyl-2,2,6,6-tetramethyl-4-hydroxypiperidine, 1-hydroxy-2,2,6,6-tetramethyl-4-hydroxypiperidine, 1-hydroxy-2,2,6,6-tetramethyl-4-hydroxypiperidinium chloride, 1-hydroxy-2,2,6,6-tetramethyl-4-hydroxypiperidinium acetate, 1-hydroxy-2,2,6,6-tetramethyl-4-hydroxypiperidinium bisulfate, 1-hydroxy-2,2,6,6-tetramethyl-4-hydroxypiperidinium citrate, bis(1-hydroxy-2,2,6,6-tetramethyl-4-hydroxypiperidinium) citrate, tris(1-hydroxy-2,2,6,6-tetramethyl-4-hydroxypiperidinium) citrate, tetra(1-hydroxy-2,2,6,6-tetramethyl-4-hydroxypiperidinium) ethylenediaminetetraacetate, tetra(1-hydroxy-2,2,6,6-tetramethyl-4-acetamidopiperidinium) ethylenediaminetetraacetate, tetra(1-hydroxy-2,2,6,6-tetramethyl-4-oxopiperidinium) ethylenediaminetetraacetate, penta(1-hydroxy-2,2,6,6-tetramethyl-4-hydroxypiperidinium) diethylenetriaminepentaacetate, penta(1-hydroxy-2,2,6,6-tetramethyl-4-acetamidopiperidinium) diethylenetriaminepentaacetate, penta(1-hydroxy-2,2,6,6-tetramethyl-4-oxopiperidinium) diethylenetriaminepentaacetate, tri(1-hydroxy-2,2,6,6-tetramethyl-4-hydroxypiperidinium) nitrilotriacetate, tri(1-hydroxy-2,2,6,6-tetramethyl-4-acetamidopiperidinium) nitrilotriacetate, tri(1-hydroxy-2,2,6,6-etramethyl-4-oxopiperidinium) nitrilotriacetate, penta(1-hydroxy-2,2,6,6-tetramethyl-4-hydroxypiperidinium) diethylenetriaminepentamethylenephosphonate, penta(1-hydroxy -2,2,6,6-tetramethyl-4-acetamidopiperidinium) diethylenetriaminepentamethylenephosphonate, penta(1-hydroxy-2,2,6,6-tetramethyl-4-oxopiperidinium) diethylenetriaminepentamethylenephosphonate, 1-oxyl-2,2,6,6-tetramethyl-4-hydroxypiperidine, 1-hydroxy-2,2,6,6-tetramethyl-4-hydroxypiperidine, 1-hydroxy-2,2,6,6-tetramethyl-4-hydroxypiperidinium chloride, 1-hydroxy-2,2,6,6-tetramethyl-4-hydroxypiperi-dinium acetate, 1-hydroxy-2,2,6,6-tetramethyl-4-hydroxypiperidinium bisulfate, 1-hydroxy-2,2,6,6-tetramethyl-4-hydroxypiperidinium citrate, bis(1-hydroxy-2,2,6,6-tetramethyl-4-hydroxypiperidinium) citrate, tris(1-hydroxy-2,2,6,6-tetramethyl-4-hydroxypiperidinium) citrate, tetra(1-hydroxy-2,2,6,6-tetramethyl-4-hydroxypiperidinium) ethylenediaminetetraacetate, tetra(1-hydroxy-2,2,6,6-tetramethyl-4-acetamidopiperidinium) ethylenediaminetetraacetate, tetra(1-hydroxy-2,2,6,6-tetramethyl-4-oxopiperidinium) ethylenediaminetetraacetate, penta(1-hydroxy-2,2,6,6-tetramethyl-4-hydroxypiperidinium) diethylenetriaminepentaacetate, penta(1-hydroxy-2,2,6,6-tetramethyl-4-acetamidopiperidinium) diethylenetriaminepentaacetate, penta(1-hydroxy-2,2,6,6-tetramethyl-4-oxopiperidinium) diethylenetriaminepentaacetate, 1-hydroxy-2,2,6,6-tetramethyl-4-hydroxypiperidinium citrate, bis(1-hydroxy-2,2,6,6-tetramethyl-4-hydroxypiperidinium) citrate, tris(1-hydroxy-2,2,6,6-tetramethyl-4-hydroxypiperidinium) citrate, 1-hydroxy-2,2,6,6-tetramethyl-4-hydroxypiperidinium DTPA, bis(1-hydroxy-2,2,6,6-tetramethyl-4-hydroxypiperidinium) DTPA, tris(1-hydroxy-2,2,6,6-tetramethyl-4-hydroxy-piperidinium) DTPA, tetrakis(1-hydroxy-2,2,6,6-tetramethyl-4-hydroxypiperidinium) DTPA, pentakis(1-hydroxy-2,2,6,6-tetramethyl-4-hydroxypiperidinium) DTPA, 1-hydroxy-2,2,6,6-tetramethyl-4-hydroxypiperidinium EDTA, bis(1-hydroxy-2,2,6,6-tetramethyl-4-hydroxy-piperidinium) EDTA, tris(1-hydroxy-2,2,6, 6-tetramethyl-4-hydroxypiperidinium) EDTA, tetrakis(1-hydroxy-2,2,6,6-tetramethyl-4-hydroxypiperidinium) EDTA, 1-hydroxy-2,2,6,6-tetramethyl-4-oxo-piperidinium citrate, bis(1-hydroxy-2,2,6,6-tetramethyl-4-oxo-piperidinium) citrate, tris(1-hydroxy-2,2,6,6-tetramethyl-4-oxo-piperidinium) citrate, 1-hydroxy-2,2,6,6-tetramethyl-4-oxo-piperidinium DTPA, bis(1-hydroxy-2,2,6,6-tetramethyl-4-oxo-piperidinium) DTPA, tris(1-hydroxy-2,2,6,6-tetramethyl-4-oxo-piperidinium) DTPA, tetrakis(1-hydroxy-2,2,6,6-tetramethyl-4-oxo-piperidinium) DTPA, pentakis(1-hydroxy-2,2,6,6-tetramethyl-4-oxo-piperidinium) DTPA, 1-hydroxy-2,2,6,6-tetramethyl-4-oxo-piperidinium EDTA, bis(1-hydroxy-2,2,6,6-tetramethyl-4-oxo-piperidinium) EDTA, tris(1-hydroxy-2,2,6,6-tetramethyl-4-oxo-piperidinium) EDTA, tetrakis(1-hydroxy-2,2,6,6-tetramethyl-4-oxo-piperidinium) EDTA, 1-hydroxy-2,2,6,6-tetramethyl-4-acetamidopiperidinium citrate, bis(1-hydroxy-2,2,6,6-tetramethyl-4-acetamidopiperidinium) citrate, tris(1-hydroxy-2,2,6,6-tetramethyl-4-acetamidopiperidinium) citrate, 1-hydroxy-2,2,6,6-tetramethyl-4-acetamidopiperidinium DTPA, bis(1-hydroxy-2,2,6,6-tetramethyl-4-acetamidopiperidinium) DTPA, tris(1-hydroxy-2,2,6,6-tetramethyl-4-acetamidopiperidinium) DTPA, tetrakis(1-hydroxy-2,2,6,6-tetramethyl-4-acetamidopiperidinium) DTPA, pentakis(1-hydroxy-2,2,6,6-tetramethyl-4-acetamidopiperidinium) DTPA, 1-hydroxy-2,2,6,6-tetramethyl-4-acetamidopiperidinium EDTA, bis(1-hydroxy-2,2,6,6-tetramethyl-4-acetamidopiperidinium) EDTA, tris(1-hydroxy-2,2,6,6-tetramethyl-4-acetamidopiperidinium) EDTA, tetrakis(1-hydroxy-2,2,6,6-tetramethyl-4-hydroxypiperidinium) EDTA, 1-hydroxy-2,2,6,6-tetramethyl-4-acetoxypiperidinium citrate, bis(1-hydroxy-2,2,6,6-tetramethyl-4-acetoxypiperidinium) citrate, tris(1-hydroxy-2,2,6,6-tetramethyl-4-acetoxypiperidinium) citrate, 1-hydroxy-2,2,6,6-tetramethyl-4-acetoxypiperidinium DTPA, bis(1-hydroxy-2,2,6,6-tetramethyl-4-acetoxypiperidinium) DTPA, tris(1-hydroxy-2,2,6,6-tetramethyl-4-acetoxypi-peridinium) DTPA, tetrakis(1-hydroxy-2,2,6,6-tetramethyl-4-acetoxypiperidinium) DTPA, pentakis(1-hydroxy-2,2,6,6-tetramethyl-4-acetoxypiperidinium) DTPA, 1-hydroxy-2,2,6,6-tetramethyl-4-acetoxypiperidinium EDTA, bis(1-hydroxy-2,2,6,6-tetramethyl-4-acetoxypipe-ridinium) EDTA, tris(1-hydroxy-2,2,6,6-tetramethyl-4-acetoxypiperidinium) EDTA, tetrakis(1-hydroxy-2,2,6,6-tetramethyl-4-acetoxypiperidinium) EDTA, 1-(2-hydroxy-2-methylpropoxy)-4-octadecanoyloxy-2,2,6,6-tetramethylpiperidine, 1-(2-hydroxy-2-methylpropoxy)-4-hydroxy-2,2,6,6-tetramethylpiperidine, and a salt thereof.

\* \* \* \* \*